United States Patent [19]
Holmes et al.

[11] Patent Number: 5,401,827
[45] Date of Patent: Mar. 28, 1995

[54] SEMICONDUCTIVE COPOLYMERS FOR USE IN LUMINESCENT DEVICES

[75] Inventors: Andrew Holmes; Donal D. Bradley; Richard H. Friend; Arno Kraft; Paul Burn; Adam Brown, all of Cambridge, United Kingdom

[73] Assignee: Cambridge Display Technology Limited, Cambridge, United Kingdom

[21] Appl. No.: 748,777

[22] Filed: Aug. 22, 1991

[30] Foreign Application Priority Data

Aug. 24, 1990 [GB] United Kingdom ............... 9018698

[51] Int. Cl.$^6$ ............................................. C08G 75/04
[52] U.S. Cl. .................................. 528/374; 528/373; 528/380; 528/391; 528/396; 528/481; 528/487; 528/490; 524/80; 524/401
[58] Field of Search ............... 528/374, 380, 481, 502, 528/396, 391, 487, 490, 588, 373; 524/401, 80

[56] References Cited

U.S. PATENT DOCUMENTS

| | | | |
|---|---|---|---|
| 3,621,321 | 11/1971 | Williams et al. | 313/108 A |
| 4,808,681 | 2/1989 | Haper et al. | 528/380 |
| 4,868,284 | 9/1989 | Murase et al. | 528/481 |
| 4,900,782 | 2/1990 | Han et al. | 525/398 |
| 4,950,950 | 8/1990 | Perry et al. | 313/504 |
| 5,053,166 | 10/1991 | Murase et al. | 524/80 |
| 5,064,572 | 11/1991 | Ohnishi et al. | 524/401 |

FOREIGN PATENT DOCUMENTS

| | | |
|---|---|---|
| 0182548A3 | 5/1986 | European Pat. Off. |
| 0373582A1 | 6/1990 | European Pat. Off. |
| 0388768A2 | 9/1990 | European Pat. Off. |
| WO88/00954 | 2/1988 | WIPO |

OTHER PUBLICATIONS

Askari et al., "Soluble Substituted–PPV Conducting Polymers: Spectroscopic Studies", *Synth. Met.*, 29:E129 (1989).
Bao et al., "Synthesis of Connjugated Polymer by the Stille Coupling Reaction", *Chem. Mater.*, 5:2–3 (1993).
Gregorius et al., "A Study on the Elimination Reaction of Sulfonium Polyelectrolyte Precursor Polymers to Poly(p-phenylenevinlene)", *Agnew. Chem. Int. Ed. Engl.*, 31:1653–1655 (1992).
Halliday et al., "meta-Phenylene Units as Conjugation Barriers in Phenylenevinylene Chains", *J. Chem. Soc. Comm.*, at pp. 1685–1687 (1992).
Han et al., "Conveniently Processible Forms of Electrically Conductive Poly(Dibutoxyphenylene Vinylene", *Mol. Cryst. Liq. Cryst.*, 189:183–192 (1990).
Hawley's Condensed Chemical Dictionary, 11th Edition, at p. 1033 (1987).
Kretzschmann et al., "A New Synthesis of Soluble Poly(1,4-phenylenevinylene)s and Poly(2-,5-pyrimidinylenevinylene)", *Tetrahedron Letters,* 32:5059–5062 (1991).

(List continue on next page.)

Primary Examiner—John Kight, III
Assistant Examiner—Richard Jones
Attorney, Agent, or Firm—Merchant, Gould, Smith, Edell, Welter & Schmidt

[57] ABSTRACT

A semiconductive conjugated copolymer comprises at least two chemically different monomer units which, when existing in their individual homopolymer forms, have different semiconductor bandgaps. The proportion of said at least two chemically different monomer units in the copolymer is selected to control the semiconductor bandgap of the copolymer so as to control the optical properties of the copolymer. The copolymer is formed in a manner enabling it to be laid down as a film without substantially affecting the luminescent characteristics of the copolymer and is stable at operational temperature.

The semiconductor bandgap may be spatially modulated so as to increase the quantum efficiency of the copolymer when excited to luminesce, to select the wavelength of radiation omitted during luminescence or to select the refractive index of the copolymer.

49 Claims, 56 Drawing Sheets

OTHER PUBLICATIONS

Louwet et al., "The Synthesis of Poly(1,4-phenylene-1,2-ethanediyl) Derivatives: An Adaptation of the Wessling Route", *Synthetic Metals*, 52:125–130 (1992).

Rehahn et al., "Soluble Poly(para-phenylene)s, 3$^{a)}$: Variation of the Length and the Density of the Solubilizing Side Chains", *Makromol. Chem.*, 191:1991–2003 (1990).

Vestweber et al., "Progress Towards Processible Materials for Light–Emitting Devices Using Poly(p-phenylphenylenevinylene)", *Adv. Mater.*, 4, No. 10 (1992).

Hayashi et al., "Quenching of Photoluminescence in Poly(thiophene) Films by Electrochemical Doping", *Solid State Communications*, 61:249–251 (1987).

Electric Phenomena, vol. 111, 1989, pp. 812–813 Polymer Communications, vol. 28, Sep. 1987.

Journal of Molecular Electronics, vol. 4, No. 1, Jan.–Mar. 1988, pp. 37–46 Chemistry Letters, No. 7, 1988, pp. 1201–1204.

Polymer, 1989, vol. 30, Jun. 1989 (Conf. Issue), pp. 1041–1047 Makromol. Chem., vol. 190, 1987, pp. 389–397.

Polymer Bulletin, Spring 1989, No. 4, pp. 409–412.

POLYMER, 1990, vol. 31, Jun. 1990, pp. 1137–1141.

FIG. 2a
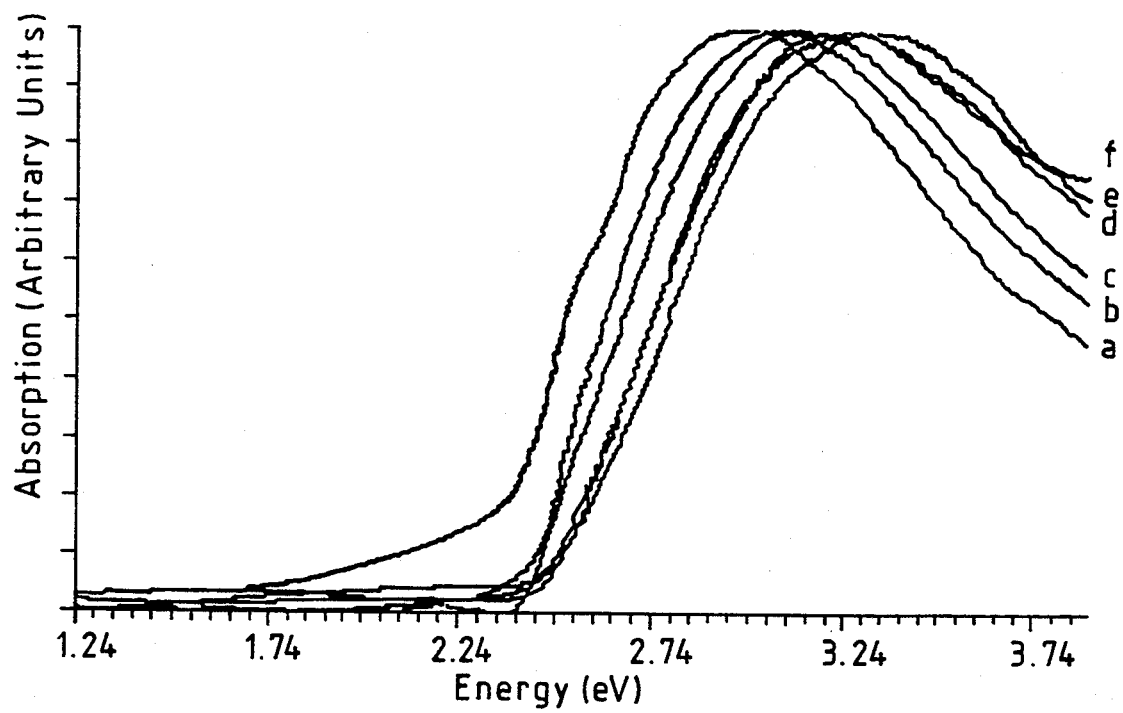
FIG. 2b  PMPV absorption spectrum
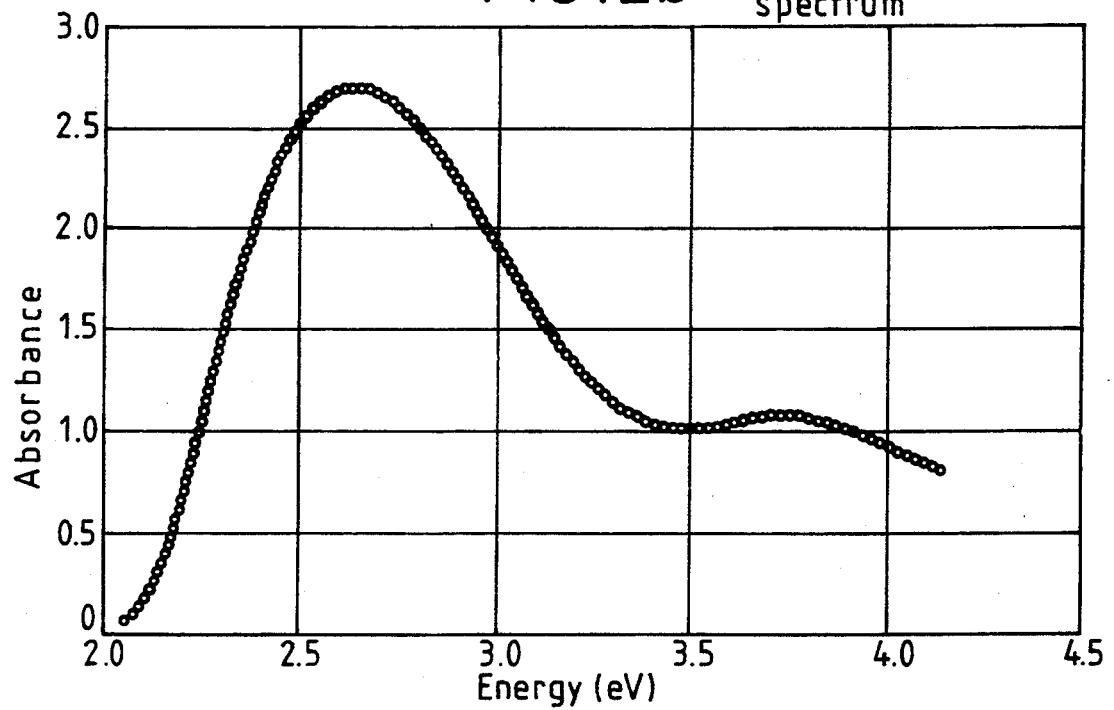

PPV4/7/90B
MG 01-69. Thick PPV on glass

210390 PMPV11
PMPV (200C + HCl For 2 hours)
Unnormalised photoluminescance

Room temperature

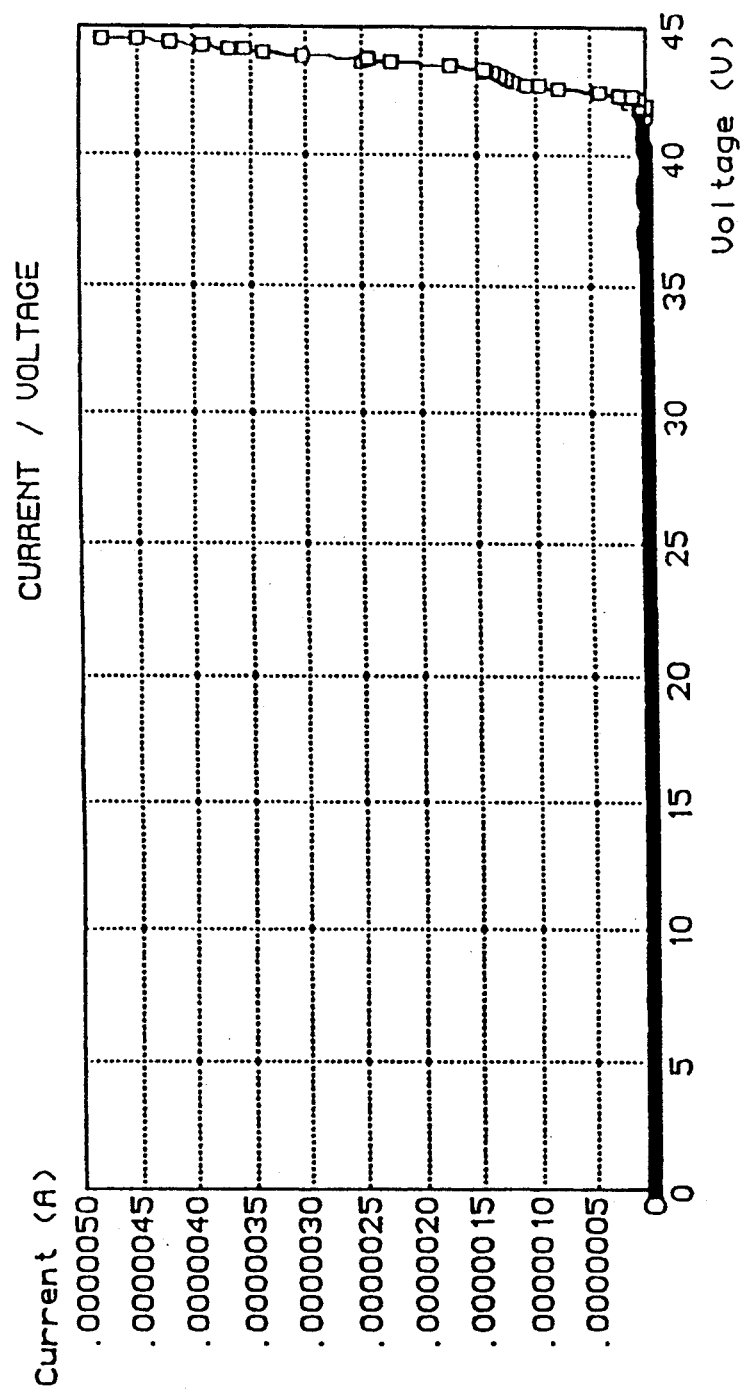

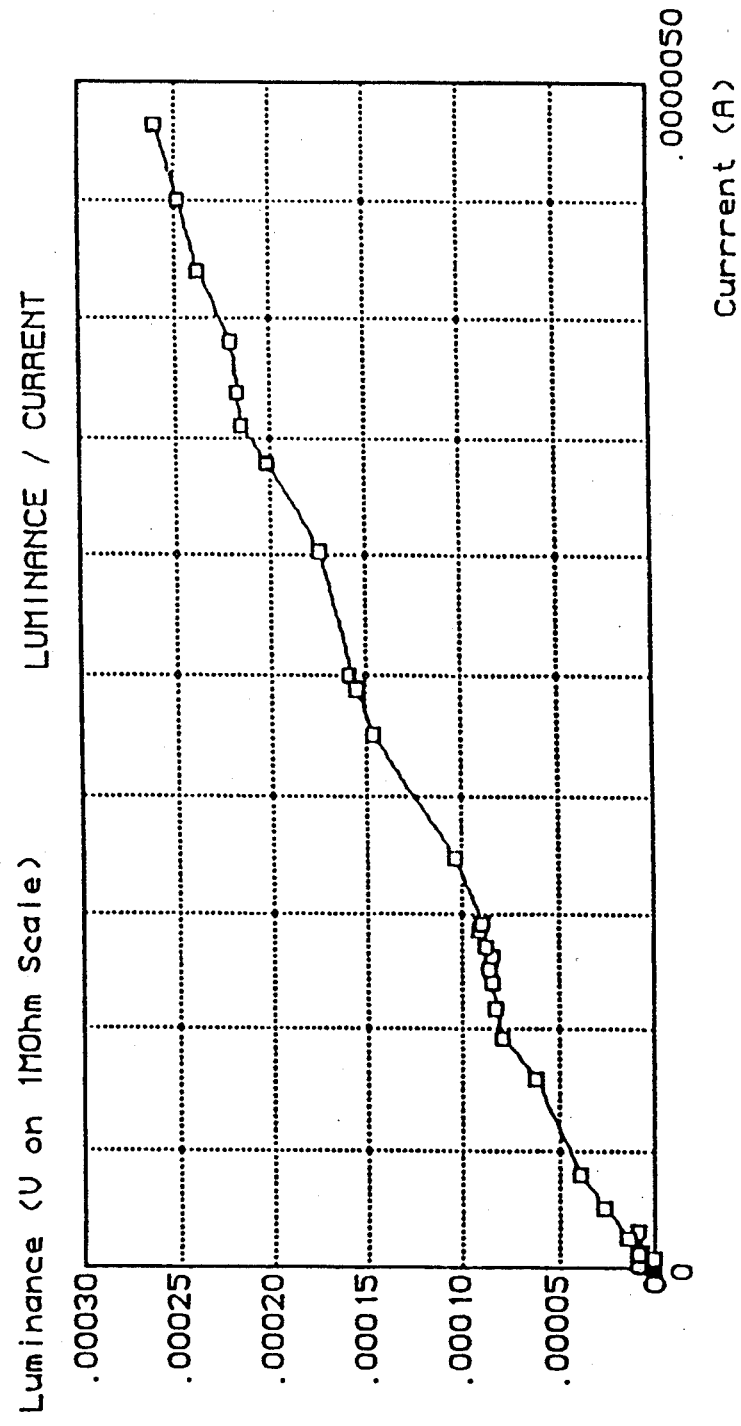

Electroluminescent Quantum Yield of the Random Copolymers of PPV and Dimethoxy PPV Electroluminescent Quantum Yield of the Random Copolymers of PPV and PTV Electroluminescent Quantum Yield of the Random Copolymers of PPV and Dimethyl PPV

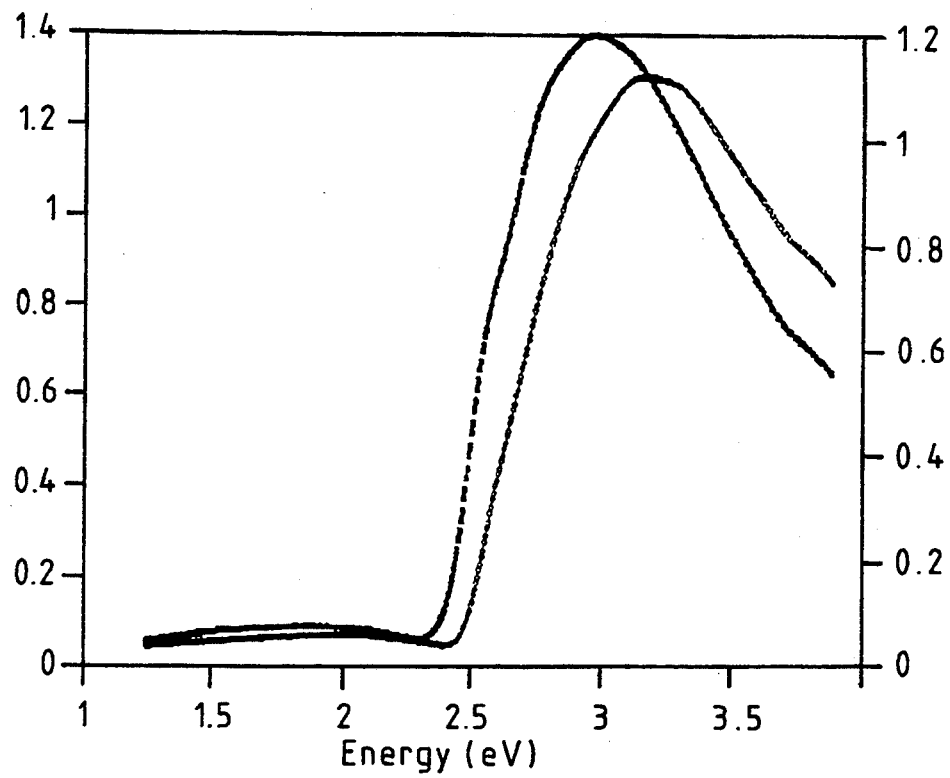
FIG. 16 PLB 03-12 Absorption Spectra
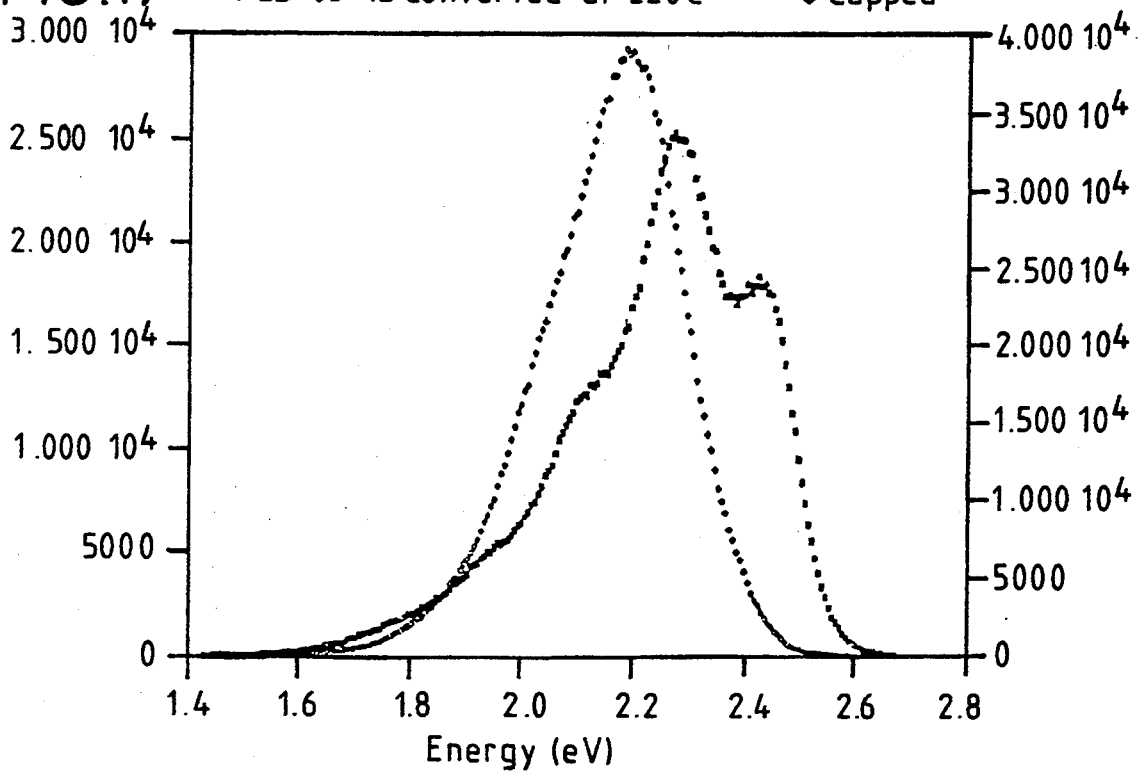
FIG. 17 PLB 03-12 Converted at 220 C RJ02-06 5%MMPPPV Prec
sample data
 20%/10%/5% MMPPPV/PPV Prec (upwards)

RJ02-07 PREC 20%MMPPPV/PPV
 20%/10%/5% MMPPPV/PPV Prec (upwards)
Thu, Jul 4, 1991, 10:15:28

Photoluminescence Spectrum 5%PPV/95%MEHPPV

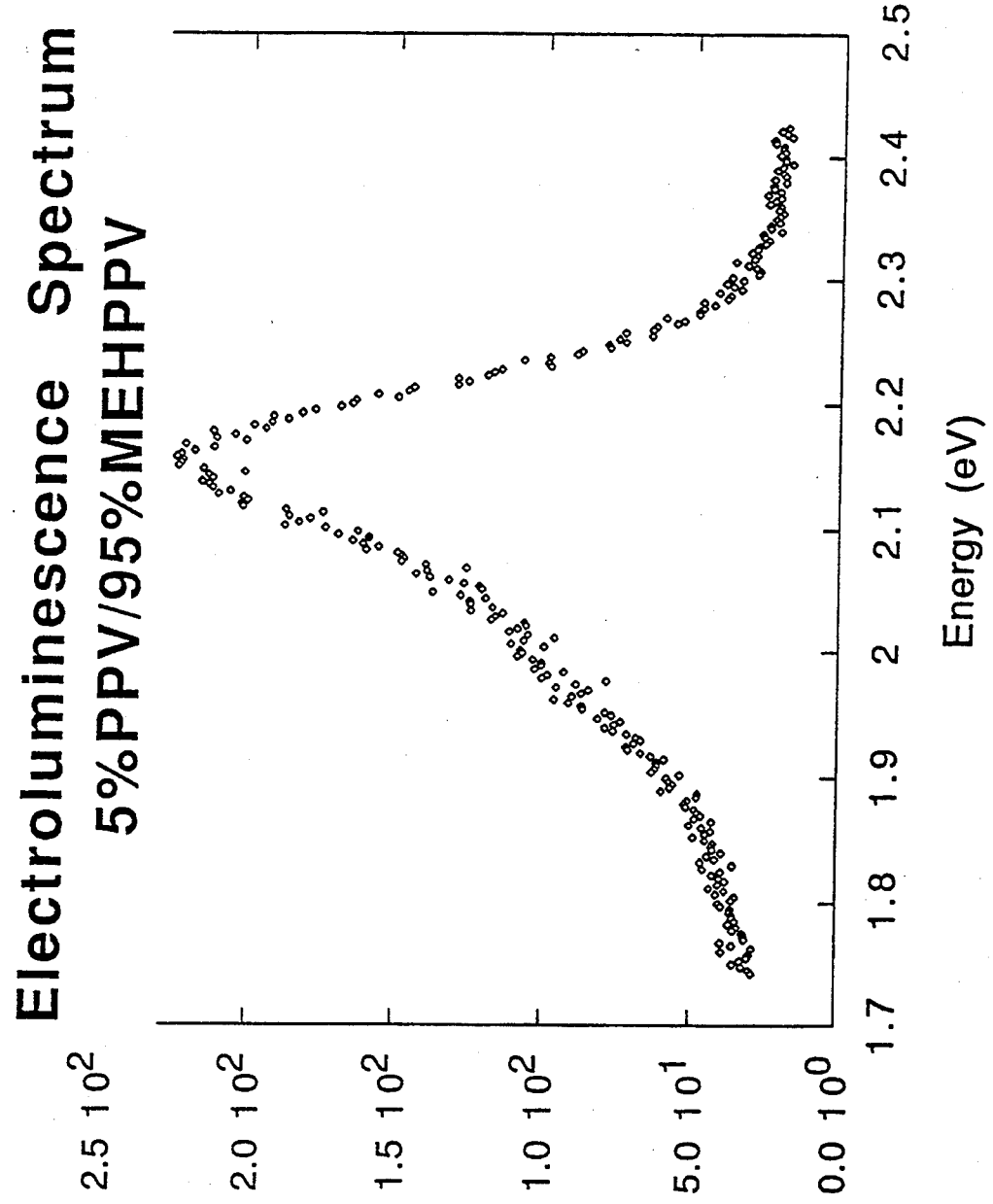

DATA PRESENTATION Panel

Sample 20%
Run b
Date 25-7-91

Bottom Contact      ITO
Top Contact      Al
Bottom Contact Thickness
Top Contact Thickness      1000 Å

Electroluminescent Layer      20%ppv/80%mehppv
Electroluminescent Layer Thickness      800 Å

FIG. 32
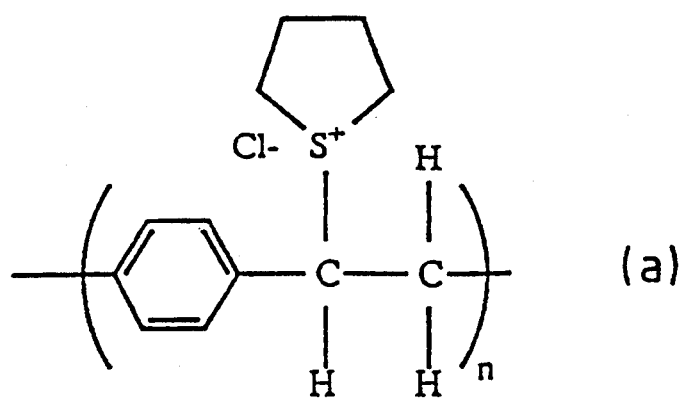
THT-leaving PPV Precursor
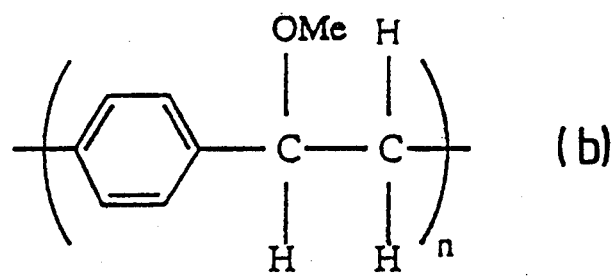
MeO-leaving PPV Precursor
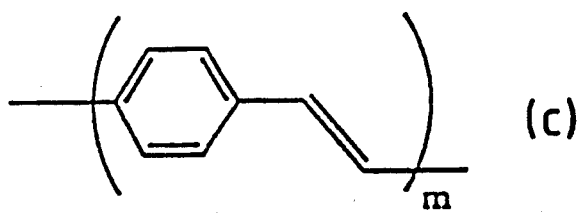
PPV
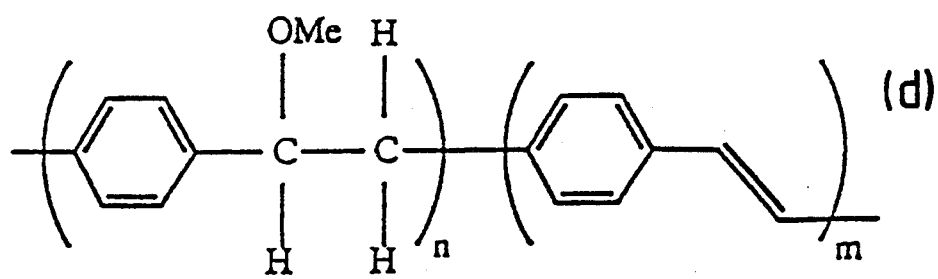
Partially converted MeO-leaving PPV RJ01-30 and RJ01-22 converted 300C in vacuo for 12h

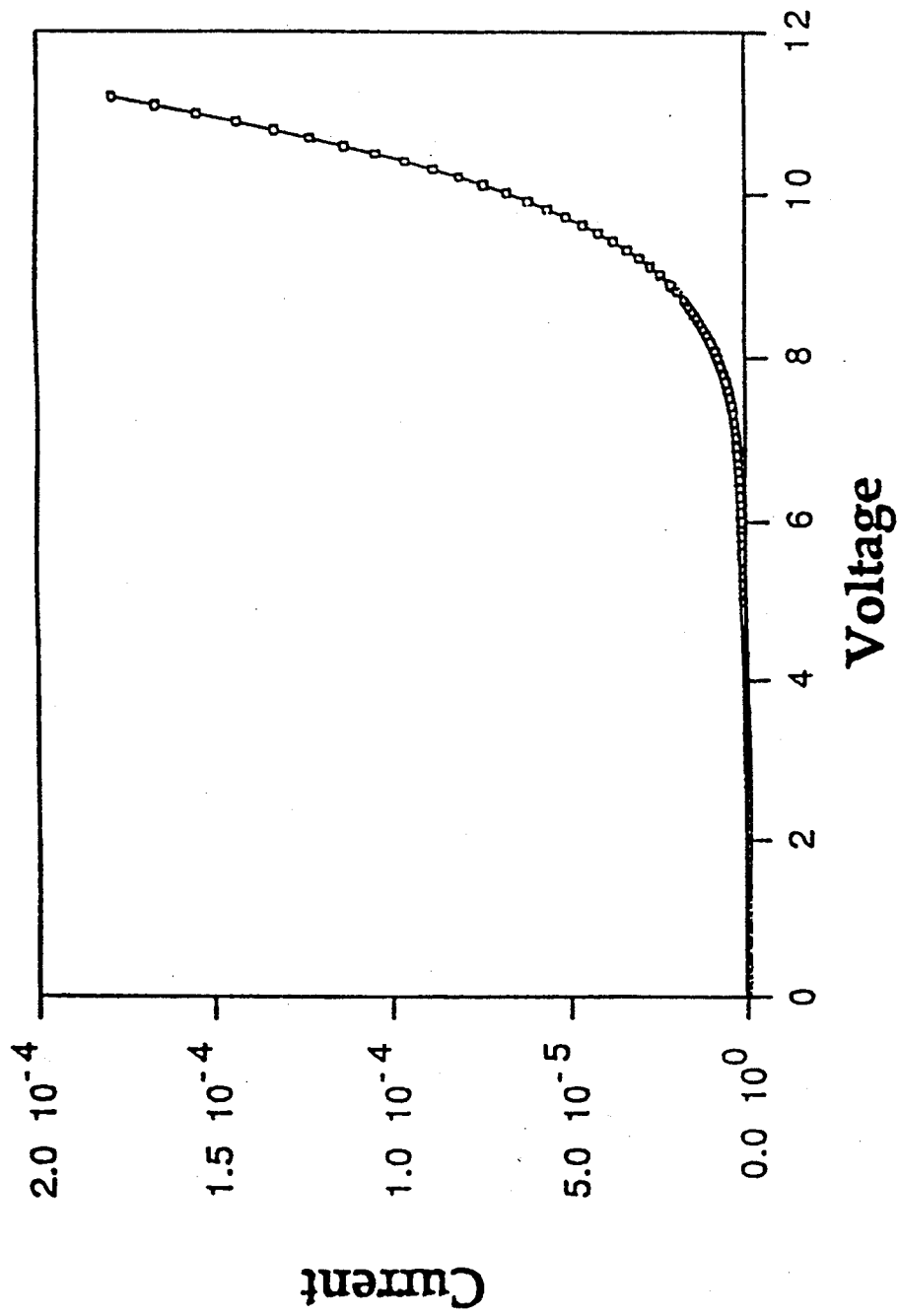
FIG. 36a THT-leaving PPV Current-Voltage Characteristic

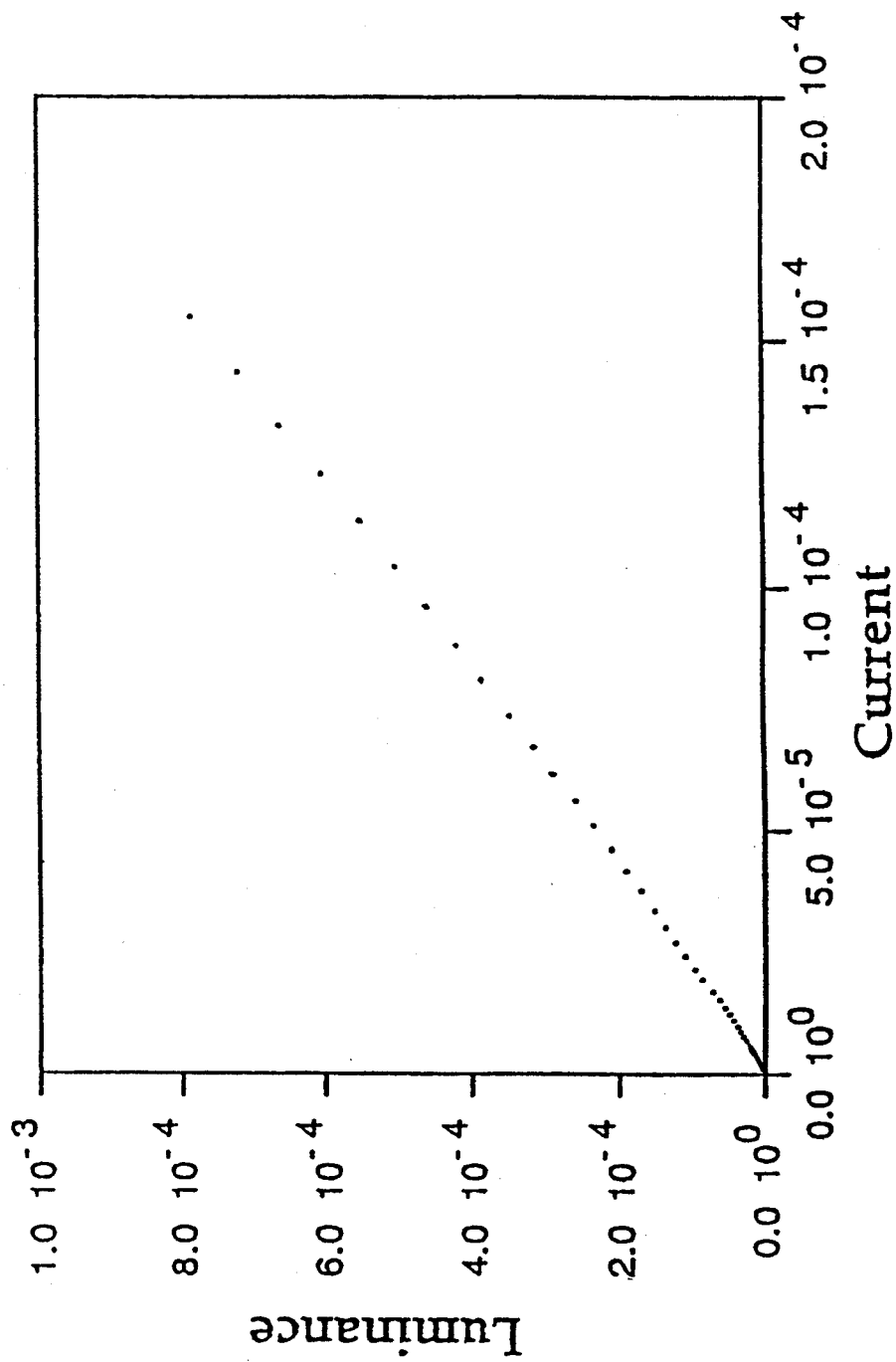
FIG. 36b THT-leaving PPV Luminance/Current Characteristic

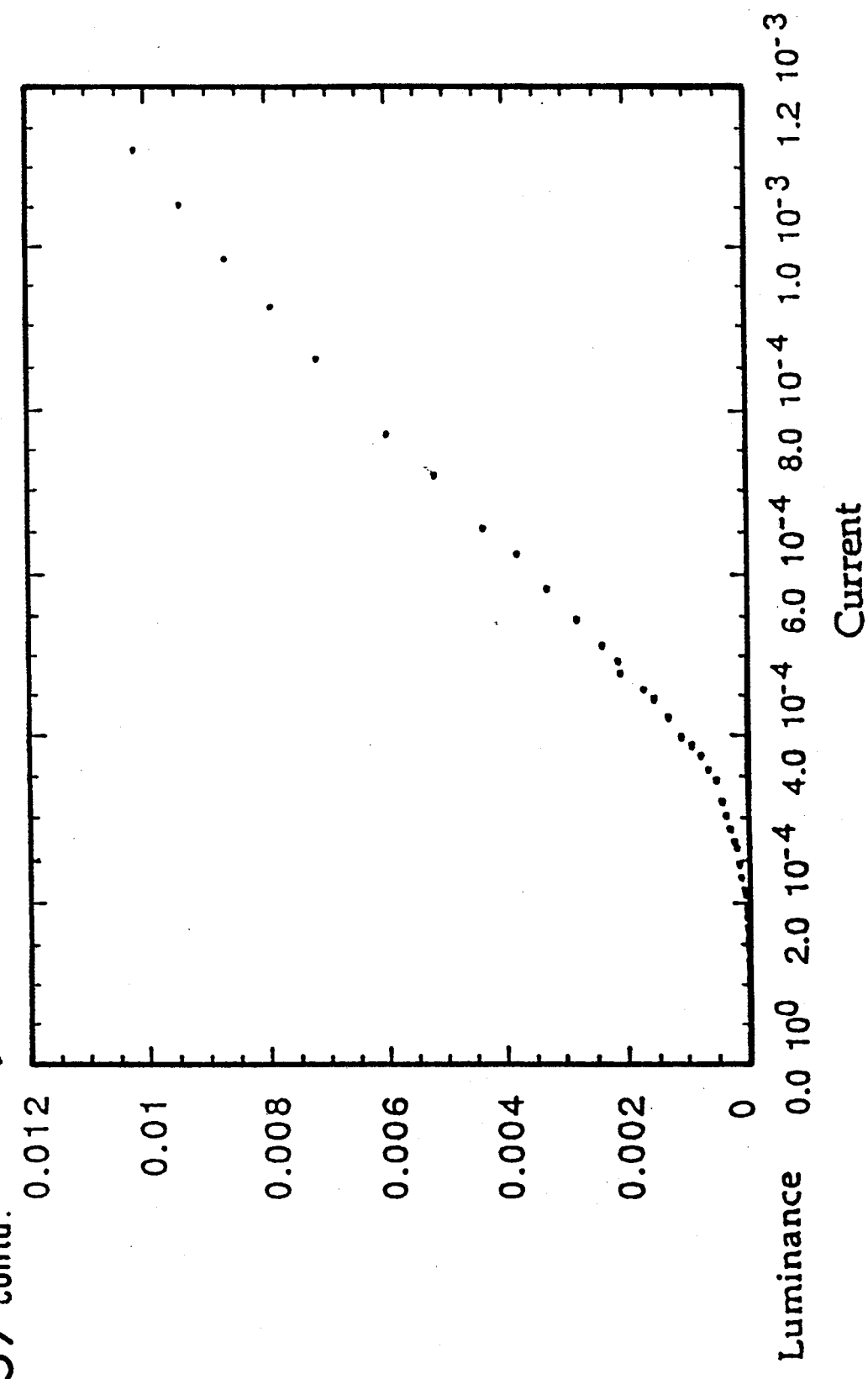
FIG. 37 contd.

a) Random Copolymers of PPV and DMeOPPV Precursor b) Random Copolymers of PPV and DMeOPPV as converted thermally in vacuo c) Random Copolymers of PPV and DMeOPPV as converted thermally in prescence of H⁺

FIG. 40  Copolymers of PPV and DMeOPPV converted for 2 hours at 220C

I.R. Absorption Spectra of the 20% Random Co-polymer of DMeOPPV and PPV
a) precursor (free-cast film)  b) spin-coated film on KBr disc converted at 220°C in vacuo for 2hrs  c) same sample further converted for 2hrs in Ar/HCl at 220°C

SEMICONDUCTIVE COPOLYMERS FOR USE IN LUMINESCENT DEVICES

FIELD OF THE INVENTION

This invention relates to semiconductive copolymers for use in luminescent devices, particularly electroluminescent devices.

BACKGROUND TO THE INVENTION

It has been shown that certain conjugated polymers show a relatively high quantum efficiency for the radiative decay of singlet excitons. Of these, poly-p-phenylene vinylene (PPV) can be prepared via a solution-processible precursor polymer, and although itself intractable and not easily processed, can be prepared in the form of thin films of high quality by thermal conversion of the as-prepared films of the precursor polymer. Details of this general synthesis method are given in "Precursor route poly(p-phenylene vinylene): polymer characterisation and control of electronic properties" D. D. C. Bradley, J. Phys. D: Applied Phys. 20, 1389 (1987), and "Spectroscopic and cyclic voltammetric studies of poly(p-phenylene vinylene) prepared from two different sulphonium salt precursor polymers", J. D. Stenger-Smith, R. W. Lenz and G. Wegner, Polymer 30, 1048 (1989). Measurements of photoluminescence, PL, have been reported by for example "Optical Investigations of Conjugated Polymers" R. H Friend, J. Molecular Electronics, 4, 37 (1988), and "Photoexcitation in Conjugated Polymers" R. H. Friend, D. D. C. Bradley and P. D. Townsend, J. Phys. D 20, 1367 (1987). In our earlier International Patent Application No. PCT/GB90/00584 (Publication No. PCT/WO90/13148) films of PPV are disclosed as being useful as the emissive layer in a structure exhibiting electroluminescence (EL). This structure requires injection of electrons and holes from either side of the active (i.e. emissive) region of the film, and various metallic contact layers can be used. In sandwich-like structures, and for emission from the plane of the device, one of these should be semi-transparent.

The advantages of using polymers of this type as the emissive layer in EL structures include:
 (a) ease of fabrication of large area structures. Various methods are available for solution-processing of the precursor polymer, including spin-coating from solution which is the preferred method, and dip-coating;
 (b) intractability of the polymer film, giving desirable strength, resistance to degradation from heat and exposure to oxygen, resistance to structural changes such as recrystallisation and shrinkage, and resistance to ion migration;
 (c) intrinsically good properties for luminescence, including low densities of charges and/or spin-carrying defects.

However, there is some evidence that the quantum yield for radiative decay of the excited states is lowered through their migration to non-radiative decay centres, see for example "Radiative and Non-Radiative Recombination Processes in Photoexcited Poly(p-phenylenevinylene)", D. D. C. Bradley, R. H. Friend, K. S. Wong, W. Hayes, H. Lindenberger and S. Roth, Springer Solid State Sciences, 76, 107 (1987), and "Light-Induced Luminescence Quenching in Precursor-Route Poly(p-phenylenevinylene)" D. D. C. Bradley and R. H. Friend, J. Phys. CM 1, 3671 (1989).

SUMMARY OF THE INVENTION

The present invention is directed to providing polymers for use as the emissive layer in EL structures which overcome these difficulties.

According to one aspect of the present invention there is provided a semiconductive conjugated copolymer comprising at least two chemically different monomer units which, when existing in their individual homopolymer forms, have different semiconductor bandgaps, the proportion of said at least two chemically different monomer units in the copolymer having been selected to control the semiconductor bandgap of the copolymer so as to control the optical properties of the copolymer, said copolymer having been formed in a manner enabling it to be laid down as a film without substantially affecting the luminescent characteristics of the copolymer, said copolymer being stable at operational temperature.

The operational temperature depends upon the use to which the copolymer is put. Typically, use of the copolymer in luminescence devices may require the operational temperature to be ambient temperature or room temperature. Preferably, the stability of the copolymer extends to operational temperatures in the range 0°–150° C., more preferably down to 77° K. Preferably the monomer units in the copolymer are arylene vinylene units.

A semiconductor is a material that is able to accommodate charged excitations which are able to move through this material in response to an applied electrical field. Charge excitations are stored in the semiconductor in states which are (or are derived from) conduction band states (in the language of quantum chemisty, lowest unoccupied molecular orbitals, LUMOs) if negatively charged, or valence band states (highest occupied molecular orbitals, HOMOs) if positively charged. The semiconductor band gap is the energy difference between valence and conduction bands (or from HOMO to LUMO)

The present application is primarily concerned with copolymers in which the material is made up of chemically distinct regions of polymer chain. A convenient description of the electronic states (molecular orbitals) is one in which the wavefunctions are substantially localised on a region of chain of one chemical type. It is useful to define the semiconductor bandgap locally, i.e. as the energy gap between HOMO and LUMO on a particular sequence of polymer chain to which the HOMO and LUMO wavefunctions are substantially confined. One can expect to find a variation of gap from HOMO to LUMO between regions of one chemical type those of another. This may be described as a spatial modulation of the bandgap.

The inventors have found that by modulating the semiconductor bandgap of the copolymer it is possible to increase the quantum efficiency of the copolymer when excited to luminesce. Quantum efficiency for luminescence may be defined as photons out per excited state. For photoluminescence this is identified as photons out per photon absorbed. For electroluminescence this is defined as photons out per electron injected into the structure.

They have also found that the semiconductor bandgap can be modulated to control the wavelength of radiation emitted during luminescence. This gives the very desirable feature of controlling the colour of light output from the polymer. The inventors have also found that the Semiconductor bandgap is a factor affecting the refractive index of the copolymer.

In one aspect, the chain of the copolymer is fully conjugated. In a further aspect, at least one of the monomer units is not fully conjugated in the chain of the copolymer. It will be apparent that it is an important feature of the invention that the copolymer, when laid down as a film, comprises two chemically different monomer units. This can be achieved by converting a suitable precursor copolymer comprising a selected proportion of the different monomer units or by controlling the extent of conversion of a precursor polymer into a conjugated copolymer. The conjugated polymers used here are all examples of semiconductors, and there is some control of bandgap through adjustment of the repeat units of the chain. However, it is also found that it is useful to incorporate some units of non-conjugated polymers to form some of the copolymers. In this case, the non-conjugated section of the chain would function as a very large gap semiconductor, so that under the conditions of operation found here it would behave as an insulator, i.e. there would be little or no charge storage on or movement through such a region of the chain. In this case, the material as a whole will still function as a semiconductor so long as there is a path through the bulk of the sample that passes entirely through the semiconducting regions of the chain (those that are conjugated). The threshold for the existence of such a path is termed the percolation threshold, and is usually found to be in the region of 20% volume fraction of non-insulating material. In the present specification, all such copolymers are well above this percolation threshold and can be termed as semiconductors.

In a preferred embodiment the present invention provides a conjugated poly(arylene vinylene) copolymer capable of being formed as a thin electroluminescent film, wherein a proportion of the vinylic groups of the copolymer are saturated by inclusion of a modifier group substantially stable to elimination during formation of the film, whereby the proportion of saturated vinylic groups controls the extent of conjugation, thereby modulating the semiconductor ($\pi$—$\pi$*) bandgap of the copolymer.

In another aspect, the invention provides a method of manufacturing a semiconductive copolymer comprising:

(a) reacting a quantity of a first monomer with a quantity of a second monomer in a solvent comprising a mixture of water and an alcohol;
(b) separating the reaction product therefrom;
(c) dissolving the reaction product in an alcohol the same as or different from said first mentioned alcohol;
(d) forming from the result of step (c) a conjugated polymer film the quantities in step (a) being selected so that in the conjugated polymer the semiconductor bandgap is controlled so as to control the optical properties of the copolymer.

Step (a) is preferably carried out in the presence of a base.

The present invention also provides a method of forming a conjugated poly(arylene vinylene) a polymer as defined above, which method comprises heating substantially in the absence of oxygen a poly(arylene-1,2-ethanediyl) precursor copolymer wherein a proportion of the ethane groups include a modifier group substituent and at least some of the remaining ethane groups include a leaving group substituent, whereby elimination of the leaving group substituents occurs substantially without elimination of the modifier group substituents so as to form the conjugated poly(arylene vinylene) copolymer.

The extent of conjugation of the conjugated poly(arylene vinylene) copolymer can be tailored by appropriate selection of the arylene constituents of the copolymer and of the modifier group. For example, phenylene moieties incorporating electron-donating substituent groups or arylene moieties with oxidation potentials lower in energy than that of phenylene are found to incorporate the modifier group preferentially as compared with the corresponding unsubstituted arylene moiety. Thus, the proportion of vinylic groups saturated by incorporation of the modifier group can be controlled by selection of the arylene moieties' substituents and the extent of conjugation of the copolymer may be concomitantly modulated. The extent of conjugation of the copolymer affects the $\pi$—$\pi$* bandgap of the copolymer. Therefore, selection of appropriate reaction components may be used to modulate the bandgap. This property may be exploited, for example, in the construction of electroluminescent devices as described in more detail with reference to the preferred embodiment.

In a further aspect, the present invention also provides a poly(arylene-1,2-ethanediyl) precursor copolymer wherein a proportion of the ethane groups include a modifier group substituent and at least some of the remaining ethane groups include a leaving group substituent the precursor copolymer being convertible by elimination of the leaving group substituents into a conjugated polycarylene vinylene) copolymer as defined above.

The invention also provides a method of conversion of the precursor into its copolymer in which the extent of elimination of the leaving group constituents is controlled to control the bandgap of the copolymer to define both the colour of luminescence of the resulting copolymer film and its quantum efficiency for luminescence;

In a further aspect, there is provided a method of forming a poly(arylene-1,2-ethanediyl) precursor copolymer as defined above, which method comprises reacting a first monomer component with a second monomer component, in the presence of base and a solvent comprising a modifier group, wherein the first monomer component comprises a first arylene moiety substituted with —$CH_2L^1$ and —$CH_2L^2$ and the second monomer component comprises a second arylene moiety substituted with —$CH_2L^3$ and —$CH_2L^4$, in which $L^1$, $L^2$, $L^3$ and $L^4$ each represents a leaving group substituent which may be the same or different from one another. This method may constitute a first step in the formation of the conjugated poly(arylene vinylene) copolymer.

A function of the modifier group is to interrupt the conjugation of the poly(arylene vinylene) copolymer by saturation of the vinylic groups of the copolymer chain. Thus, for the modifier group to be successful in this function it must be relatively stable to elimination during formation of the poly(arylene vinylene) copolymer. Typical modifier groups include:

RO—, RS—, ArO—, ArS—, NC—,

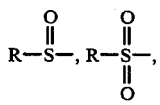

RSe, HO—

A preferred modifier group is a $C_1$ to $C_6$ alkoxy group, more preferably a methoxy group.

The poly(arylene-1,2-ethanediyl) precursor copolymer may be formed in a first step by reacting a first monomer component with a second monomer component, in the presence of base and a solvent comprising the modifier group, wherein the first monomer component comprises a first arylene moiety substituted with $-CH_2L^1$ and $-CH_2L^2$ and the second monomer component comprises a second arylene moiety substituted with $-CH_2L^3$ and $-CH_2L^4$, in which $L^1$, $L^2$, $L^3$ and $L^4$ each represents a leaving group substituent which may be the same or different from one another.

In the step of forming the poly (arylene-1,2-ethanediyl) precursor copolymer the solvent preferably also includes water. Thus, for aqueous solvents, the modifier group must be present as a water miscible polar solvent/reagent. Where the modifier group is alkoxy, the corresponding solvent or solvent component would therefore be an alcohol. Preferably the solvent comprises at least 30% modifier group by weight. More preferably the solvent is water: methanol at a ratio of 1:1 or lower. Modifier groups may be introduced selectively either during formation of the precursor copolymer or by displacement reactions on the precursor copolymer.

The identity of the leaving groups is not particularly critical provided that the first and second monomer components may react together in the presence of base and provided that the leaving group substituents on the poly(arylene-1,2-ethanediyl) precursor copolymer may eliminate upon heating. Typical leaving groups include 'onium salts in general, bearing a non-basic counter anion. Sulphonium salts, halides, sulphonates, phosphates or esters are suitable examples of leaving groups. Preferably a sulphonium salt such as a tetrahydrothiophenium salt is used.

Throughout this specification the term arylene is intended to include in its scope all types of arylenes including heteroarylenes as well as arylenes incorporating more than one ring structure, including fused ring structures.

At least two arylene moieties are present in the copolymer chain and these may be substituted or unsubstituted arylene or heteroarylene moieties. Suitable substituents include alkyl, O-alkyl, S-alkyl, O-aryl, S-aryl, halogen, alkyl sulphonyl and aryl sulphonyl. Preferred substituents include methyl, methoxy, methyl sulphonyl and bromo, and the arylenes may be substituted symmetrically. In a more preferred embodiment of the invention, one of the arylene moieties of the copolymer is unsubstituted and comprises para-phenylene. Preferably, the second component is selected from the group comprising
2,5-dimethoxy-para-phenylene, 2,5-thienylene
2,5-dimethyl-para-phenylene,
2-methoxy-5-(2'methylpentyloxy)-para-phenylene and
2-methoxy-5-(2'ethylhexyloxy)-para-phenylene. More preferably the para-phenylene moiety is present in the copolymer chain in an amount resulting from conversion of a precursor copolymer formed by reaction of at least 70 mole % of the PPV precursor monomer unit.

Referring in particular to the method of forming the conjugated polyarylene vinylene copolymer, this can be effected by heating, preferably in a temperature range of 70°–300° C. The heating is performed substantially in the absence of oxygen, for example under an inert atmosphere such as that of one or more inert gases or under vacuum.

In the step of forming the precursor copolymer, a range of reaction temperatures and reaction times is possible. The reaction temperature is constrained mainly by the temperature range at which the solvent is liquid and typically varies from $-30°$ C. to $+70°$ C., preferably $-30°$ C. to $+30°$ C., more preferably $-5°$ C. to $+10°$ C. The reaction time may typically be between 1 minute and 1 day, depending on the temperature and reaction components, preferably not greater than 4 hours. Once the precursor copolymer is formed this may optionally be purified, for example by precipitation with a salt of a non-nucleophilic counter anion (i.e. anion exchange). Preferably the precursor copolymer is dialysed against an appropriate solvent such as water or a water-alcohol mixture. Choice of the base used in the reaction is not particularly critical provided that it is soluble in the solvent. Typical bases include hydroxides or alkoxide derivatives of Group I/II metals and may be present at a ratio of 0.7–1.3 mole equivalents of base per mole of monomer. Preferably, hydroxides of lithium, sodium or potassium are used in equimolar proportions with the monomer.

In a further embodiment, at least one of the monomer units of the copolymer comprises an arylene vinylene unit substituted with a solubilizing group in the arylene ring so as to render the copolymer soluble. Any known solubilizing group may be used for this purpose. Where the copolymer is to be soluble in water, a charged solubilizing group is preferred. The solubilizing group typically comprises an alkoxy group of at least 4 carbon atoms. The alkoxy group may be branched or linear and preferably introduces asymmetry into the arylene rings so as to disrupt the packing of the copolymer chains. Preferably the alkoxy group is a 2-methylpentyloxy or a 2-ethylhexyloxy group. A further alkoxy group such as a methoxy group may be substituted para to the solubilizing group.

By making the copolymer soluble, this confers the advantage of allowing the copolymer to be processed in solution. Accordingly, a solution-processable conjugated copolymer may be provided in which the monomer units have been selected to modulate the semiconductor bandgap thereof. In this way, the quantum efficiency of the copolymer can be increased and the wavelength of radiation emitted during luminescence can be selected.

In a further aspect, the present invention also provides a method of forming a conjugated poly(arylene vinylene) copolymer. The method comprises heating substantially in the absence of oxygen a poly(arylene-1,2-ethanediyl) precursor polymer wherein at least some of the ethane groups include a modifier group substituent, the heating conditions being controlled so that elimination of the modifier group substituents occurs to form the copolymer whereby a proportion of the vinylic groups of the copolymer remain saturated by the modifier group substituents, the proportion of saturated vinylic groups controlling the extent of conjugation in the copolymer, thereby modulating the semiconductor bandgap of the copolymer.

In this aspect of the invention, the precursor polymer is formed whereby substantially all the leaving groups are replaced by the modifier groups. A suitable method for forming the precursor polymer is to be found in Tokito et. al Polymer (1990), vol. 31, p.1137. By replacing the leaving group with a modifier group which is substantially stable at ambient temperatures, a relatively robust precursor polymer is formed. Examples of typical modifier groups are set out in the foregoing discussion. Advantageously the modifier group is an alkoxy group, preferably a methoxy group.

ture of heating and the time of heating it is possible to control the degree of conversion into the copolymer, thereby modulating the semiconductor bandgap of the copolymer. Thus, the wavelength of radiation emitted during luminescence of the materials may be selected by controlling the heating conditions. The more conversion to the conjugated copolymer, the more red-shifted the wavelength becomes. In this way, it is possible to control the colour of the emissions from blue to red. Preferably, the temperature of heating is in the range 200°–300° C. and preferably the heating time is up to 12 hours.

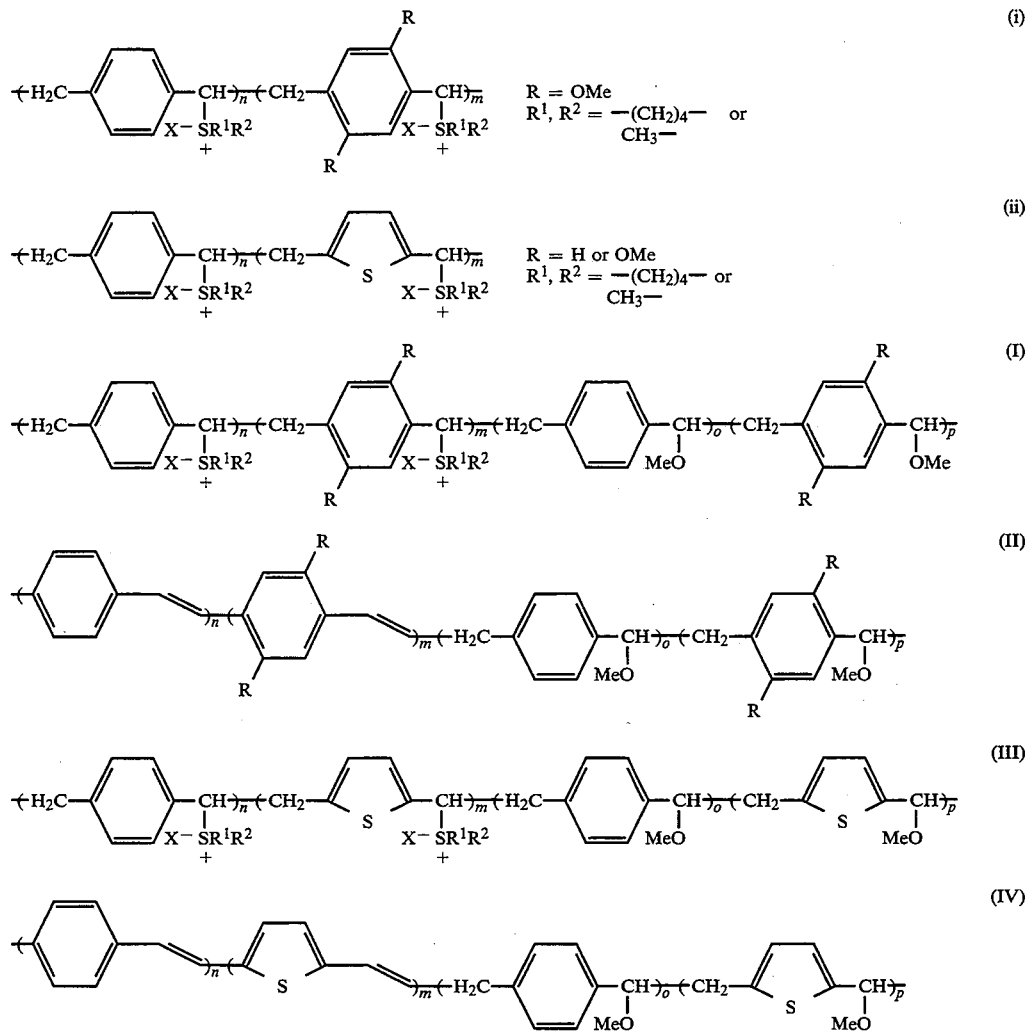

Advantageously the precursor polymer comprises a homopolymer, preferably a poly(paraphenylene-1,2-ethanediyl) polymer, a poly(2,5 dimethoxy para phenylene-1,2-ethanediyl) polymer, or a poly(thienylene-1,2-ethanediyl) polymer. Partial elimination of the modifier groups from the homopolymer produces a copolymer.

By controlling the extent of conversion to the copolymer, the extent of conjugation in the copolymer is controlled. This therefore provides a further route for modulating the semiconductor bandgap of the copolymer. The heating of the precursor polymer is preferably performed substantially in the absence of acid. The presence of acid tends to result in conversion to the fully conjugated polymer. By controlling the tempera- Referring to the foregoing page of structural formulae, copolymers of type (i) have been prepared by Lenz et al from the tetrahydrothiophenium salts of the two monomer units as described in "Highly conducting, iodine-doped copoly(phenylene vinylene)s", C.-C. Han, R. W. Lenz and F. E. Karasz, Polym. Commun. 28, 261 (1987) and "Highly conducting, iodine-doped arylene vinylene copolymers with dialkoxyphenylene units", R. W. Lenz, C.-C. Han and M. Lux, Polymer 30, 1041 (1989). Copolymers of type (ii) have been prepared by Lenz et al from the tetrahydrothiophenium salts of the two monomer units as described in "Synthesis and electrical conductivity of poly ( 1,4 -phenylenevinylene-co-2,5-thienylenevinylene)" H.—K. Shim, R. W. Lenz and J.-I. Hin, Macromol. Chem 190, 389 (1989) and have been mentioned by K. Y. A. Jen, R. L. Elsenbaumer, L. W. Shacklette (Allied Corp.), PCT Int. Appl. Pub. No. WO 8800954. These copolpers were produced as intermediate products to the final products prepared by Lenz, these final products being heavily doped with strong oxidants to enable conductivity measurements to be undertaken. The intermediate products were not of interest themselves.

Furthermore, they were prepared under aqueous reaction conditions. Direct comparison of the materials prepared in Lenz et al and the materials prepared by the method of the preferred embodiments of the present invention showed that they were different for a number of reasons.

First, the use of water/alcohol mixtures as a solvent allows better control over the relative proportions of fragments of each monomer observed in the final co-polymers. This is observed by IR spectroscopy and micro-analysis.

Second, the use of water/alcohol in the present process allows selective substitution of the sulphonium leaving group with the alcohol. This occurs at a faster rate at benzylic carbons which are attached to an activated phenylene ring, for example, a dimethoxy substituted phenylene ring. This option is not open to the Lenz process. Evidence for substitution comes from nuclear magnetic resonance (NMR), infrared (IR), and photoluminescence studies and also from reactions observed on the homopolymers. For example, dimethoxy-PPV is prepared from a precursor polymer which has methoxy modifier groups. This polymer is in turn prepared according to the literature (T. Momii, S. Tokito, T. Tsutsui and S. Saito—Chem. Letters (1988), 1201) from the precursor polymer which has sulphonium leaving groups by exchanging the chloride anion with a p-toluenesulphonate anion and then reacting this material with methanol. It has been observed by the inventors that it is not necessary to exchange anions for the substitution reaction to occur in the dimethoxy-PPV precursor polymer. It has also been found by the inventors that the reaction of the sulphonium precursor polymer of PPV with methanol occurs at a much slower rate. The precursor co-polymers prepared by the method of the preferred embodiments of the present invention can therefore be better described by the structures of General Formulae (I) and (III).

Third, the usual method of conversion of precursor polymers with methoxy modifier groups is by heating under acidic conditions. With the method of the present invention it is preferred to use heat treatment alone as this allows the methoxy modifier groups to remain in part uneliminated thus segregating the conjugated material into discrete segments as described by General Formulae II and IV. This solution and method represents a significant advancement over the art. Thin films prepared by this method are stable to the loss of the methoxy modifier groups (for example, thin films heated for 2 h had similar properties to thin films heated for 24 h). This is evidenced by IR and ultraviolet/visible (UV/vis) spectroscopy.

Fourth, the use of water/alcohol mixtures increases the reaction rate of both monomeric units compared with just using water as the solvent during polymerisation. This is evidenced by comparison of the amount of acid necessary to neutralise the remaining unreacted base in Example 1 and in the examples described by Lenz.

Finally, the quality of films cast from a methanol solution as opposed to an aqueous solution is far superior and easily reproducible, and gives higher light output in electroluminescent devices. The quality of films was determined by Dek Tak profilometry.

In the following when reference is made to ratios of PPV, dimethoxy-PPV, PTV, dimethyl-PPV 2-methoxy-5-(2'methylpentyloxy)-PPV and 2-methoxy-5-(2'-ethylhexyloxy)-PPV monomer units in both precursor and conjugated copolymer structures the ratios are defined by the amounts of the corresponding monomer units used in the initial polymerisation reaction.

For a better understanding of the present invention and to show how the same may be carried into effect, reference will now be made by way of example to the accompanying drawings.

BRIEF DESCRIPTION OF THE DRAWINGS

FIG. 2a is a graph showing the absorption spectra of spin-coated thin films of PPV and copolymers of PPV, as the majority constituent, and dimethoxy-PPV (DMeOPPV) as converted at 220° C. in vacuo for 2 hours Curve a is PPV homopolymer
Curve b is 95% PPV to 5% DMeOPPV
Curve c is 90% PPV to 10% DMeOPPV
Curve d is 85% PPV to 15% DMeOPPV
Curve e is 80% PPV to 20% DMeOPPV
Curve f is 70% PPV to 30% DMeOPPV FIG. 2b is a graph showing the absorption spectrum of a spin-coated thin film of dimethoxy-PPV as converted at 220° C. in the present of acid for two hours.

FIGS. 10a, 11a and 12a are graphs showing the current/voltage characteristics of a thin film of respectively PPV; a copolymer produced from a 9:1 molar ratio of PPV and dimethoxy PPV monomer units respectively; and a copolymer produced from a 9:1 molar ratio of PPV and thienylene vinylene monomer units respectively, the polymer films being spin-coated and converted at 220° C. for two hours in vacuo with hole injecting electrodes of oxidised aluminium, and with electron injecting electrodes of aluminium;

FIGS. 10b, 11b and 12b are graphs showing the luminescence/current relationship for a thin film of respectively PPV; a copolymer produced from a 9:1 molar ratio of PPV and dimethoxy PPV monomer units respectively; and a copolymer produced from a 9:1 molar ratio of PPV and thienylene vinylene monomer units respectively, the polymer films being spin-coated and converted at 220° C. for two hours in vacuo with hole injecting electrodes of oxidised aluminium, and with electron injecting electrodes of aluminium;

A film of copolymer of 10% DMeOPPV: 90% PPV was spin-coated and an area was capped with 500A of evaporated aluminium. The sample was then thermally converted for 12 hours at 220° C. in vacuo. The aluminium capping layer was removed by reacting it in dilute alkali. FIGS. 16 and 17 show the optical absorption spectra and photoluminescent spectra for two areas in a polymer film which have undergone different conversion treatments;

FIGS. 28a and 28b are graphs showing the electroluminescence spectra for random copolymers of PPV and MEH-PPV produced from 20:80 and 5:95 w/w ratios of PPV and MEH-PPV monomer units, respectively;

Figure 33:
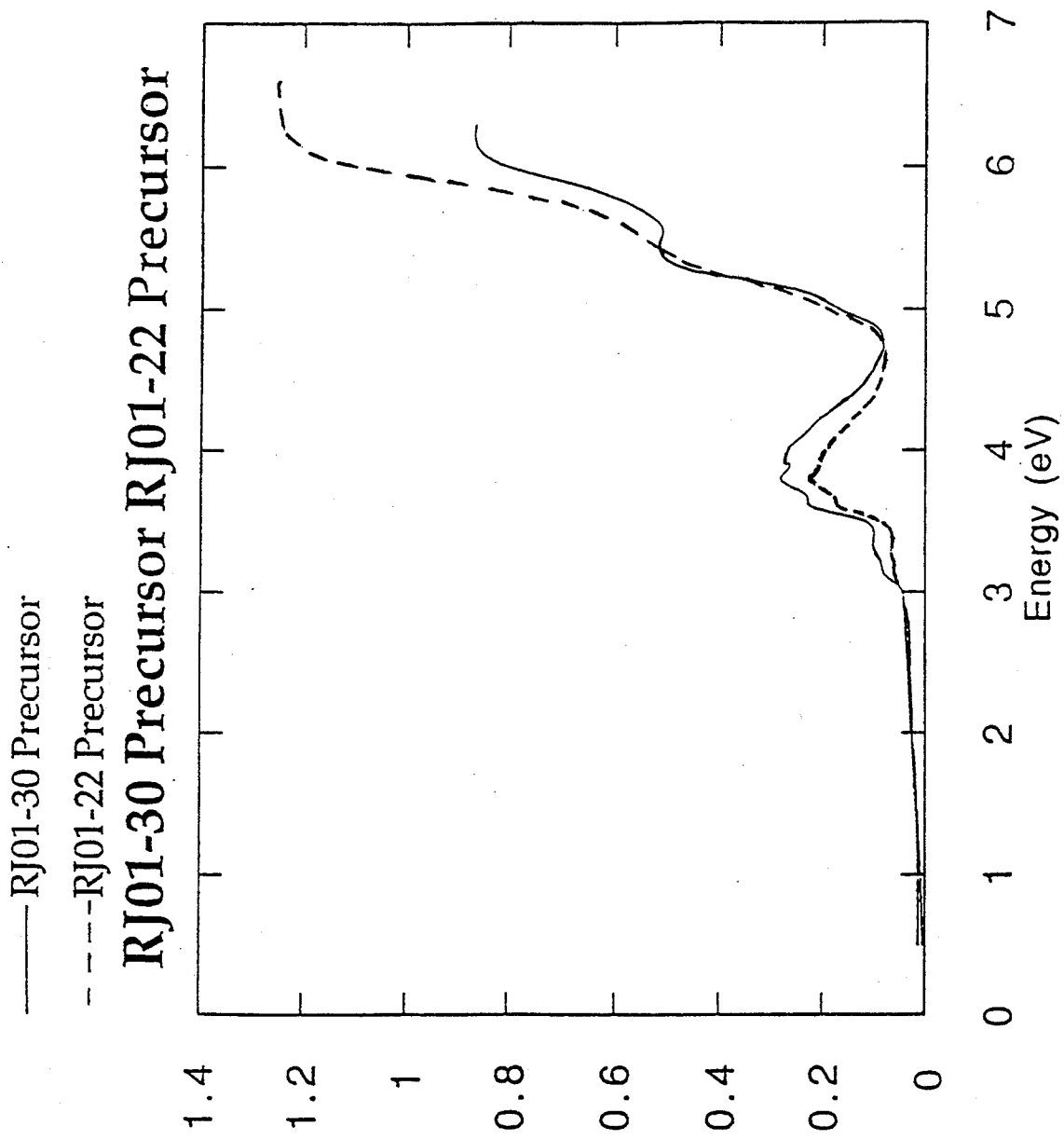
Figure 34:
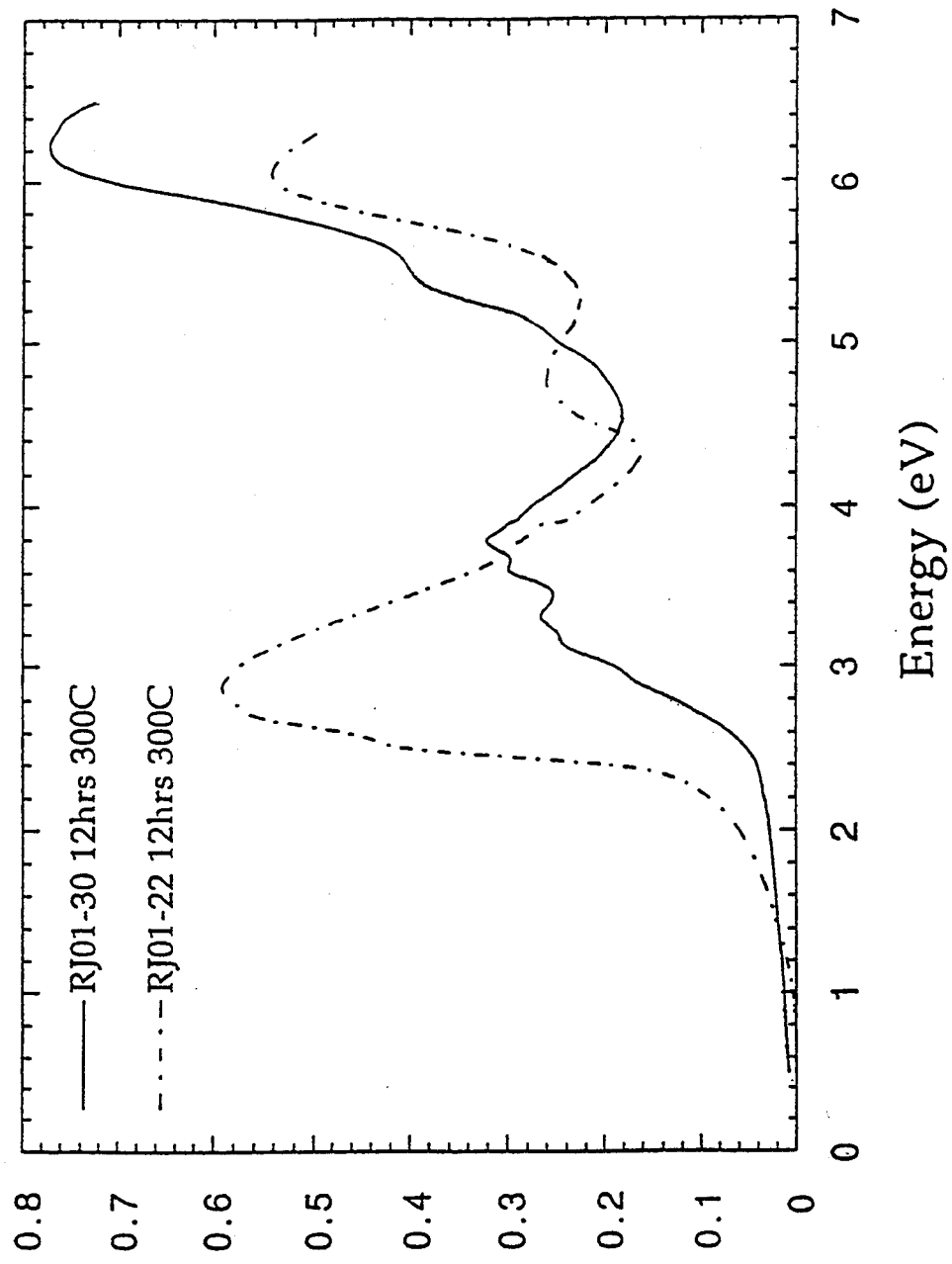
Figure 35:
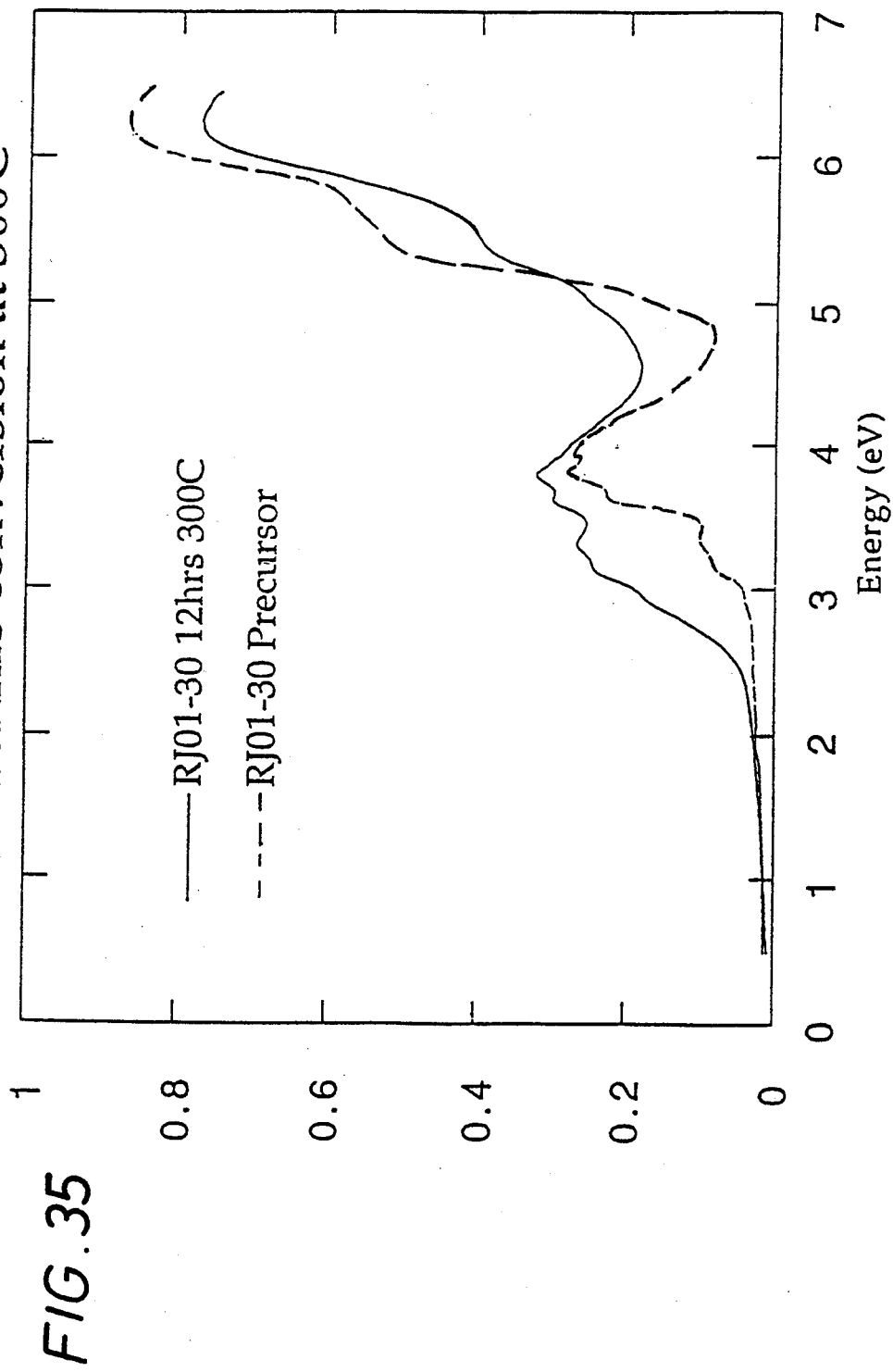
Figure 37:
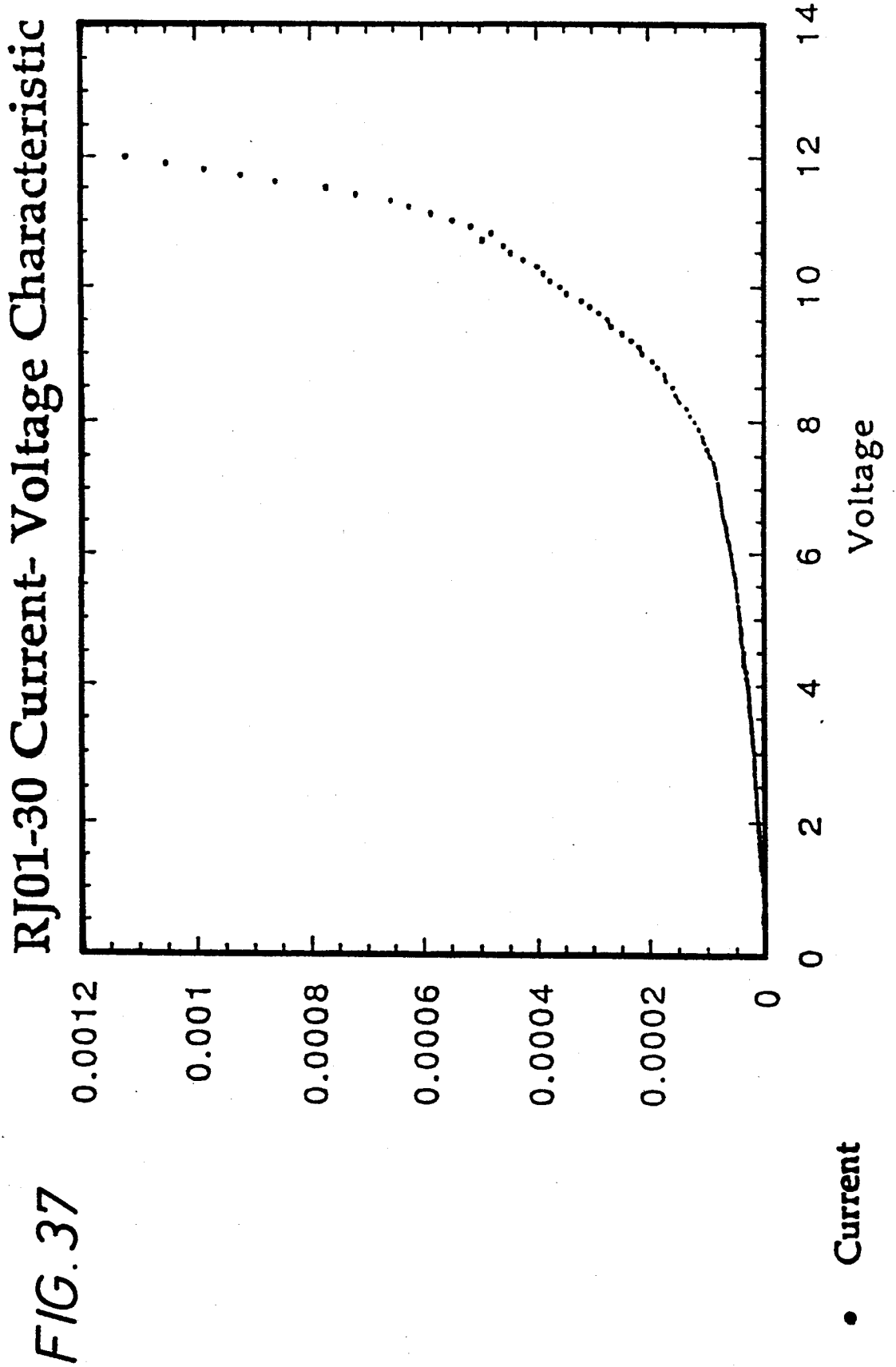
Figure 38:
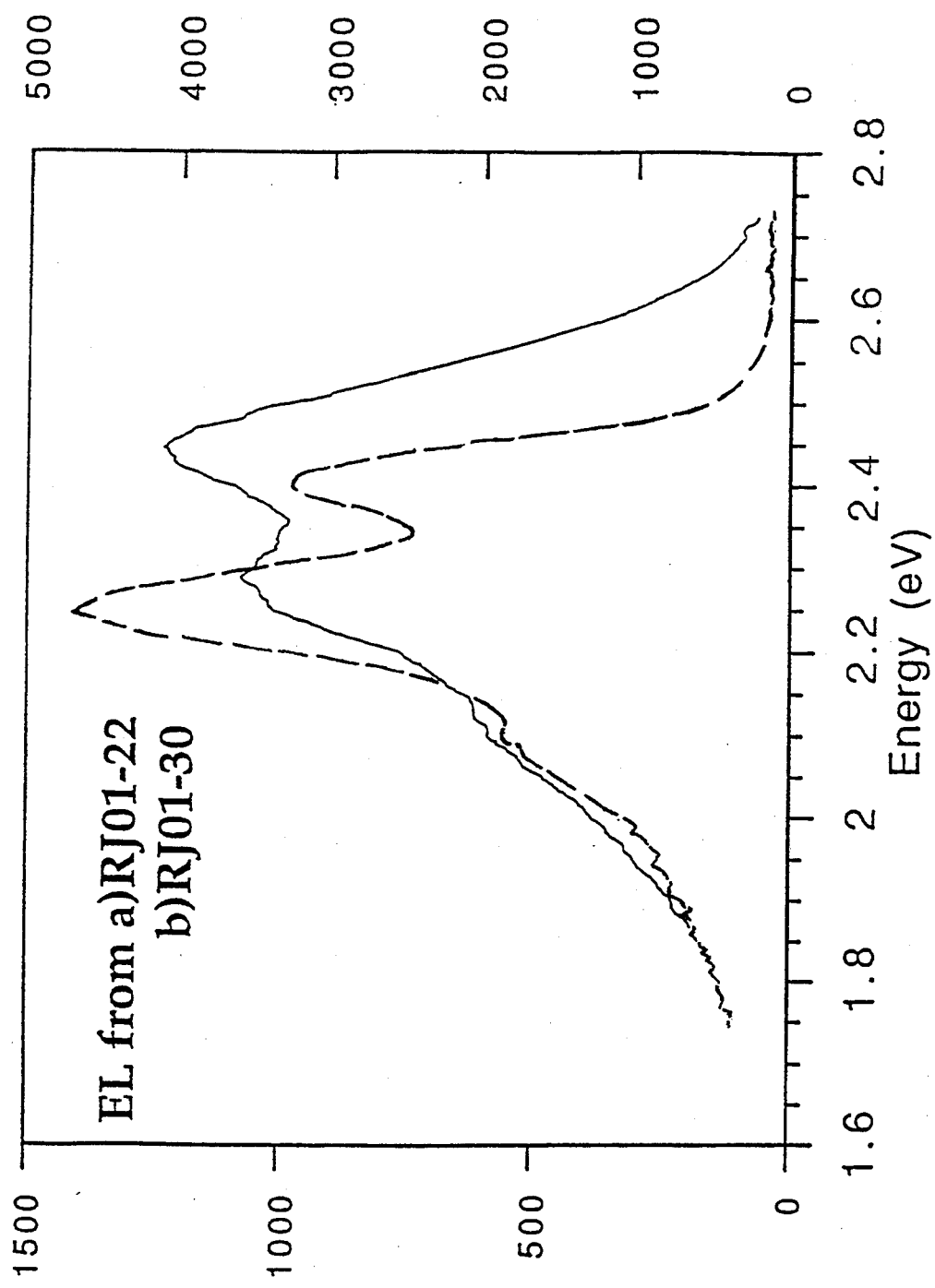
Figure 39:
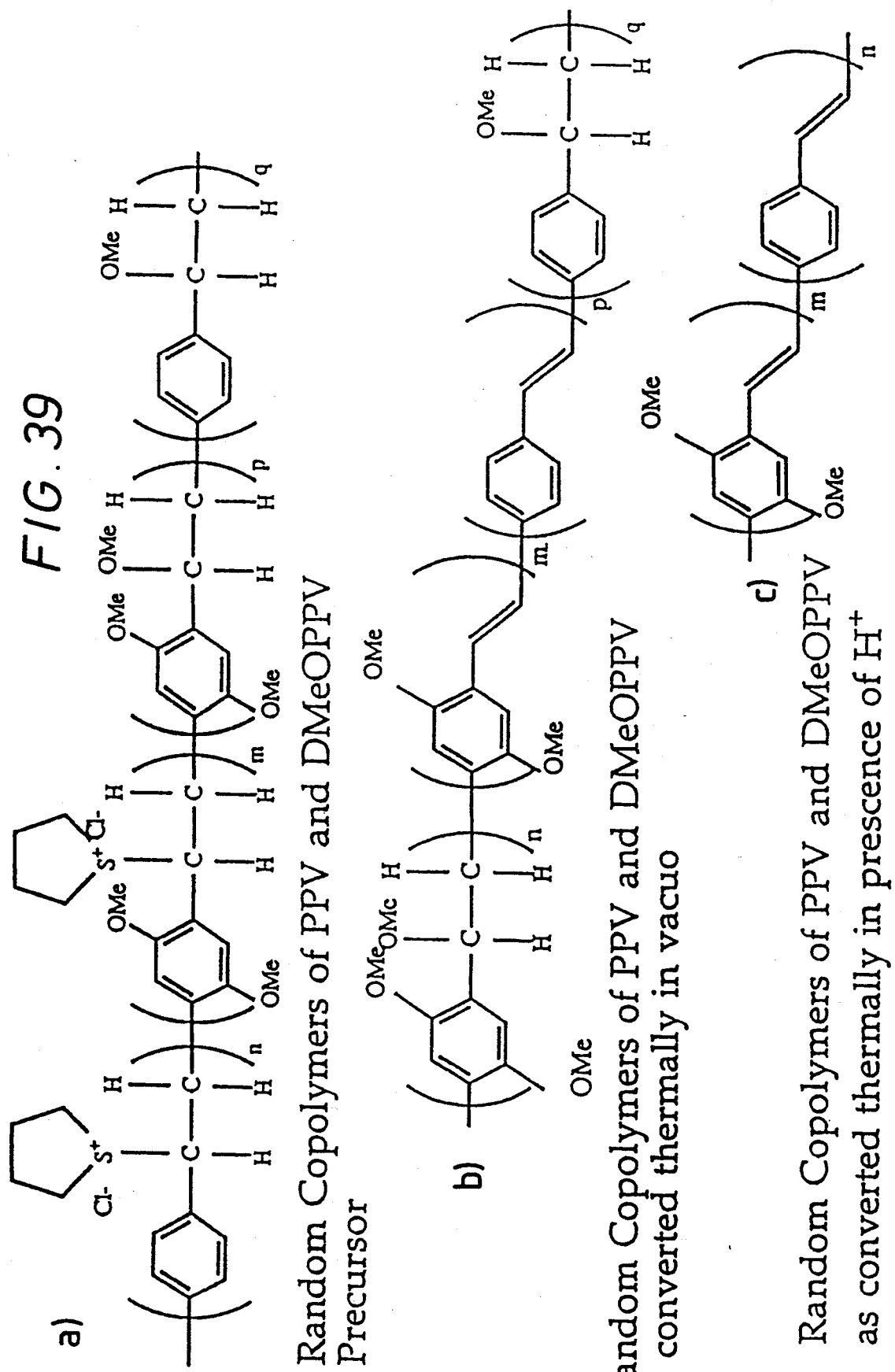
Figure 40:
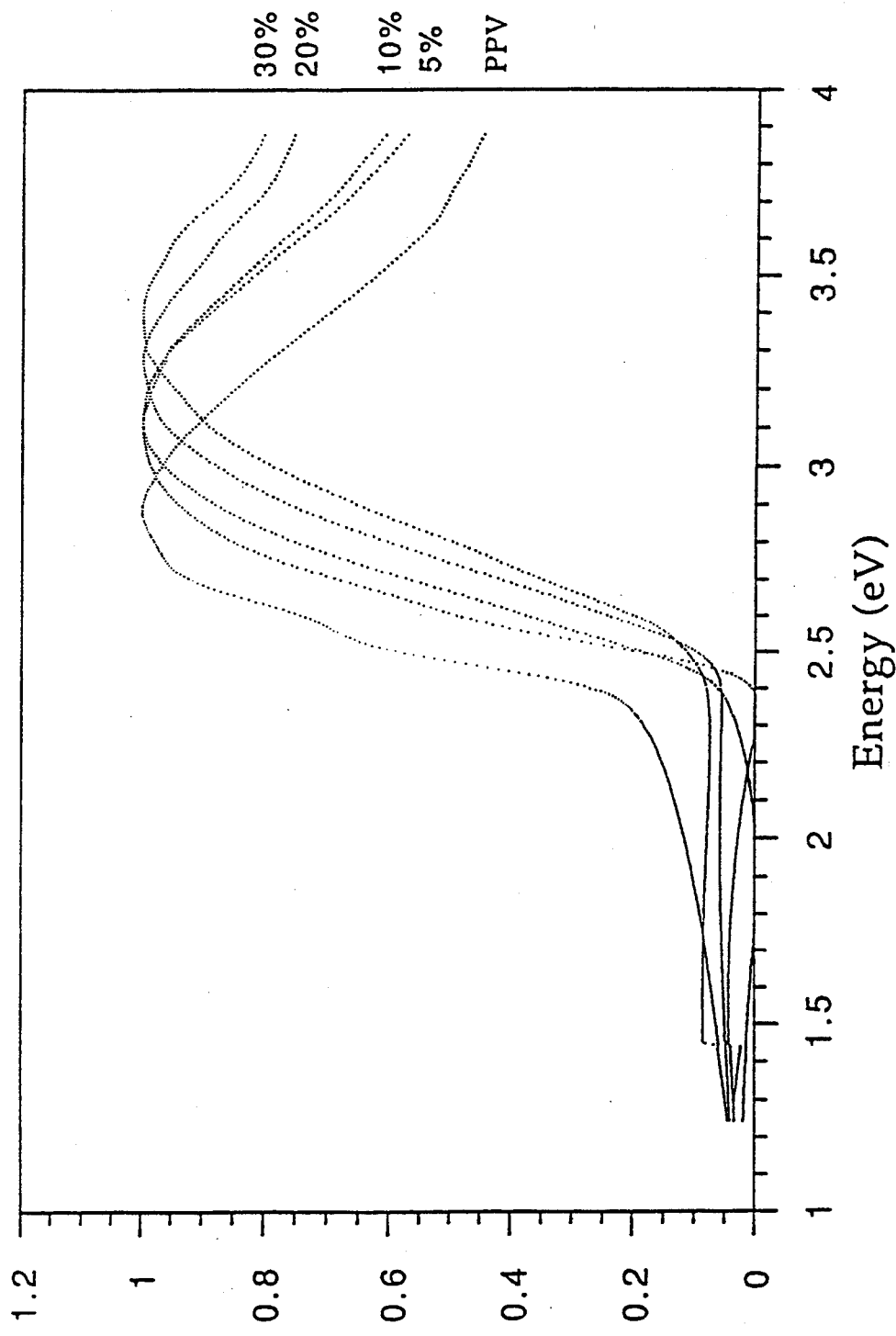
Figure 41:
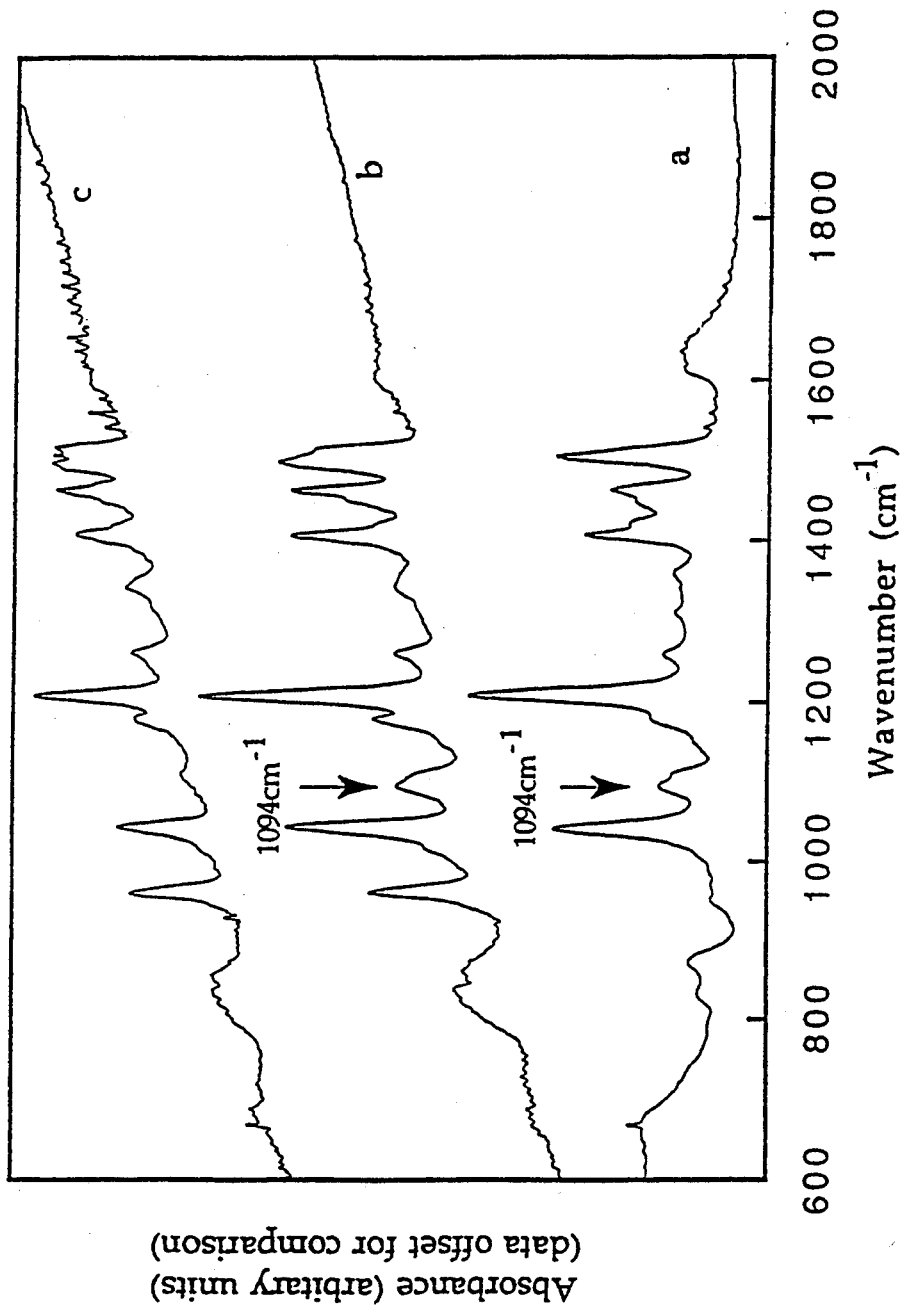

80:20 w/w ratios of MEH-PPV and PPV monomer units, respectively;

FIGS. 32 (a to d) show respectively the formal structural formulae of: the THT-leaving PPV precursor; the MeO-leaving PPV precursor; PPV; and partially converted MeO-leaving PPV;

FIG. 33 is a graph showing the absorption spectra of precursors of THT-leaving PPV (broken) and MeO-leaving PPV (solid);

FIG. 34 is a graph showing the absorption spectra of THT-leaving PPV (broken) and MeO-leaving PPV (solid) after thermal conversion at 300° C. for 12 hours in vacuo;

FIG. 35 is a graph showing the absorption spectra of thin spin-coated films of MeO-leaving PPV before (dotted) and after (solid) thermal conversion at 300° C. for 12 hours in vacuo;

FIGS. 36 (a) and (b) are graphs showing respectively the current-voltage and luminance-current characteristics of THT-leaving PPV as converted in vacuo at 220° for 12 hours on a substrate of ITO-coated glass and with aluminium as a cathode;

FIG. 37 shows the current-voltage and luminance-current characteristics of MeO-leaving PPV as converted in vacuo at 300° for 12 hours on a substrate of ITO-coated glass and with aluminium as a cathode;

FIG. 38 is a graph showing the electroluminescence emission spectra of THT-leaving PPV (dotted) and MeO-leaving PPV (solid) after thermal conversion;

FIGS. 39 shows respectively the formal structural formulae of the random copolymers of: PPV and DMeOPPV in precursor form; as converted thermally in vacuo; and as converted thermally in the presence of acid;

FIG. 40 is a graph showing the absorption spectra of spin-coated thin films of random copolymers of PPV and DMeOPPV after thermal conversion as converted in vacuo at 220° C. for 12 hours. The percentages on the figure represent the percentage of DMeOPPV monomer units w/w from which the precursor was formed;

FIG. 41 is a graph showing the infra red absorption spectra of a 20% random copolymer of DMeOPPV and PPV in which:

Line a is the precursor

Figure 42:
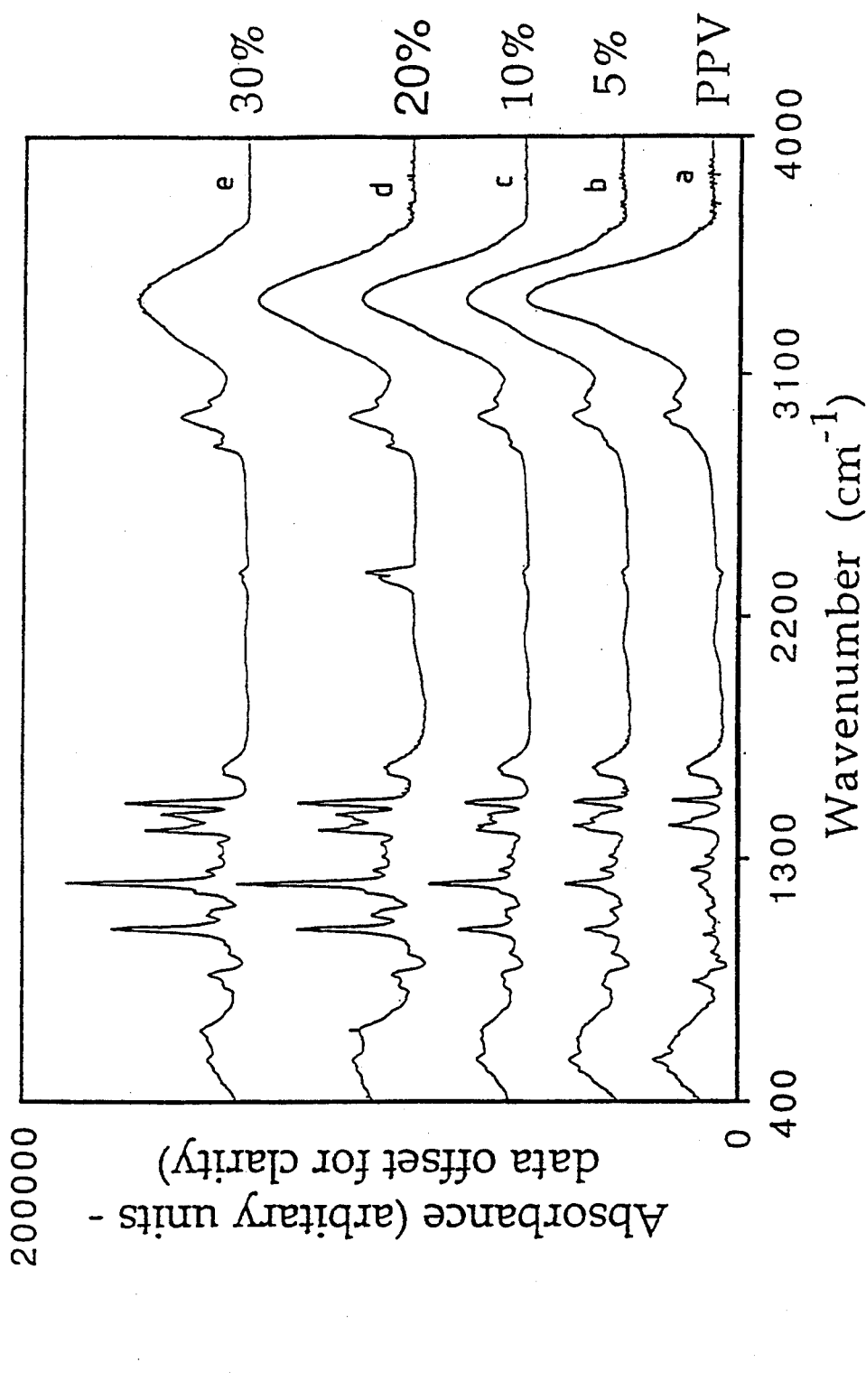
Figure 43:
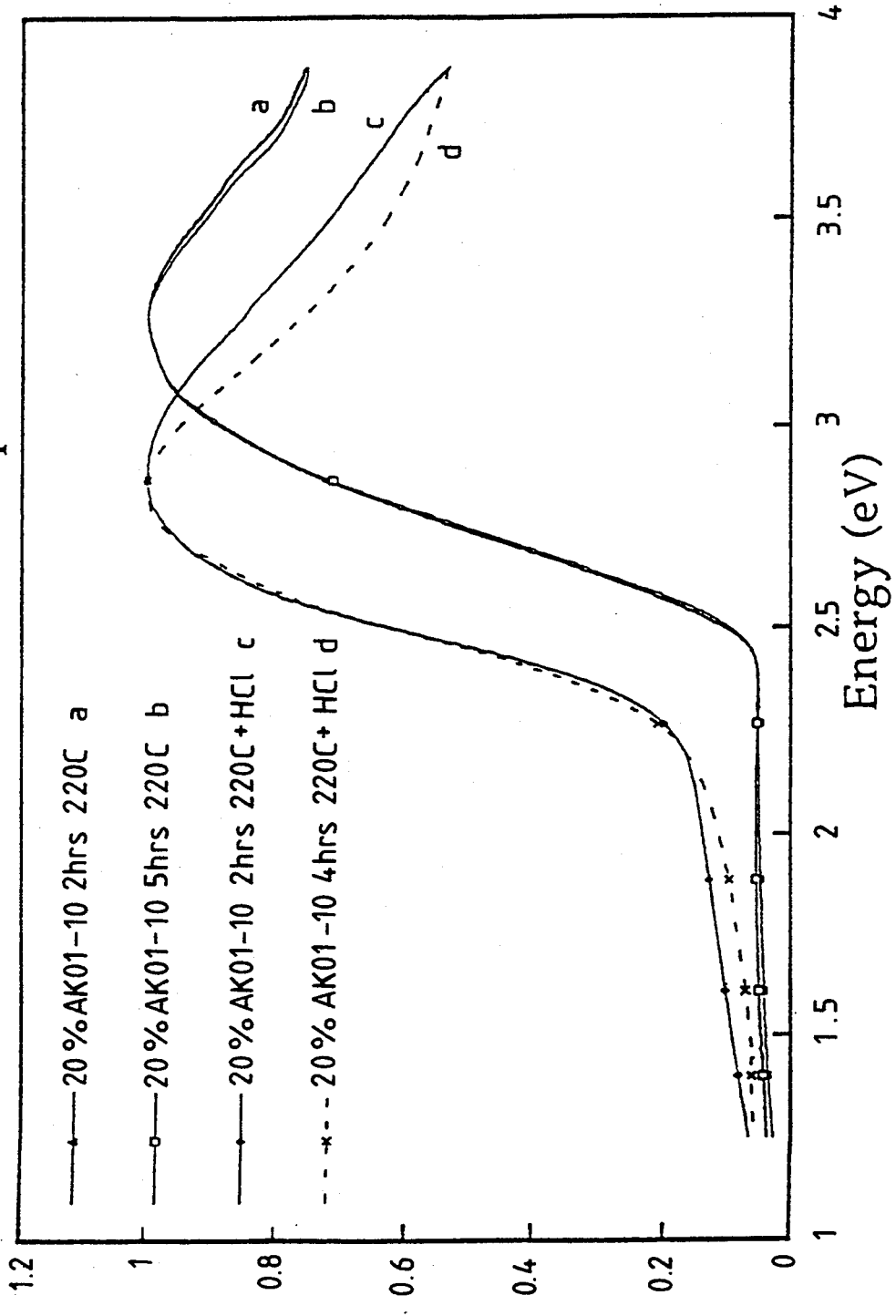
Figure 44:
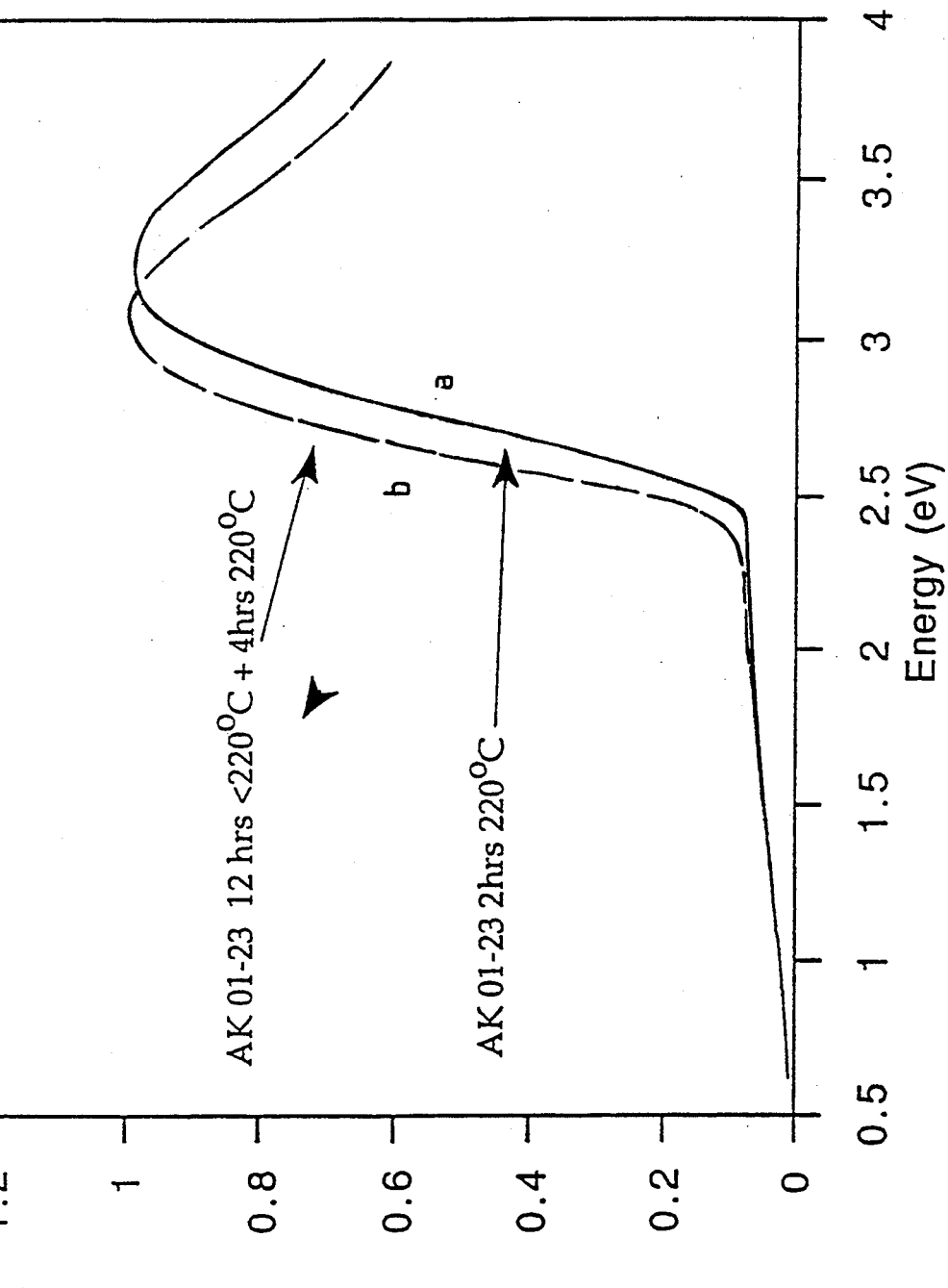
Figure 45:
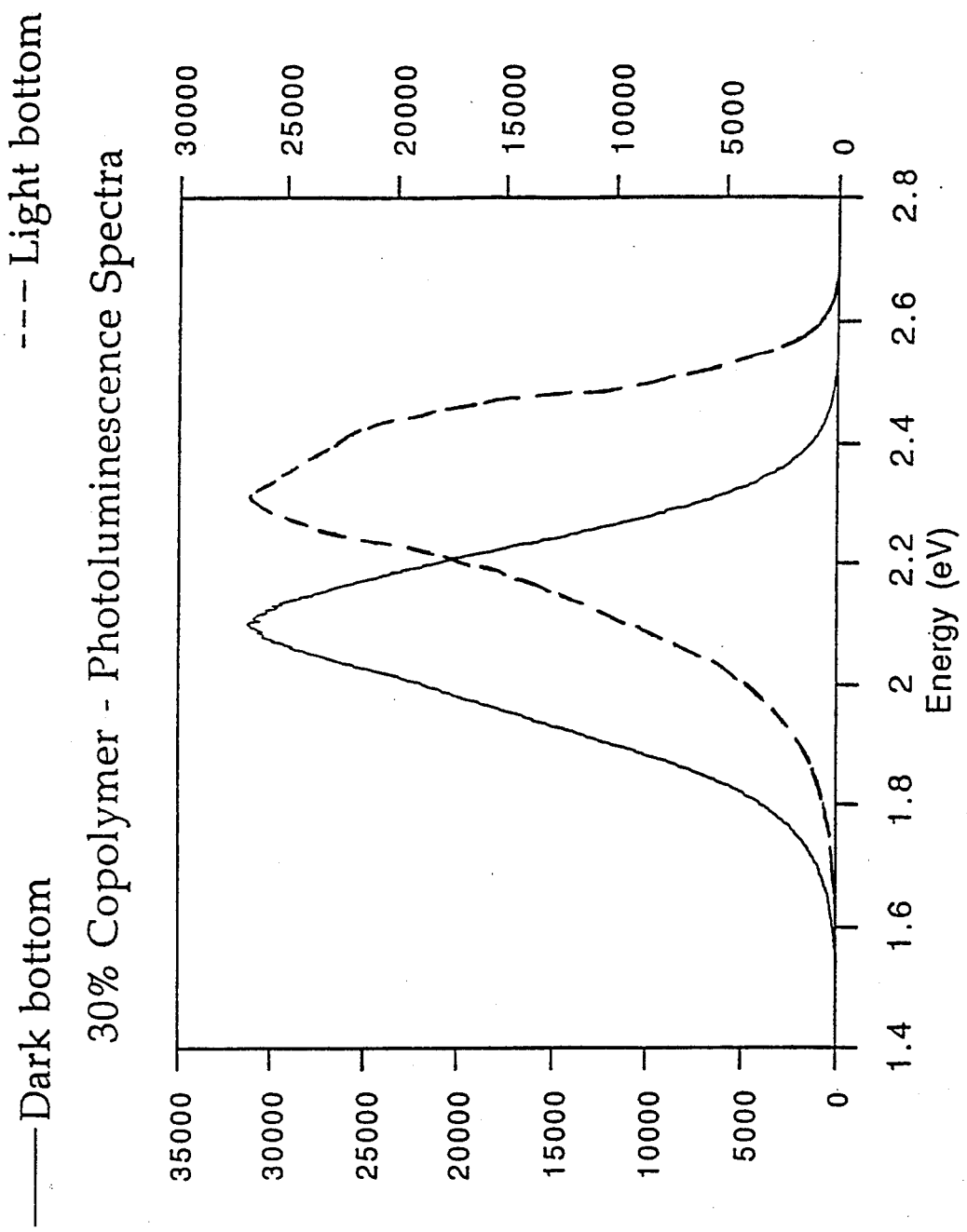
Figure 46:
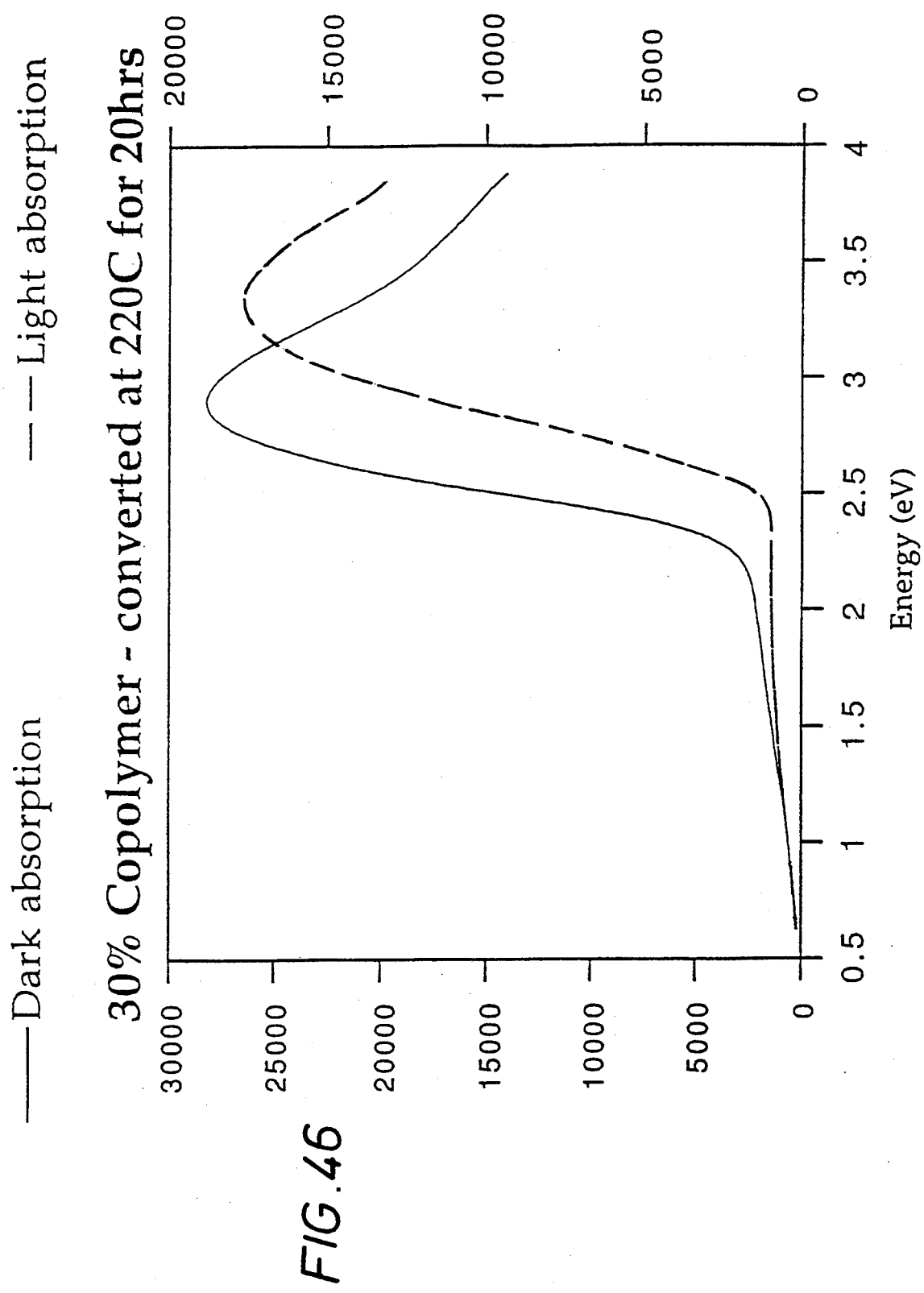
Figure 47:
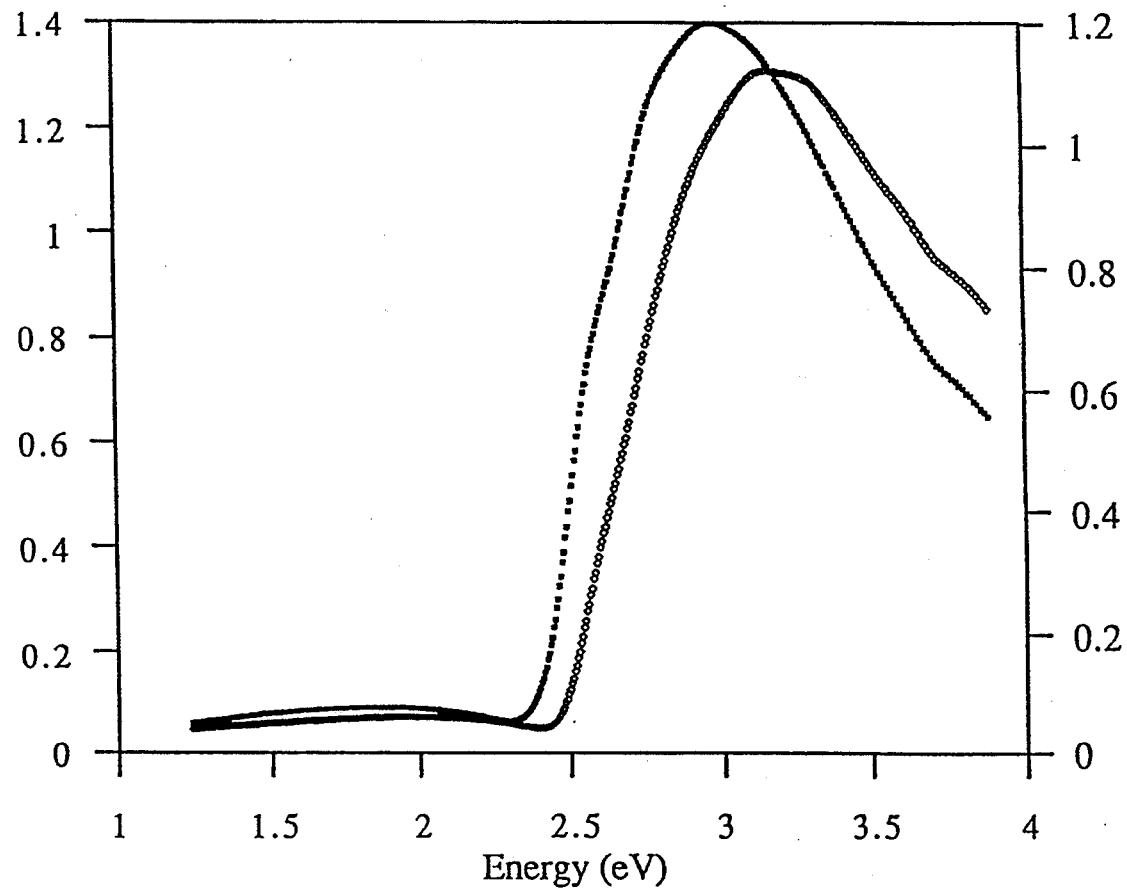
Figure 48:
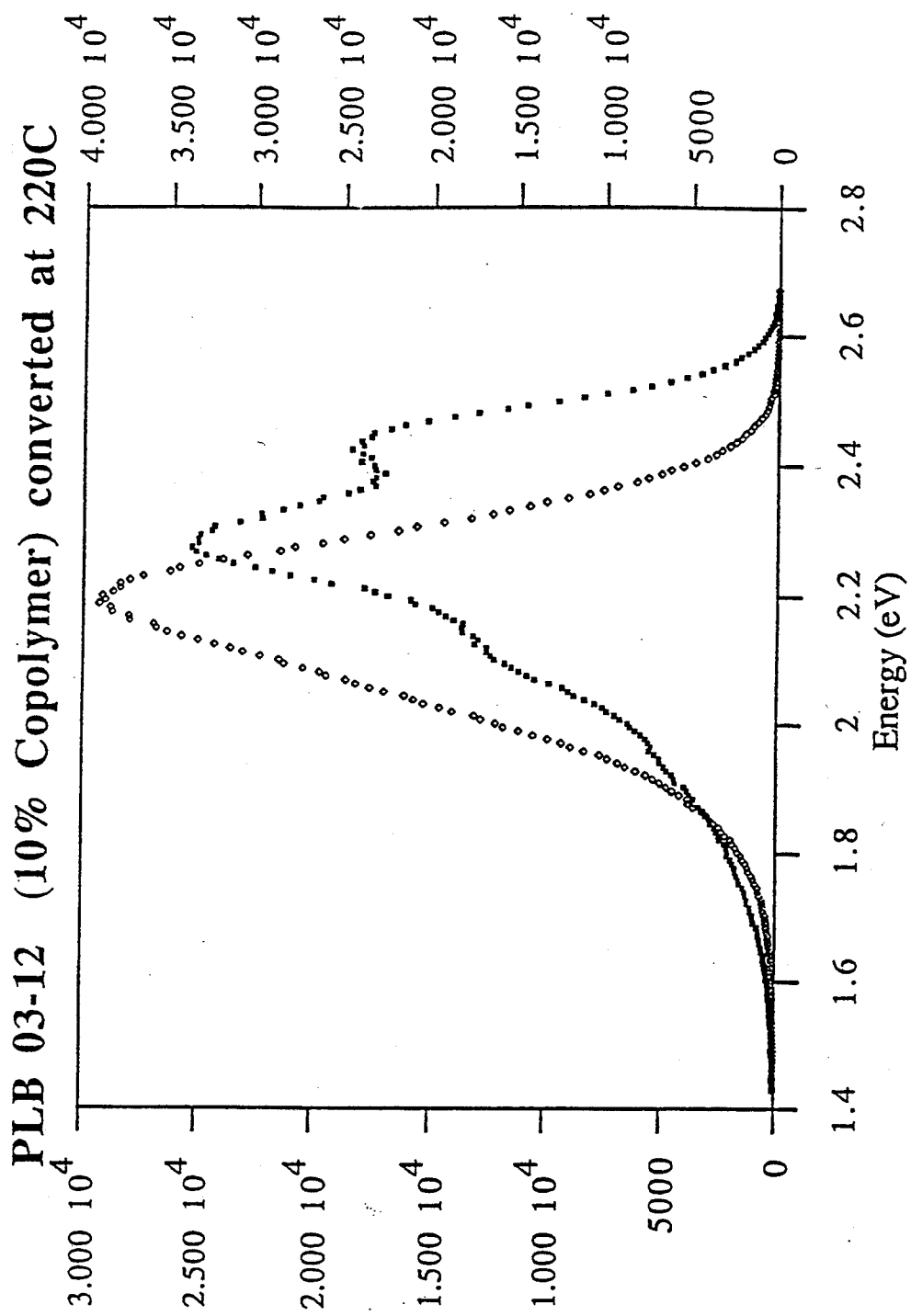

Line b is the copolymer spin-coated on KBr and converted at 220° in vacuo for two hours Line c is the same sample further converted for two hours at 220° C. in the presence of acid;

FIG. 42 is a graph showing respectively the infrared absorption spectra of PPV and the random copolymers of PPV, as the major constituent, and DMeOPPV produced from 95:5, 90:10, 80:20 and 70:30 molar ratios of PPV and DMeOPPV monomer units respectively;

FIG. 43 is a graph showing the absorption spectra of spin-coated thin films of a 20% random copolymer of DMeOPPV and PPV converted in vacuo (a,b) and in the presence of HCl (c,d);

FIG. 44 is a graph showing the variation of bandgap with different conversion conditions; the higher bandgap material (a) converted for 2 hours at 220° C. in vacuo, the lower bandgap material (b) converted for 12 hours at 100° C. in vacuo and subsequently four hours at 220° C. in a 15% random copolymer of DMeOPPV and PPV;

FIG. 45 is a graph showing the photoluminescence spectra of a 30% random copolymer of DMeOPPV and PPV;

FIG. 46 is a graph showing the photoluminescence emision spectra of a 30% random copolymer of DMeOPPV and PPV;

FIG. 47 is a graph showing the absorption spectra of capped and uncapped 10% random copolymers Of DMeOPPV and PPV; and FIG. 48 is a graph showing the photoluminescence emission spectra of capped and uncapped 10% random copolymers of DMeOPPV and PPV after thermal conversion.

In each of FIGS. 45 to 48, a film of copolymer were spin-coated and an area was capped with 500A of evaporated aluminium. The sample was then thermally converted for 12 hours at 220° C. in vacuo. The aluminium capping layer was removed by dissolving it in dilute alkali. The lower energy absorption and photoluminescence spectra are from the capped regions of polymer.

DESCRIPTION OF THE PREFERRED EMBODIMENTS

Figure 1:
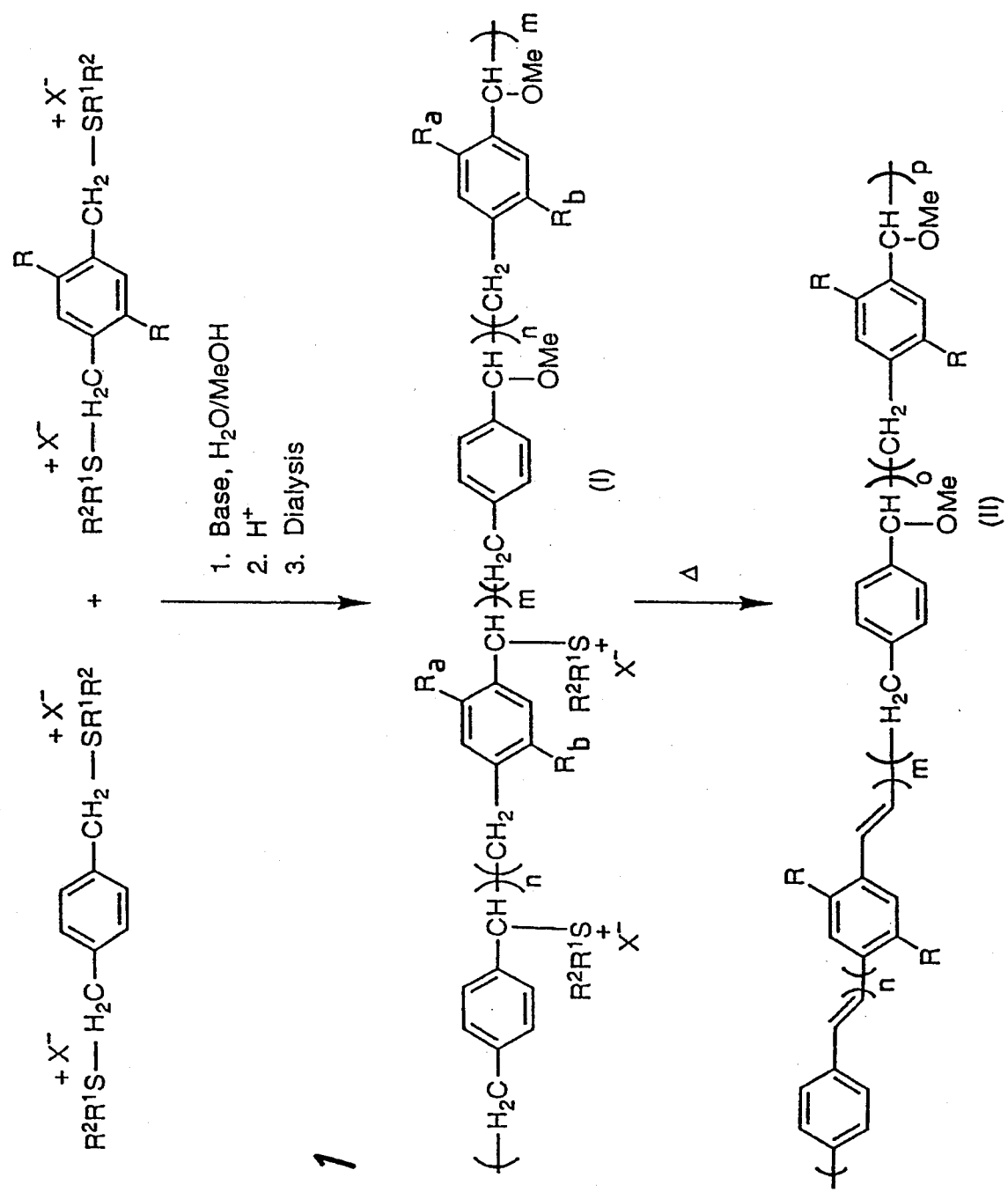
FIG. 1 is a diagram showing an example of the steps of a method for producing the copolymers prepared via a soluble precursor.

FIG. 1 illustrates in general terms a process for producing copolymers according to one embodiment of the invention. A mixture of two monomeric bis-sulphonium salts in a suitable solvent was polymerised by reaction with a base. The resultant soluble precursor copolymer was purified and then converted to a conjugated form by heat treatment.

Examples of both the precursor copolymers and the partially conjugated copolymers are shown in the foregoing formulae drawings. The compound of General Formula I represents a precursor copolymer of the compound of General Formula II, which is a poly(paraphenylene vinylene-co-2,5-disubstituted-para phenylene vinylene) copolymer. Similarly, the compound of General Formula III represents a precursor copolymer of the compound of General Formula IV, which is a poly(2,5-thienylene vinylene-co-disubstituted-para-phenylene vinylene) copolymer.

In these compounds the extent of conjugations will be determined by the values of n,m,o and p. Clearly, for a partially conjugated copolymer (II) or (IV), $o+p>1$, and so at least some of the vinylic groups will be saturated by inclusion of the modifier group represented by —OR'.

The present invention is concerned in one aspect with improving the efficiency of radiative decay of excitons by trapping them on local regions of the polymer chain, which have lower energy gaps and thus are regions of lower potential energy for the excitons, so that the excitons are confined for a long enough period that they will, decay radiatively. This has been achieved by the synthesis of a family of copolymers in which the units which make up the polymer chain are selected from two or more chemically different groups, which possess differing bandgaps in their respective homopolymers. Such polymers have been synthesised while still retaining all the desirable processing and materials properties of PPV. In the examples shown in this disclosure, paraphenylene vinylene is used as one of the components (usually the majority component) together with varying compositions of the following other components or their unconverted precursors, as discussed more fully below:

| | |
|---|---|
| 2,5-dimethoxy-para-phenylene vinylene (PDMOPV) | 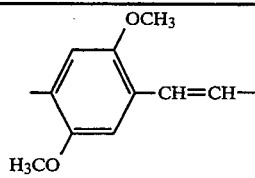 |
| 2,5-thienylene vinylene (PTV) | 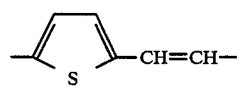 |
| 2,5-dimethyl-para-phenylene vinylene (PDMPV) | 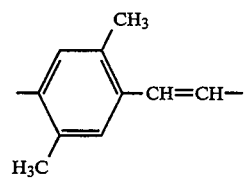 |
| 2-methoxy-5-(2'-methylpentyloxy)-para-phenylene vinylene (MMP—PPV) | 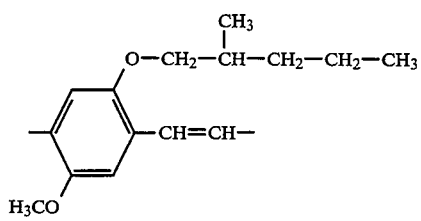 |
| 2-methoxy-5-(2'ethylhexyloxy)para-phenylene vinylene (MEH—PPV) | 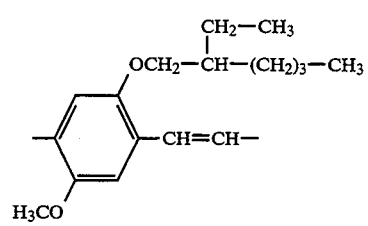 |

The first three of these components are available in the form of their corresponding homopolymers, and the first two possess an energy gap lower than that of PPV. PPV shows the onset of $\pi$ to $\pi^*$ optical transitions at 2.5 eV; poly(2,5-dimethoxy-para-phenylene vinylene), PDMOPV, at 2.1 eV and poly(2,5-thienylene vinylene), PTV, at 1.8 eV. It is expected, on the basis of the known inductive effects of its substituents, that poly(2,5-dimethyl-para-phenylene vinylene), PDMPV, will have a bandgap a little lower than that of PPV.

Dimethyl PPV (DMPPV) has a higher bandgap in its homopolymer than does PPV. This is contrary to the argument which runs that the methyl substituents have inductive effects and so will lower the bandgap of DMPPV over PPV. The true picture is that due to the steric interaction of the dimethyl groups, the polymer conjugated backbone is distorted decreasing the degree of electron delocalisation along the backbone and thus raising the bandgap with respect to PPV. This is evidenced in electron diffraction studies and quantum chemical calculations.

Thus, the copolymers of PPV and Dimethyl PPV as prepared via a THT leaving group (FIG. 8) have a controlled shift in bandgap not because the DMPPV units are saturated giving a copolymer of saturated and unsaturated units but because DMPPV and PPV have genuinely different bandgaps and we are forming a copolymer of the two. We evidence that there are no saturated units by an absence of 1094 cm$^{-1}$ stretch in the FTIR spectra of the precursors. Bandgap is still controllable hence by selection of the monomer units ratio.

There follows specific examples of processes in accordance with embodiments of the invention.

EXAMPLE 1

A mixture of $\alpha,\alpha'$-bis(tetrahydrothiophenium chloride)-p-xylene (0.97 g, 2.8 mmol) and $\alpha,\alpha'$-bis(tetrahydrothiophenium chloride)-2,5-dimethoxy-p-xylene (0.12 g, 0.3 mmol) in methanol (7.1 ml) was deoxygenated with nitrogen and cooled with an ice-bath. A nitrogen deoxygenated aqueous sodium hydroxide solution (0.4M, 2.9 mmol, 7.1 ml) was added dropwise and the reaction mixture was left to stir for 1 hour at 0° C. under inert atmosphere. The reaction was terminated by addition of hydrochloric acid (0.4M, 1.0 ml). The viscous solution was then dialyzed against deoxygenated distilled water (3×1000 ml) over 3 days using cellulose membrane dialysis tubing with a molecular weight cut-off of 12,400 (supplied by Sigma Chemical Company Limited, Dorset, U. K.). The solvent was completely removed in vacuo at room temperature from the material remaining in the dialysis tubing. The residue was dissolved in dry methanol (15 ml).

EXAMPLE 2

A mixture of $\alpha,\alpha'$-bis(tetrahydrothiophenium chloride)-p-xylene (0.91 g, 2.6 mmol) and $\alpha,\alpha'$-bis(tetrahydrothiophenium chloride)-2,5-dimethyl-p-xylene (0.10 g, 0.26 mmol) in methanol (9.5 ml) was deoxygenated with nitrogen and cooled with an ice-bath. A nitrogen deoxygenated ice-cold aqueous sodium hydroxide solution (0.4M, 2.9 mmol, 7.1 ml) was added dropwise and the reaction mixture Was left to stir for 1 hour at 0° C. under inert atmosphere. The reaction was terminated by addition of hydrochloric acid (0 4M, 0.5 ml). The viscous solution was then dialyzed against deoxygenated distilled water (3×1000 ml) over 4 days using cellulose membrane dialysis tubing with a molecular weight cut-off of 12,400 (supplied by Sigma Chemical Company Limited, Dorset, U. K.). The solvent was completely removed in vacuo at room temperature from the material remaining in the dialysis tubing. The residue was dissolved in dry methanol (10 ml).

EXAMPLE 3

A mixture of α,α'-bis(tetrahydrothiophenium chloride)-p-xylene (0.98 g, 2.8 mmol) and α,α'-bis(tetrahydrothiophenium chloride)-2-nitro-p-xylene (0 11 g, 0 33 mmol) in methanol (8.0 ml) was deoxygenated with nitrogen and cooled with an ice-bath. A nitrogen deoxygenated ice-cold aqueous sodium hydroxide solution (0.4M, 2.9 mmol, 8.0 ml) was added rapidly and the reaction mixture was left to stir for 3.5 hours at 0° C. under inert atmosphere. The reaction was terminated by addition of hydrochloric acid (0.4M, 1.0 ml). The viscous solution was then dialyzed against deoxygenated distilled water (3×1000 ml) over 4 days using cellulose membrane dialysis tubing with a molecular weight cut-off of 12,400 (supplied by Sigma Chemical Company Limited, Dorset, U. K.). The solvent was completely removed in vacuo at room temperature from the material remaining in the dialysis tubing. The residue was dissolved in dry methanol (4 ml).

EXAMPLE 4

Preparation of 1-methoxy-4-(2''-methylpentyloxy) benzene

Sodium metal (6.99 g, 304 mmol) was dissolved in dry methanol (120 ml) under Ar to give a 2.5M solution of sodium methoxide. A solution of 4-methoxyphenol (31.4 g, 253 mmol) in dry methanol (150 ml) was added and this mixture was heated to reflux for 30 min. After cooling to room temperature, a solution of 1-bromo-2-methylpentane (46.0 g, 279 mmol) in dry methanol (100 ml) was added. The mixture was then heated to reflux for 16 hours. The solvent was removed in vacuo, the residue dissolved in ether (200 ml), washed with dilute aqueous sodium hydroxide (250 ml) and water (500 ml), dried over $MgSO_4$ and concentrated in vacuo again. Distillation at 80° C./0.5 mm Hg afforded 14.0g (27%) 1-methoxy-4-(2'-methylpentyloxy)benzene, $^1H$ NMR (250.1 MHz, $CDCl_3$): δ=0.94(t,3 H) , 1.02 (d, 3 H), 1.16–1.56 (m, 4H), 1.93 (m, 1H), 3.64–3.82 (m, 2H), 3.77 (s, 3H), 6.81–6.89 (m, 4H), $^{13}C$ NMR (100.6 MHz, $CDCl_3$): δ=14.3, 17.0 (both $CH_3$), 20.1, 35.8 (both $CH_2$), 33.0 (CH), 55.7 ($OCH_3$), 73.9 ($OCH_2$), 114.6, 115.4 (arom. CH), 153.5, 153.6 (ipso C). IR(film): 2956(m) , 1509(s), 1232(s) , 1045(m), 824(m) cm$^{-1}$, MS(EI): m/z (%)=208 (100), 124 (32), Calcd. for $C_{13}H_{20}O_2$: C 74.96,H 9.68 found: C 75.03,H 9.70.

EXAMPLE 5

Preparation of 1,4-bis(chloromethyl)-2-methoxy-5-(2'-methylpentyloxy)benzene

A mixture of hydrochloric acid (37%, 59 ml), formaldehyde (39%, 35 ml), 1-methoxy-4-(2'-methylpentyloxy)benzene (14.0 g, 67.4 mmol) and dioxane (100 ml) was saturated with hydrogen chloride for 15 min at 0° C. and stirred for 1.5 hours at room temperature. Another 30 ml of formaldehyde was then added at 0° C. and hydrogen chloride was bubbled through the reaction mixture for 10 min. After stirring for 16.5 hours at room temperature, the mixture was heated to reflux for 4 hours. The solvents were then completely removed to give a colourless solid residue which was dissolved in a minimum amount of hot hexane (50 ml). This solution was poured into ice-cold methanol (300 ml). The precipitate was filtered under suction and dried to afford 15.5 g (75%) of 1,4-bis(chloromethyl)-2-methoxy-5-(2'-methylpentyloxy)benzene, m.p. 78°–80° C. $^1H$ NMR (250.1 MHz, $CDCl_3$):=0.92( t, 3H), 1.04 (d, 3H), 1.22-1.55 (m, 4H), 1.95-2.05 (m, 1H), 3.73–3.90 (m, 2H), 3.85 (s, 3H), 4.62 (s, 2H), 4.64 (s, 2H), 6.89 (s, i H), 6.92 (s, 1 H). $^{13}C$ NMR (100.6 MHZ, $CDCl_3$):=14.3, 17.1 (both $CH_3$), 20.0, 35.7 (both $CH_2$), 33.0 (CH), 41.3, 41.4 (both $CH_2Cl$), 56.3 ($OCH_3$), 73.9 ($OCH_2$) 113.3, 114.1 (arom. CH), 126 8, 127 0, 150.8, 150.9 (ipso C) IR (KBr): 2958 (m), 1517 (s), 1466 (m), 1414 (s), 1263 (s), 1230 (s), 1036 (s), 734 (s) , 696 (s) cm$^{-1}$ MS(EI): m/z (%)=304 (18), 220 (38), 84 (41). Calcd. for $C_{15}H_{22}Cl_2O_2$: C 59.02,H 7.26; found: C 58.14,H 6.97.

EXAMPLE 6

Preparation of α,α'-bis(tetrahydrothiophenium chloride)-2-methoxy-5-(2'-methylpentyloxy)-p-xylene Tetrahydrothiophene ( 20.9 ml, 237 mmol) was added to a suspension of 1,4-bis (chloromethyl)-2-methoxy-5-(2'-methylpentyloxy)benzene (14.5 g, 47.3 mmol) in dry methanol ( 200 ml ) . The solid dissolved to form a clear solution within 10 min. This solution was then heated to 50° C. for 17 hours. The solvent was completely removed in vacuo, the residue treated with dry acetone, then filtered under suction and dried to give 12.7 g (56%) of α,α'-bis(tetrahydrothiophenium chloride)-2-methoxy-5-(2'-methylpentyloxy)-p-xylene. $^1H$ NMR (250.1 MHz, $CD_3OD$): δ=0.97(t, 3H), 1.10 (d, 3H), 1.26-1.61 (m, 4 H), 2.04 (m, 1H), 2.23–2.53 (m, 8H), 3.55 (br. m, 8H), 3.86–4.05 (m, 2H), 3.97 (s, 3 4.56 (s, 2H), 4.57 (s, 2 H), 7.35 (s, 1H), 7..37 (s, 1H). $^{13}C$ NMR (100.6 MHz, $CD_3OD$): δ=14.7, 17.5 ($CH_3$), 21.1, 29.7, 29.8, 34.3 ($CH_2$), 36.9 (CH), 43.1, 43.2, 44.5, 44.6, 44.8 ($CH_2$), 57.1 ($OCH_3$), 75.8 ($OCH_2$), 116.5, 117.3 (atom. CH), 121.3, 121.6, 153.0, 153.3 (ipso C). IR (KBr): 2953 (s), 1514 (s), 1404 (s), 1230 (s), 1033 (s) cm$^{-1}$.

EXAMPLE 7

Figure 18:
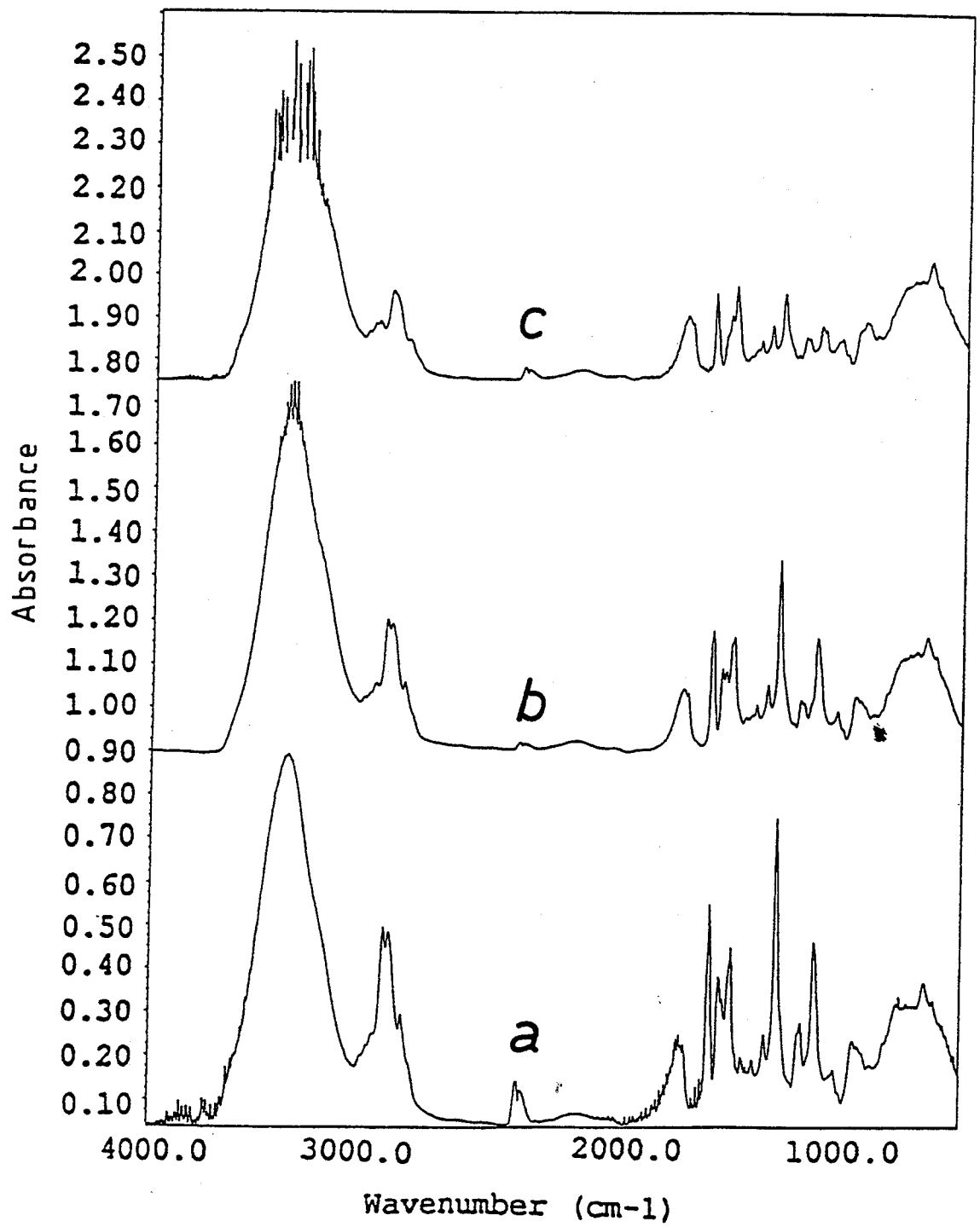
FIG. 18 is a graph showing the infrared spectra of precursor to random copolymers of PPV and MMP-PPV(2-methoxy-5-(2'-methylpentyloxy)-PPV produced from 80:20, 90:10, and 95:5 w/w ratios of PPV and MMP-PPV monomer units, respectively.

A mixture of α,α'-bis(tetrahydrothiophenium chloride)-p-xylene (0.90 g, 2.6 mmol) and α,α'-bis(tetrahydrothiophenium chloride)-2-methoxy-5-(2'-methylpentyloxy)-p-xylene (0.10 g, 0.21 mmol) in methanol (10 ml) was deoxygenated with argon and cooled with an ice-bath. An argon deoxygenated ice-cold aqueous sodium hydroxide solution (0.4M, 2.6 mmol, 6.9 ml ) was added dropwise and the reaction mixture was left to stir for 1 hour at 0° C. under inert atmosphere. The reaction was terminated by addition of hydrochloric acid (0.4M, 3.0 ml). The viscous solution was then dialyzed against deoxygenated distilled water (3×2000 ml) over 3 days using cellulose membrane dialysis tubing with a molecular weight cut-off of 12,400 (supplied by Sigma Chemical Company Ltd., Dorset, U. K.). The solvent was completely removed in vacuo at room temperature from the material remaining in the dialysis tubing. The residue was dissolved in dry methanol (20 ml). IR spectra of copolymers: FIG. 18.

EXAMPLE 8

Preparation of 1-methoxy-4-(2'-ethylhexyloxy)benzene

Sodium metal (6.50 g, 283 mmol) was dissolved in dry methanol (100 ml) under Ar to give a 2.5M solution of sodium methoxide. A solution of 4-methoxyphenol (29.3 g, 236 mmol) in dry methanol (150 ml) was added and this mixture was heated to reflux for 30 min. After cooling to room temperature, a solution of 1-bromo-2-ethylhexane (46.5 g, 259 mmol) in dry methanol (150 ml) was added dropwise. The mixture was then heated to reflux for 18 hours. The solvent was removed in vacuo, the residue dissolved in ether (200 ml), washed with dilute aqueous sodium hydroxide (500 ml) and water (500 ml), dried over $MgSO_4$ and concentrated in vacuo again. Distillation at 120° C./0.1 mm Hg afforded 24.2 g (43%) 1-methoxy-4-(2'-ethylhexyloxy)benzene.

EXAMPLE 9

Preparation of 1,4-bis (chloromethyl)-2-methoxy-5-(2'-ethylhexyloxy)benzene

A mixture of hydrochloric acid (37%, 90 ml), formaldehyde (39%, 70 ml), 1-methoxy-4-(2'-ethylhexyloxy)benzene (24.2 g, 101 mmol) and dioxane (120 ml) was saturated with hydrogen chloride for 20 min at 0° C. and stirred for 3 hours at room temperature. Another 50 ml of formaldehyde was then added at 0° C. and hydrogen chloride was bubbled through the mixture for 10 min. After stirring for 3 days at room temperature, the mixture was heated to reflux for 3.5 hours. The solvents were then completely removed to give a pale yellow solid residue which was dissolved in a minimum of hot hexane (75 ml). This solution was poured into ice-cold methanol (300 ml ). The precipitate was filtered under suction, washed with methanol (200 ml) and dried to afford 21.7 g (63%) of 1,4-bis (chloromethyl)-2-methoxy-5-(2'-ethylhexyloxy) benzene, m.p. 58°-60° C. From the mother liquor was; obtained another 5.48 g (16%) of bis (chloromethyl)-2-methoxy-5-(2'-ethylhexyloxy) benzene m. p. 53°-55° C. $^1H$ NMR (250.1 MHz, $CDCl_3$): $\delta$ =0.85-0.96 (m, 6H), 1.26-1.75 (m, 9H), 3.74-3.86 (m, 2H), 3.83 (s, 3H), 4.06 (s, 4H), 6.89 (s, 1H), 6.90 (s, 1H). IR (KBr): 2924 (m), ].516 (s), 1466 (m), 1415 (s), 1263 (s), 1227 (s), 1182 (s), 1032 (s), 733 (m), 700 (s), 614 $cm^{-1}$ (m).

EXAMPLE 10

Preparation of $\alpha,\alpha'$-bis(tetrahydrothiophenium chloride)-2-methoxy-5-(2'-ethylhexyloxy)-p-xylene Tetrahydrothiophene (6.4 ml, 72 mmol ) was added to a suspension of 2,5-bis(chloromethyl)-1-methoxy-4-(2'-ethylhexyloxy)benzene (4.80 g, 14.4 mmol) in dry methanol (75 ml), The mixture was then heated to 50° C. for 22 hours. The solvent was completely removed in vacuo, the residue treated with dry acetone, then filtered under suction and dried to give 4.36 g (59%) of $\alpha,\alpha'$-bis(tetrahydrothiophenium chloride)-2-methoxy-5-(2'-ethylhexyloxy)-p-xylene $^1HNMR$ (250.1 MHz, $CD_3OD$): $\delta=0.89$-1.04 (M), 1.18 (t,J—7.0 Hz, 3H), 1.29-1.65 (m, 8H), 1.82 (m, I H), 2.32-2.55 (m, 8H), 3.50-4.56, 4.57 (both s, 2H, $CH_2Cl$), 7.38 and 7.39 (both s, 1H, arom. H). IR (KBr): 2948 (broad, m), 1514 (s), 1460 (m), 1399 (s), 1312 (m), 1229 (s), 1033 (s), 703 $cm^{-1}$ (m).

EXAMPLE 11

Figure 22:
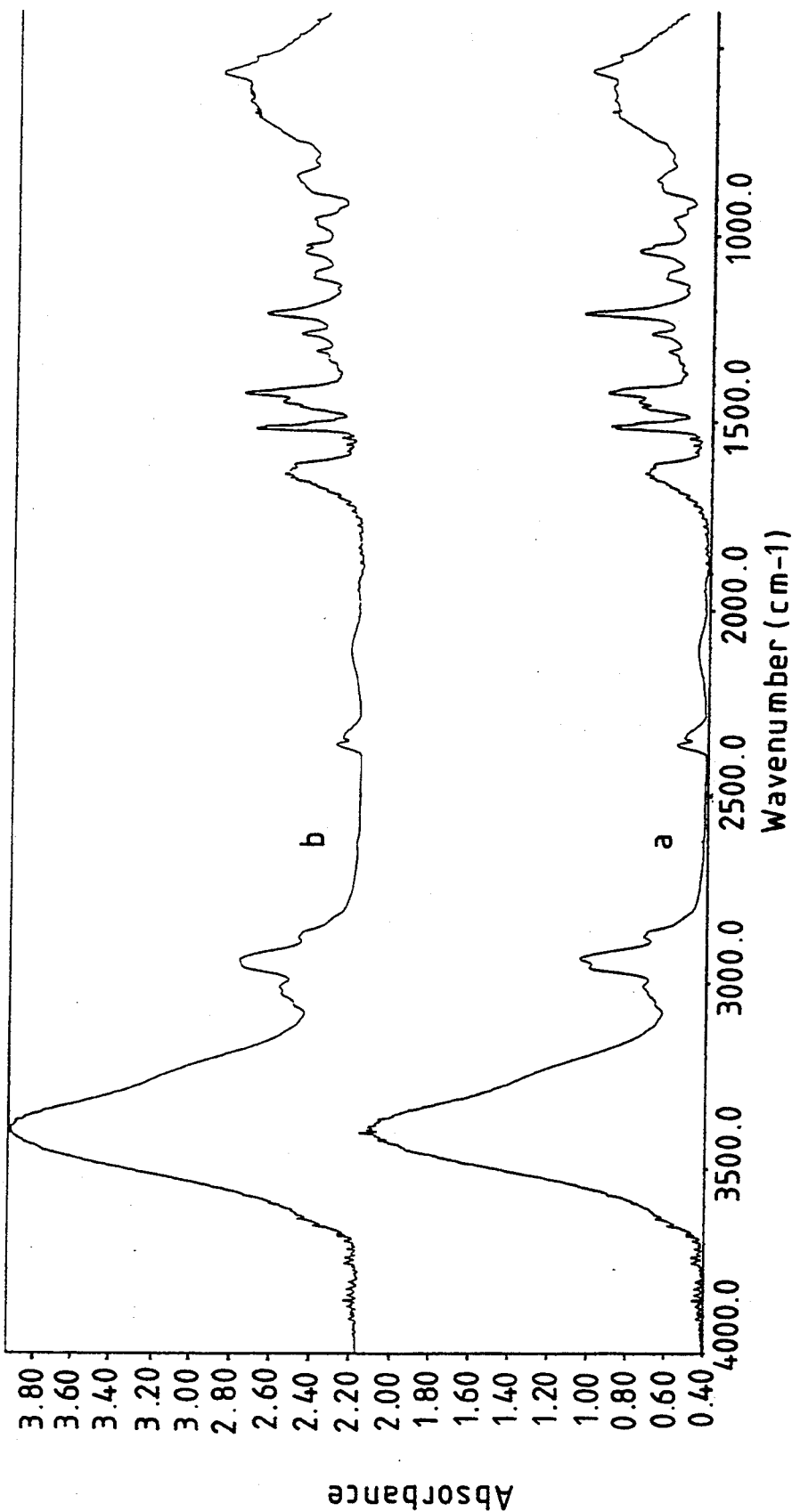
FIG. 22 is a graph showing the infrared spectra of precursors of random copolymers of PPV and MEH-PPV (2-methoxy-5-(2'-ethylhexyloxy)-PPV produced from 90:10 and 95:5 w/w ratios of PPV and MEH-PPV (2-methoxy-5-(2'-ethlyhexyloxy)-PPV) monomer units respectively.

A mixture of $\alpha,\alpha'$-bis(tetrahydrothiophenium chloride)-p-xylene (0.92 g, 2.6 mmol) and $\alpha,\alpha'$-bis(tetrahydrothiophenium chloride)-2-methoxy-5-(2'-ethylhexyloxy)-p-xylene (0.11 g, 0.22 mmol) in methanol (10 ml) was deoxygenated with argon and cooled with an ice-bath. An argon aeoxygenated ice-cold aqueous sodium hydroxide solution (0.4M, 2.6 mmol, 6.5 ml) was added dropwise and the reaction mixture was left to stir for 2.5 hours at 0° C. under inert atmosphere. The reaction was terminated by addition of hydrochloric acid (0.4M, 0.8 ml). The viscous solution was then dialyzed against deoxygenated distilled water (3×2000 ml) over 3 days using cellulose membrane dialysis tubing with a molecular weight cut-off of 12,400 (supplied by sigma chemical Company Ltd, Dorset, U. K.). The solvent was completely removed in vacuo at room temperature from the material remaining in the dialysis tubing. The residue was dissolved in dry methanol (20 ml). IR spectra of copolymers: FIG. 22.

EXAMPLE 12

Figure 24:
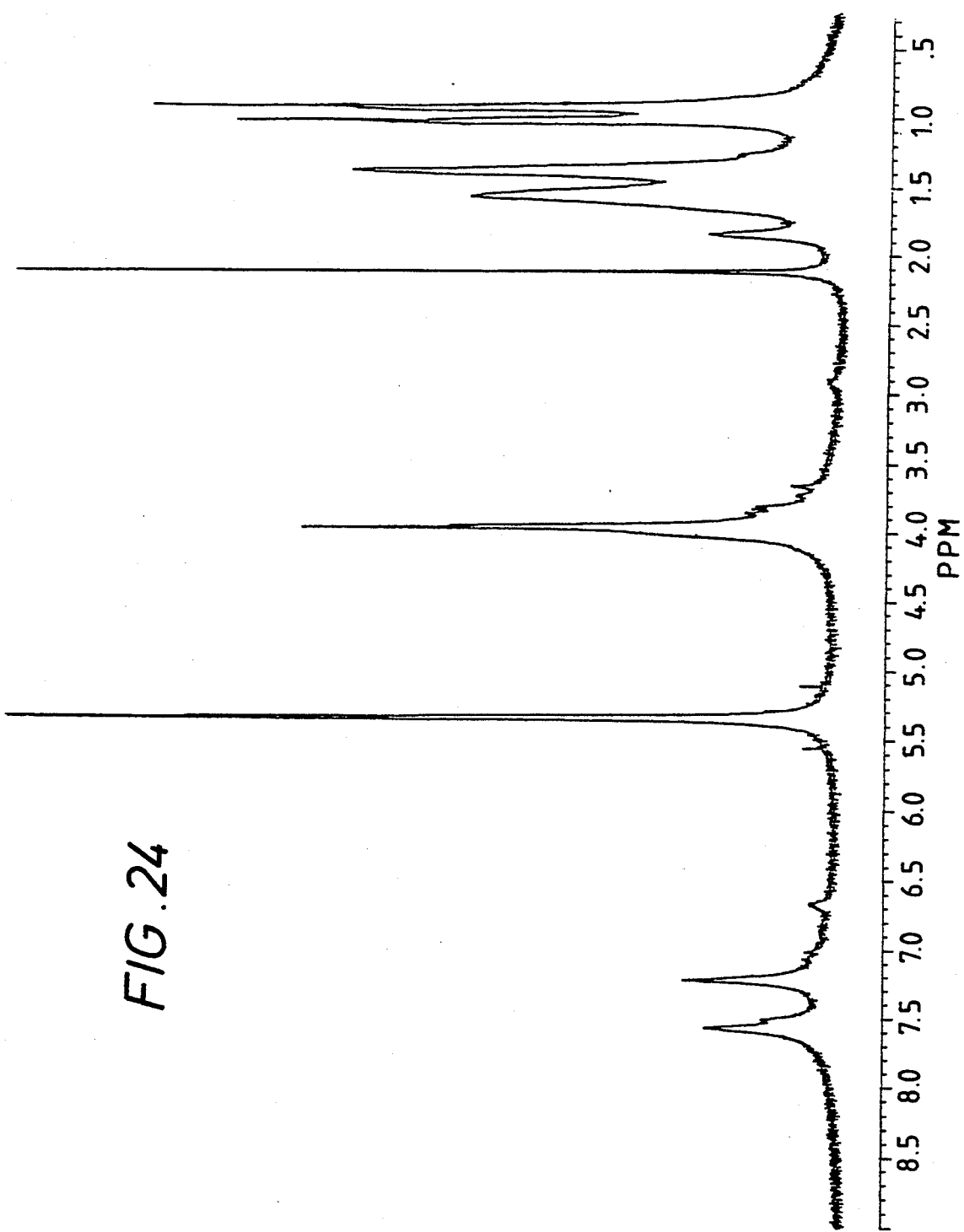
FIG. 24 is a $^1$H NMR spectrum of the copolymer described in example 11 produced from 5:95 w/w ratio of PPV and MEH-PPV monomer units.
Figure 25:
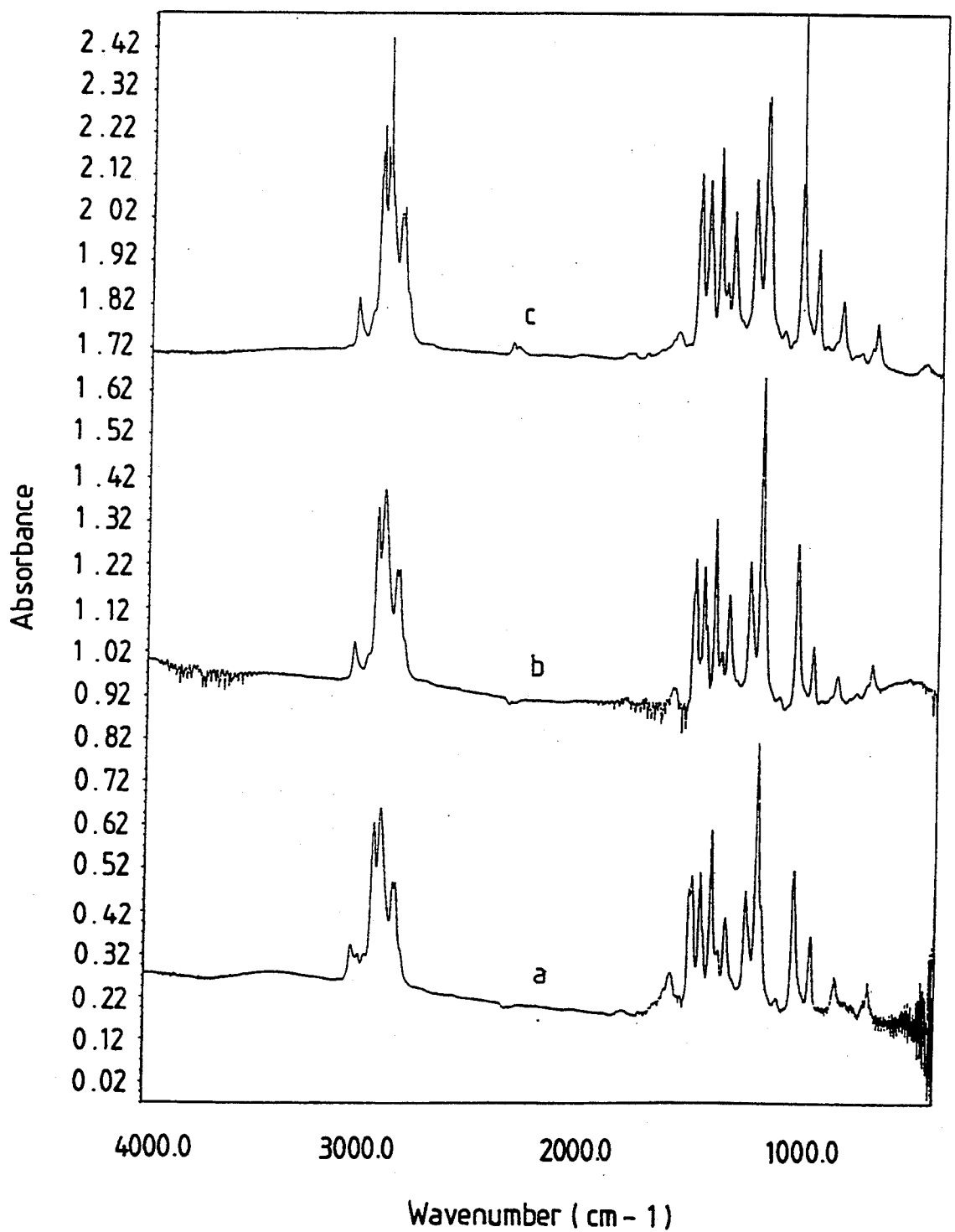
FIG. 25 is a graph showing the infrared spectra of (c) MEH-PPV and of random copolymers of PPV and MEH-PPV produced from (a) 20:80 and (b) 5:95 w/w ratios of PPV and MEH-PPV monomer units, respectively, by the method described in example 11.

A solution of 1,4-bis(chloromethyl)-2-methoxy-5-(2'-ethylhexyloxy) benzene (0.95. g, 2.9 mmol) and $\alpha,\alpha'$-dichloro-p-xylene (0.05 g, 0.29 mmol) in dry tetrahydrofuran (20 ml) was added to a solution of potassium tert-butoxide (95%, 2.5 g, 22 mmol) in dry tetrahydrofuran (120 ml) over 15 min. The mixture was then stirred at room temperature for 21.5 hours. The resulting orange mixture was reduced to 10% of its volume and poured into methanol (500 ml). The precipitate was filtered under suction and recrystallised from tetrahydrofuran/methanol to afford 101 mg of polymer. $^1H$ NMR ($CD_2Cl_2$) : FIG. 24. IR spectra of copolymers: FIG. 25.

Figure 26:
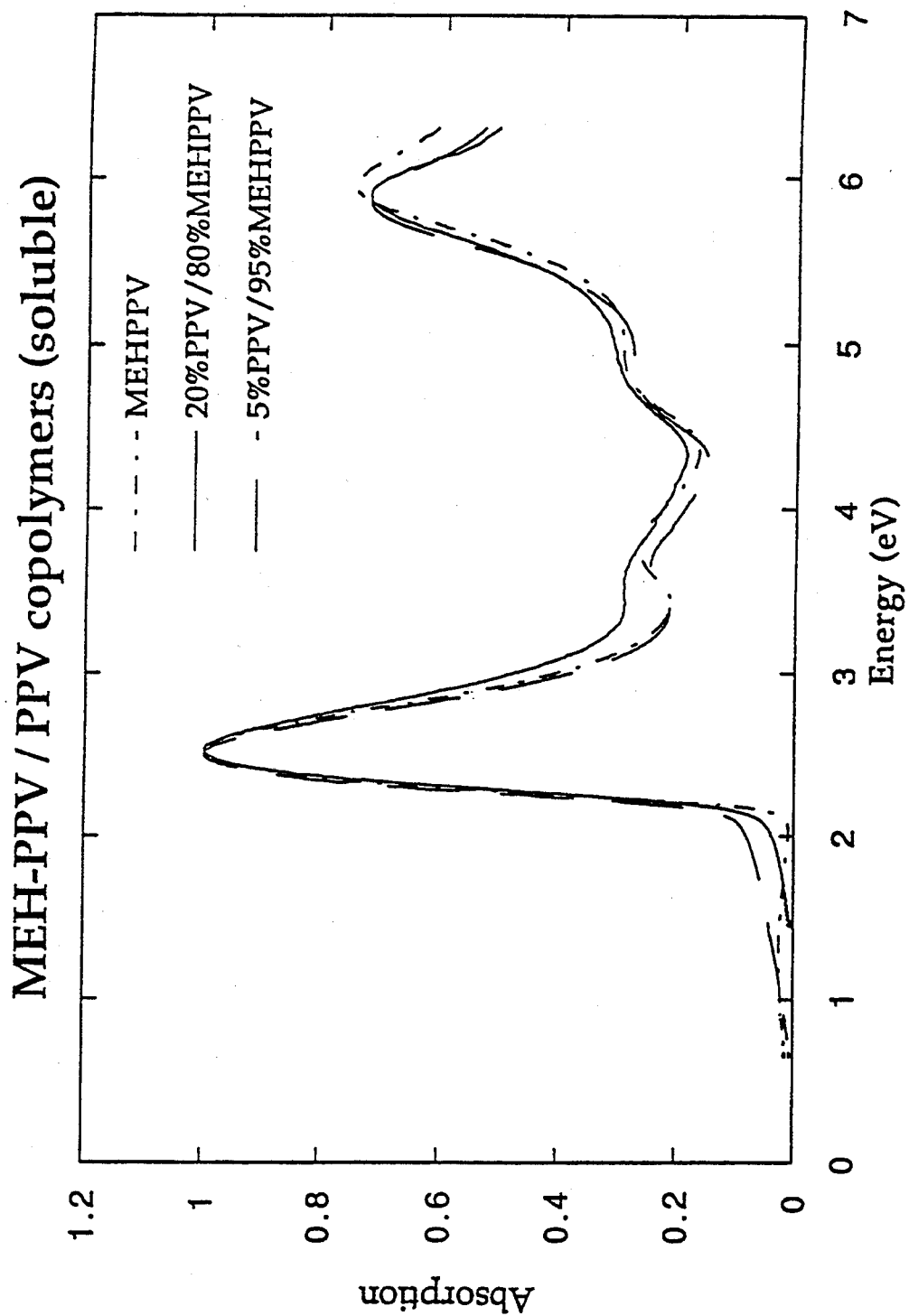
FIG. 26 is a graph showing the absorption spectra of spin-coated thin films of MEH-PPV and of random copolymers of PPV and MEH-PPV produced from 20:80 and 5:95 w/w ratios of PPV and MEH-PPV monomer units, respectively.
Figure 27A:
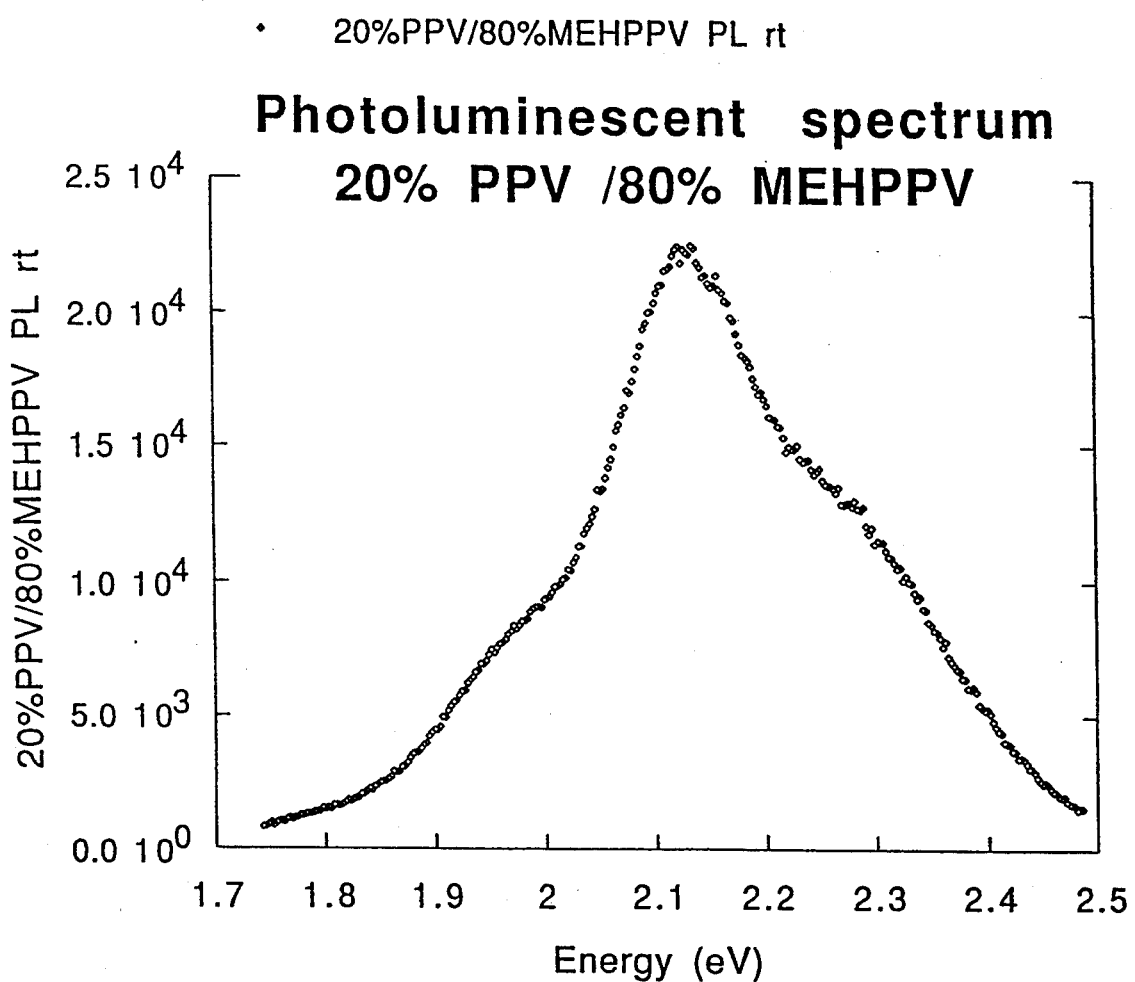
FIGS. 27a and 27b are graphs showing the photoluminescence emission spectra of random copolymers of PPV and MEH-PPV produced from 20:80 and 5:95 w/w ratios of PPV and MEH-PPV monomer units, respectively.
Figure 27B:
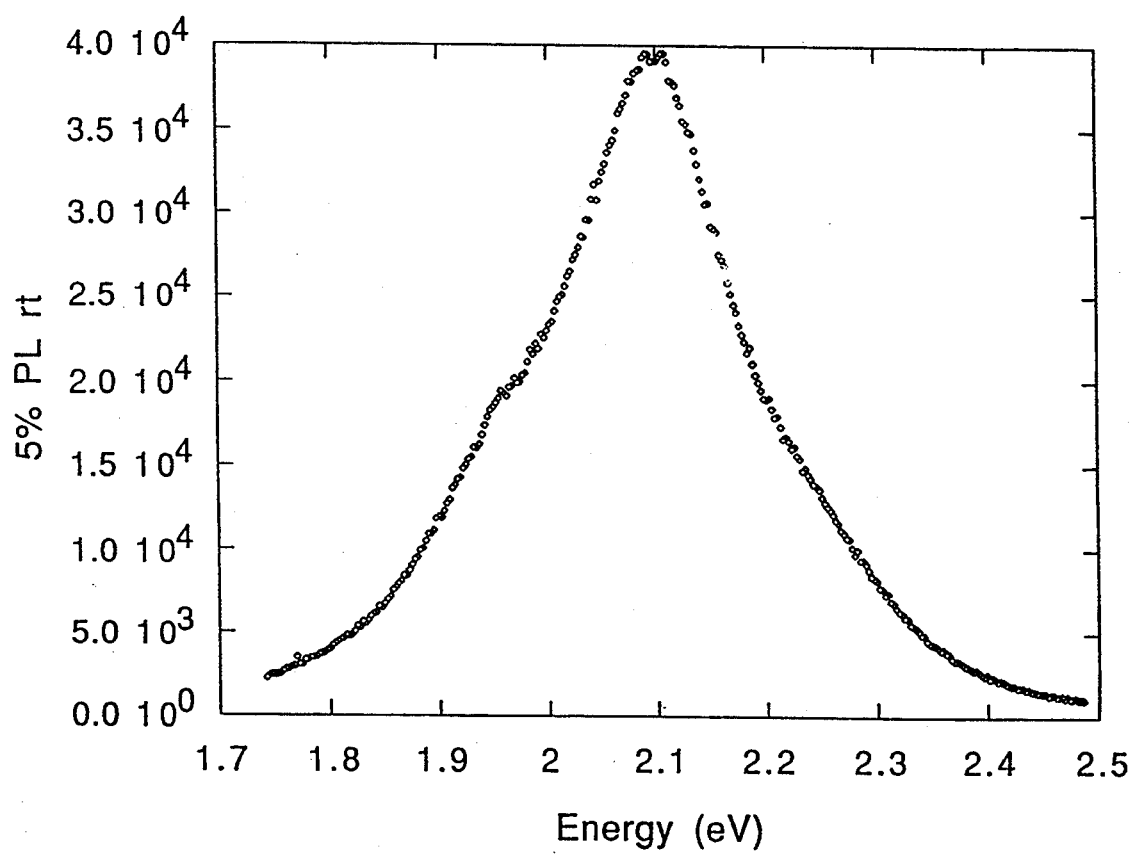
Figure 28A:
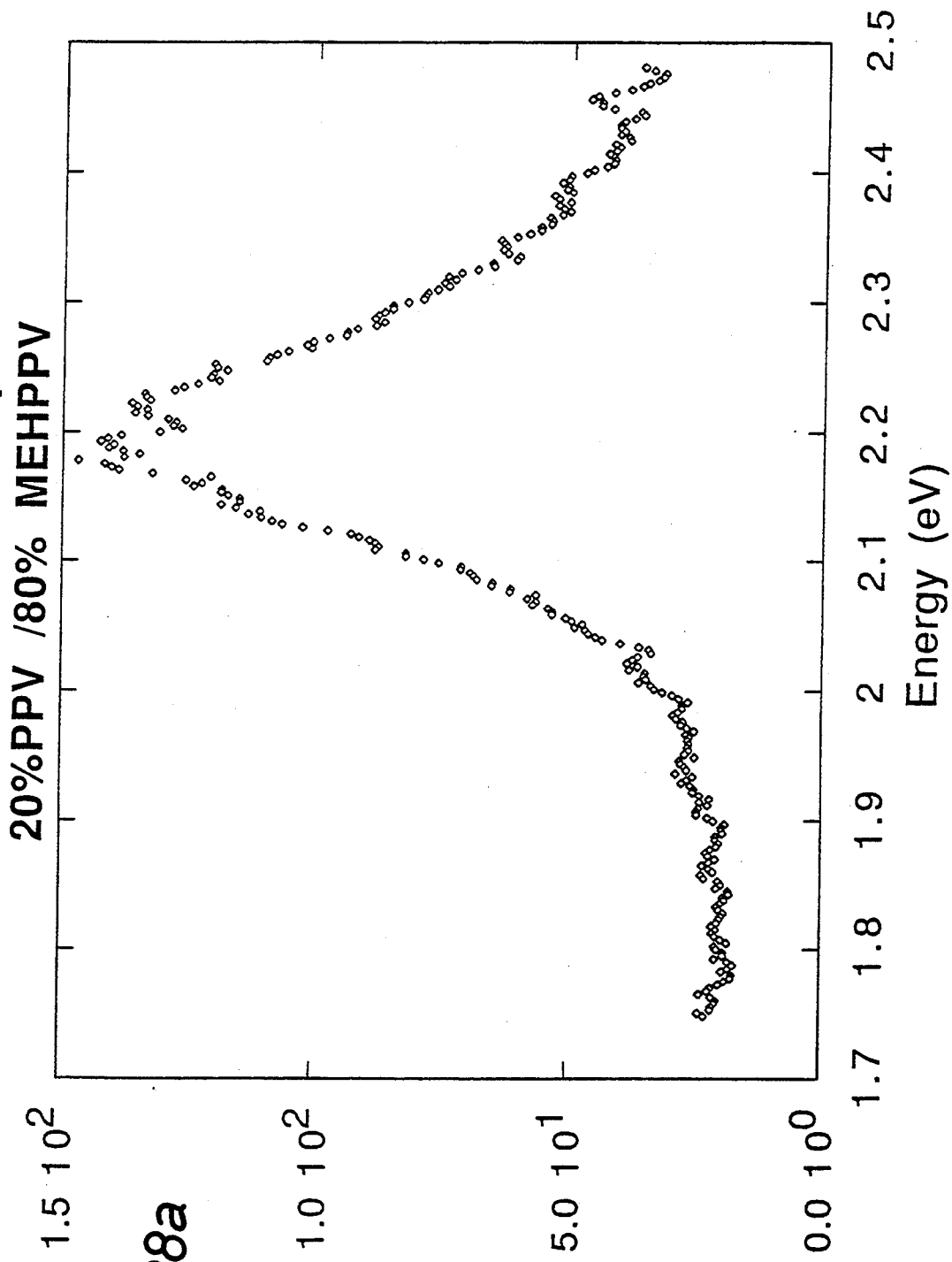
Figure 29A:
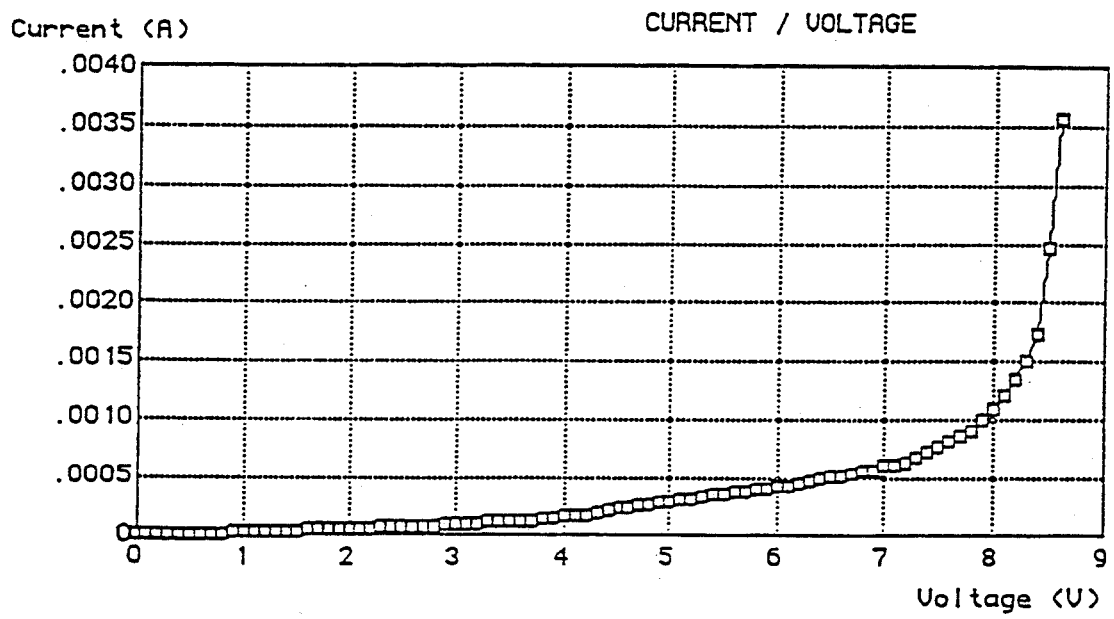
FIGS. 29a and 29b are graphs showing the current/voltage characteristics and luminance/voltage relationship for a thin film of a random copolymer of PPV and MEH-PPV produced from 20:80 w/w ratio of PPV and MEH-PPV monomer units thin; films were spin-coated onto substates of ITO coated glass and aluminium cathodes were evaporated on top.
Figure 29B:
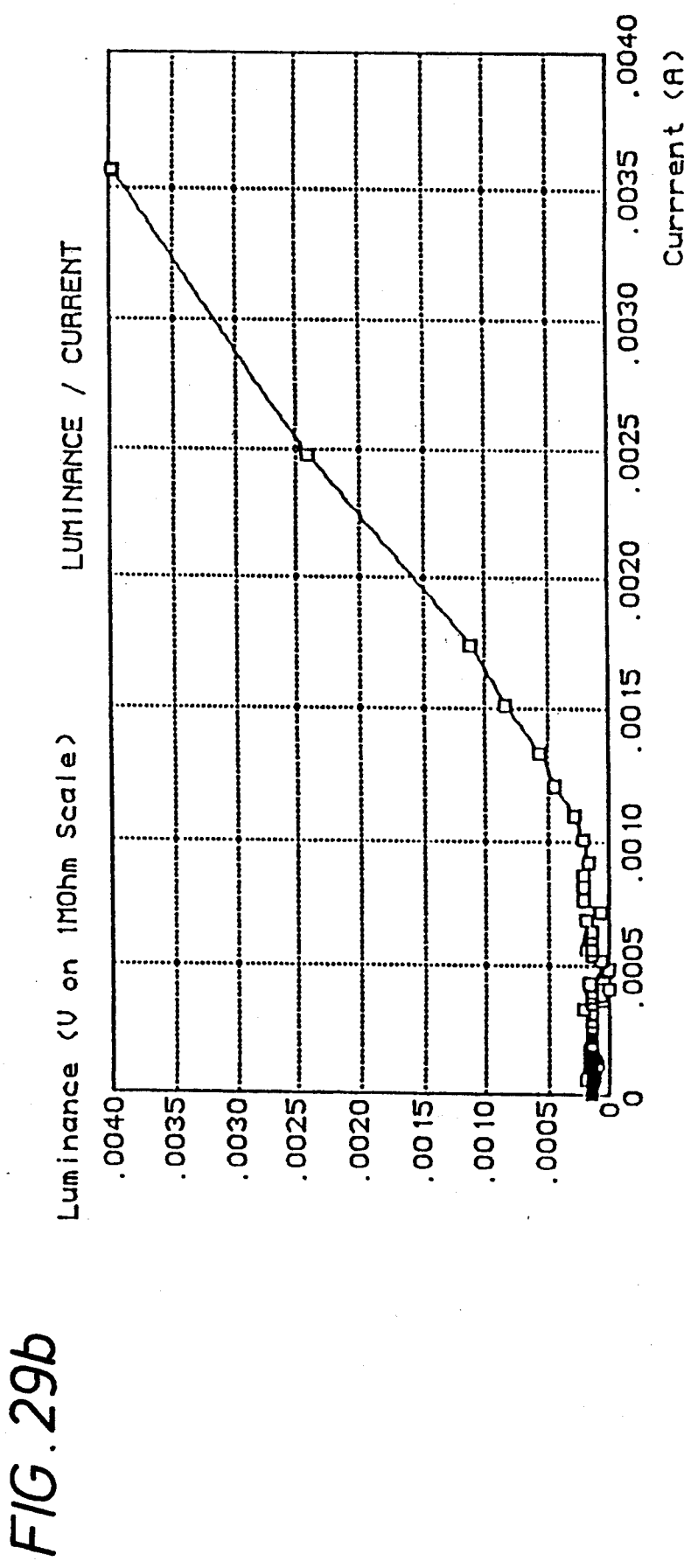
Figure 30A:
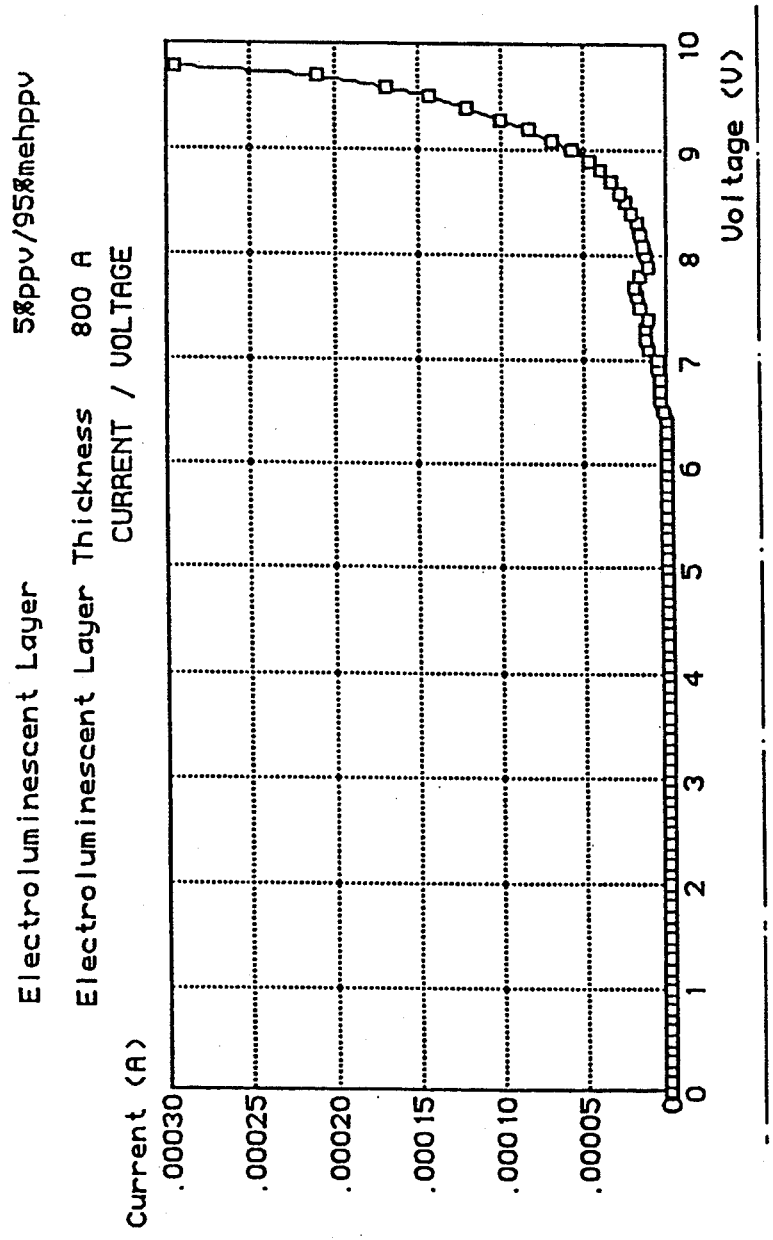
FIGS. 30a and 30b are graphs showing the current/voltage characteristics and luminance/voltage relationship for a thin film of random copolymer of PPV and MEH-PPV produced from 5:95 w/w ratio of PPV and MEH-PPV monomer units: thin films were spin-coated onto substates of ITO coated glass and aluminium cathodes were evaporated on top.
Figure 30B:
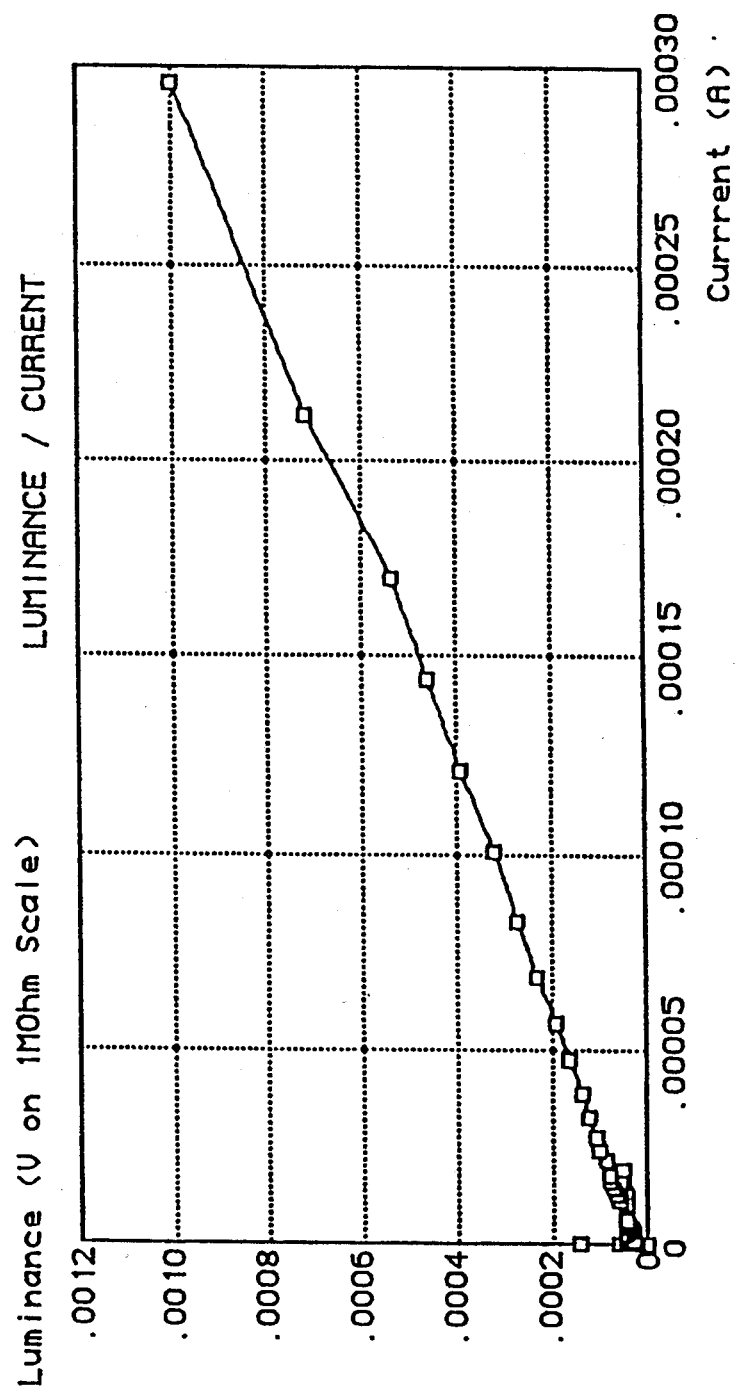
Figure 31:
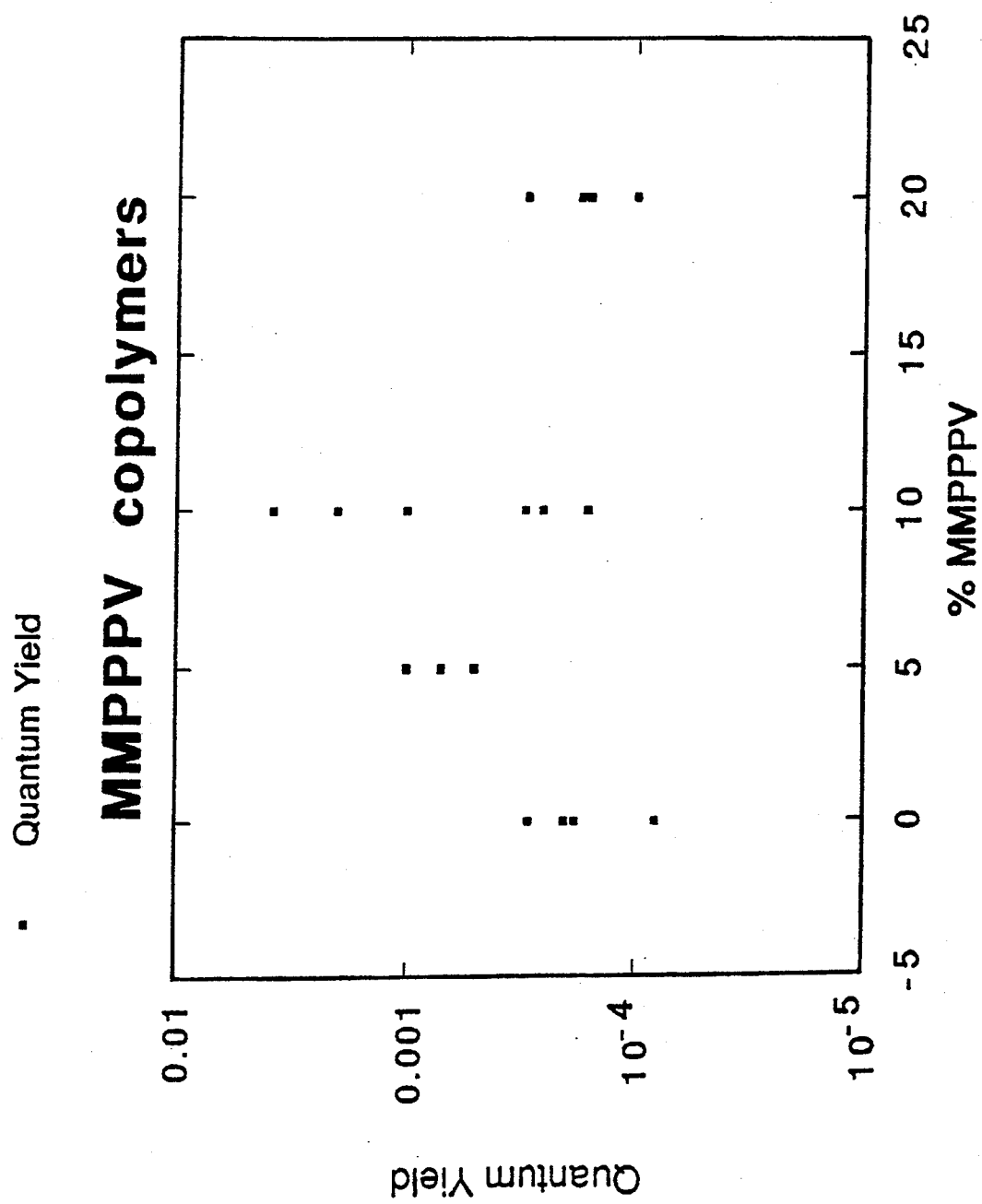
FIG. 31 is a scatter graph showing the quantum yield of random copolymers formed from PPV and MMP-PPV monomer units as measured in thin film structures with hole injecting electrodes of oxidised aluminium, a spin-coated film converted at 220° C. in vacuo for 12 hours, and with electron injecting electrodes of aluminium.
Figure 31A:
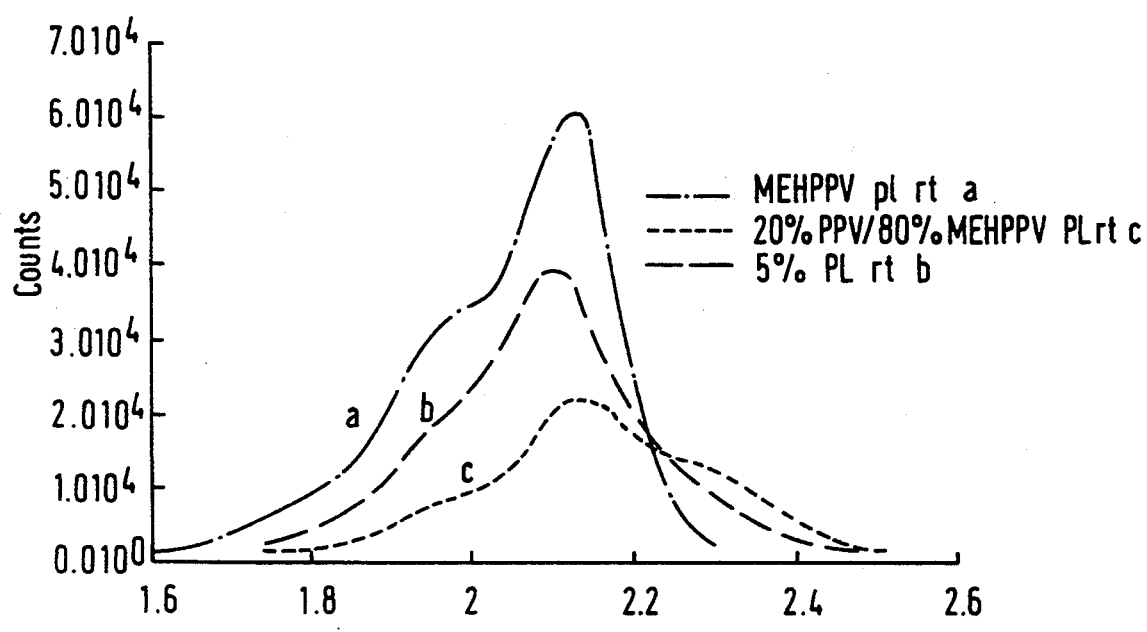
FIG. 31a is a graph showing the photoluminescence spectra of MEH-PPV and random copolymers of (a) MEH-PPV and PPV produced from (b) 95:5 and (c)

The absorption spectra of MEH-PPV, 5% PPV/95% MEH-PPV and 20% PPV/80% MEH-PPV are shown in FIG. 26. The photoluminescent spectra (FIG. 27a, 26b, 31a) show that the luminescence is as expected of higher energy with increasing number of PPV units. EL devices were made in a standard configuration with ITO and aluminium contacts and the material showed electroluminescence (FIG. 29a, 29b, 30a and 30b). The corresponding electroluminescence spectra are illustrated in FIG. 28a and 28b. Both the 5% PPV/95% MEH-PPV and the 20% PPV/80% MEH-PPV had a turn-on voltage of about 8V.

EXAMPLE 13

The previous PPV EL devices were constructed with PPV prepared via a Tetrahydrothiophenium (THT)-leaving precursor polymer (FIG. 32a) spun from methanolic solution. This precursor is unstable with respect to its conjugated product and is fully converted by heating at 220° C. for 2 hours (FIG. 32c).

By replacing the THT-leaving group with a methoxy (MeO)-leaving group a more stable precursor (FIG. 32b) is formed. This can be easily processed by spin coating from a solution in chloroform (as can the THT-precursor from methanolic solution). Thermal conversion of the MeO-leaving PPV precursor at 300° C. in vacuo for 12 hours gives very little thermal elimination leaving a copolymer of conjugated and unconjugated units (FIG. 32d). This is clearly seen from the absorption spectra of the THT-leaving PPV and the MeO-leaving PPV (FIG. 33). The absorption spectra of the precursors of both are very similar. A significant change occurs in the absorption spectrum of the THT-leaving PPV (FIG. 34); an insignificant change occurs in the absorption spectrum of the MeO-leaving PPV (FIG. 35). Clearly both products are subsequently very stable against subsequent changes at room temperatures and are very suitable as emitting materials in commercial EL devices.

A device was made with the MeO-leaving PPV. An ITO substrate was cleaned in an ultrasound bath, of first acetone and subsequently propan-2-ol. The precursor material was then spin-coated on the substrate. The device was then thermally converted at 300° C. in vacuo for 12 hours. A top contact of Aluminium was then deposited to define an active area by vacuum deposition at a pressure of less than $6.10^{-6}$ torr to a thickness of 2-500A.

The performance of the device shows no deterioration over those made with PPV prepared via a THT leaving group precursor polymer with a turn on voltage below 10V, a diodic current-voltage characteristic and a largely linear current-luminance response and a slightly improved quantum efficiency by at least a factor of 2 (FIGS. 36 and 37).

The emission spectrum of the MeO-leaving PPV is markedly different with a peak emission at 2.5 eV compared with 2.25 eV in THT-leaving PPV. The emission is a bluey-green as opposed to a greeny-yellow in the case of the THT-leaving PPV. This is again consistent with the MeO-leaving PPV as converted being a copolymer of conjugated and unconjugated sequences: emission coming from the small conjugated sequences but at a higher energy than in fully conjugated PPV, (FIG. 37).

Thus by careful conversion conditions it is possible using copolymers of PPV to obtain electroluminescent emission of different colours and with improved efficiencies.

EXAMPLE 14

The random copolymers of PPV and DMeOPPV give a means to controlling the bandgap of a conjugated polymer and the potential for the construction of multicolour EL devices and channel waveguides.

The copolymers are prepared initially in a precursor form which is soluble in Methanol and consists of at least 3 distinct monomer units—a PPV precursor monomer unit with a THT-leaving group, a DMeOPPV monomer unit with a THT-leaving group and certainly a DMeOPPV monomer unit with a MeO-leaving group (formed by the methanolic solution substitutionally attacking the DMeOPPV THT-leaving units) as seen by the strong 1094 cm$^{-1}$ adsorption in the infrared absorption spectra of both the MeO-leaving homopolymer precursor of DMeOPPV and all the copolymer precursor polymers. There is possible a small amount of a fourth monomeric unit—a PPV monomer unit with a MeO-leaving group (formed by the methanolic solution substitutionally attacking the PPV THT-leaving units) (FIG. 39(a)).

Thin films (of the order of 1000A as used in EL devices) of the copolymers can be obtained by Spin-coating the precursor solutions. Thermal conversion of the said films gives mechanically and thermally robust films. It is found that by linearly varying the copolymer monomer unit ratio that the absorption edge of the converted copolymers may be accurately controlled (FIG. 40). Typically films are converted at 220° C. for 2 hours. More fully conjugated material has a lower bandgap. The controlled increase in bandgap with additional DMeOPPV to PPV units indicates an associated decrease in conjugation. FTIR data shows that the copolymers are only partially conjugated as converted (FIG. 41). There is still a significant absorption at 1094 cm$^{-1}$ indicating monomeric units of DMeOPPV with the methoxy leaving group have not been converted to the conjugated form leaving a copolymer of conjugated sequences and unconjugated sequences. The degree of conjugation will thus vary with the number of DMeOPPV Units present (FIG. 42).

To convert fully the homopolymer of DMeOPPV with the methoxy leaving group it is necessary to heat the precursor in the presence of acid to catalyse the loss of the methoxy group. As the THT-leaving group leaves, acid is also generated. Thus in the copolymers of PPV and DMeOPPV it is possible further to convert the monomeric units of DMeOPPV with the methoxy leaving group to the conjugated form, so lowering the bandgap further and giving more control of the bandgap, by methods of internally trapping the self produced acid where excess acid may damage electrodes or simply by heating the precursor films in the presence of acid.

By converting a spun-coated film of a copolymer at 220° C. in an argon flow which has been passed through concentrated HCl for 2 hrs it is clearly seen that the absorption bandgap of the polymer is shifted to lower energy over a similar film converted at 220° C. in vacuo indicating that the "acid" converted film is more fully conjugated, FTIR absorption measurements support this with the disappearance of the 1094 cm$^{-1}$ absorption only when the copolymer is "acid" converted. Again it is noted that. 2 hours conversion by either technique gives stable material against further change (FIGS. 43 and 41).

By converting a spun-coated copolymer film on a glass substrate initially with a low temperature bake in vacuo at about 100° C. the diffusion rate of the acid ions out of the film is reduced giving an enhanced probability of causing conversion of methoxy-leaving units. A subsequent bake at 220° C. in vacuo yields fully stable material at room temperature again. A considerable reduction in bandgap is so obtained over material heated directly to 220° C. in vacuo. Thus there is a further method for controlling the bandgap of these materials (FIG. 44).

It should be emphasised that any method of controlling the bandgap in these conjugated polymers equally controls the colour of emitted light in an electroluminescent device (or the colour of photoluminescence under optical excitation) as the wavelength of the emitted light largely follows the bandgap of the material (an increase in the bandgap of the material causes a similar decrease in the wavelength of the emitted light), The spatial limit for this spatial control of bandgap across the polymer film is of the order of the thickness of the polymer film i.e. 1000A.

Another film of copolymer (30% Copolymer) was spun-coated onto a glass substrate and before thermal conversion 500A of Aluminium were vacuum deposited at a pressure of less than $6.10^{-6}$ torr via a shadow mask, The sample was then baked in vacuo for 20 hours at 220° C. to facilitate full conversion. The sample was then etched in weak sodium hydroxide solution to remove the aluminium. The polymer film was unaffected by the etching process. However, the polymer is left patterned. Where the aluminium was, the polymer to the eye is a deeper orange colour indicating a greater degree of conjugation due to enhanced trapping of the acid ions in the polymer film by the aluminium. This is born out by the shift to lower energy of the absorption edge (FIG. 45) and the photoluminescence emission (FIG. 46) of the dark region originally covered by the aluminium. Thus the bandgap of the copolymers may again be controlled and moreover in different regions of the same film giving rise to the possibility of multicolour emission from a single EL device.

Such patterning also has an application in the manufacture of channel waveguides. Another such patterned device as above was made (from 10% copolymer) and there were the same associated lowering of bandgap and absorption edge where the aluminium had been etched from (FIG. 47) and lowering in energy of the photoluminescence emission from the same area (FIG. 48). The refractive indices of the two regions at 633 nm were measured by coupling light into the first TE modes from a He-Ne laser. The refractive index of the less conjugated material was measured to be 1.564 (0.002) and that of the more conjugated material (as converted under the encapsulation of aluminium) was measured to be 1.620 (0.002). This result is in keeping with simple dispersion theory for propagation of light, in a dielectric medium such that the refractive index varies inversely with bandgap. Thus the patterning of the polymer allows also the spatial control of refractive index across a polymer film to a length scale of the order of 1000A. For typical waveguiding structures (such as a channel waveguide) it is necessary to define channels of material to a precision of the order but no smaller than the wavelength of the light to be guided (i.e. for the 633 nm emission from a He-Ne laser to a precision of the order of 6000A) with a higher refractive index than of the surrounding material. Clearly this method of patterning the copolymers of PPV and DMeOPPV is amenable to making waveguide structures as high refractive index regions can be defined to a size smaller than the wavelength of light which is to be confined in the high index region and guided.

Figure 3A:
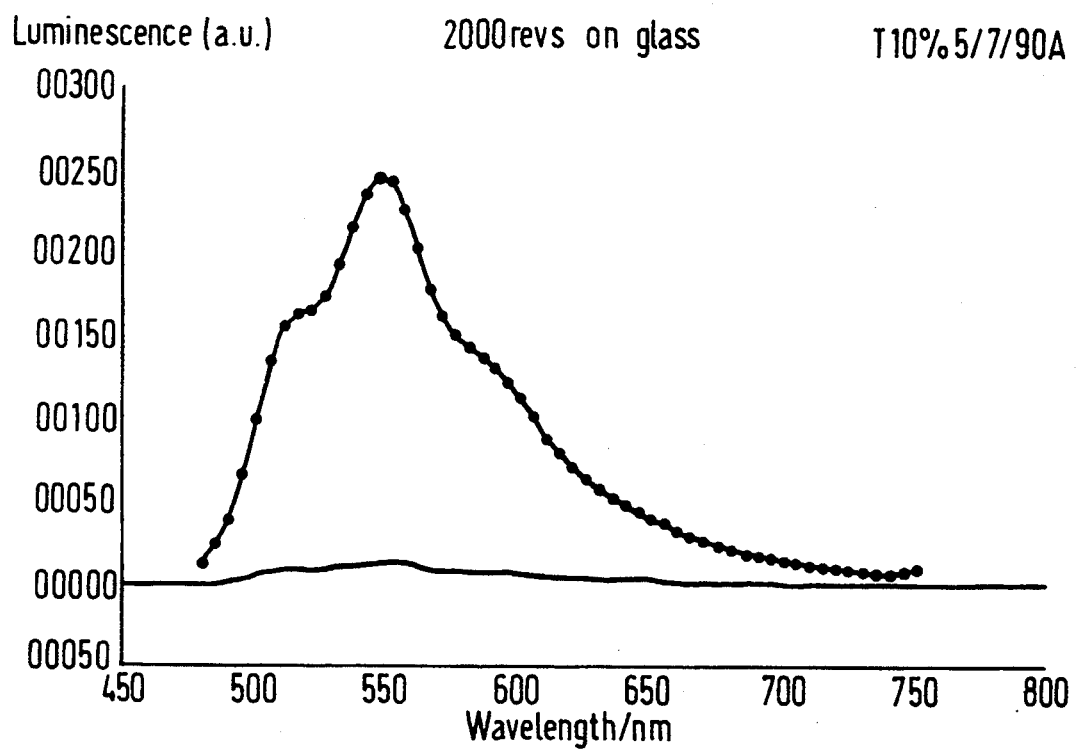
FIGS. 3a and 3b are graphs showing respectively the emission spectra for thin spin coated and thick solution cast films of a copolymer produced from a 1:9 molar ratio of dimethoxy-PPV and PPV monomer units respectively, converted at 220° C. in vacuo for two hours.
Figure 3B:
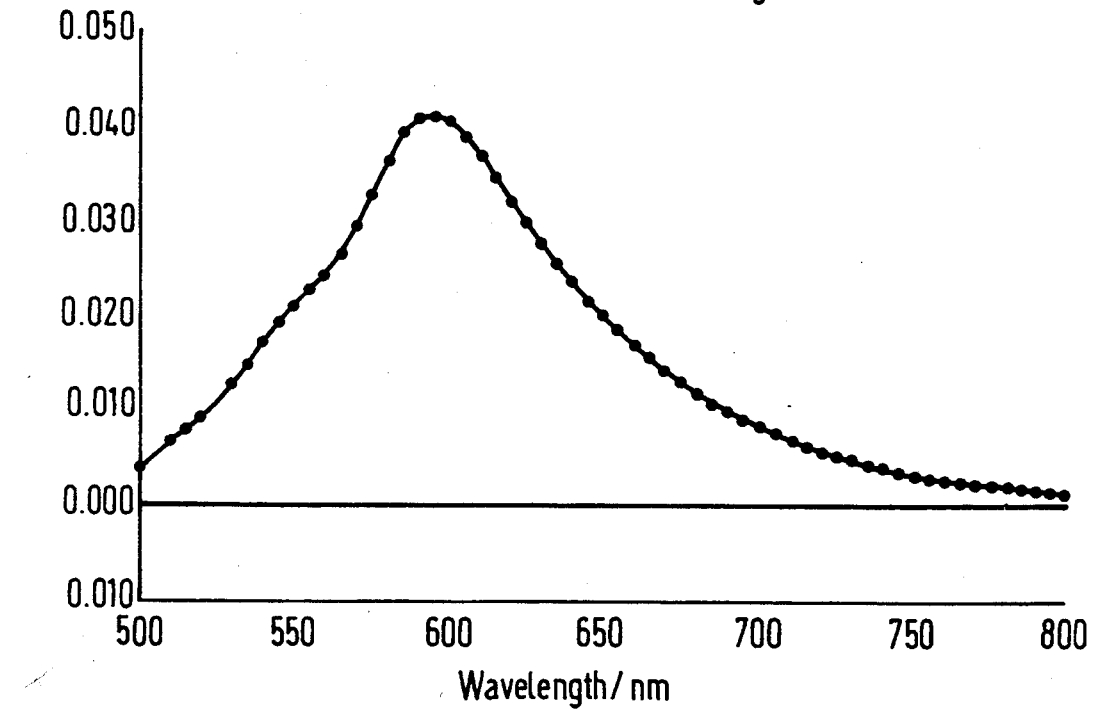
Figure 4A:
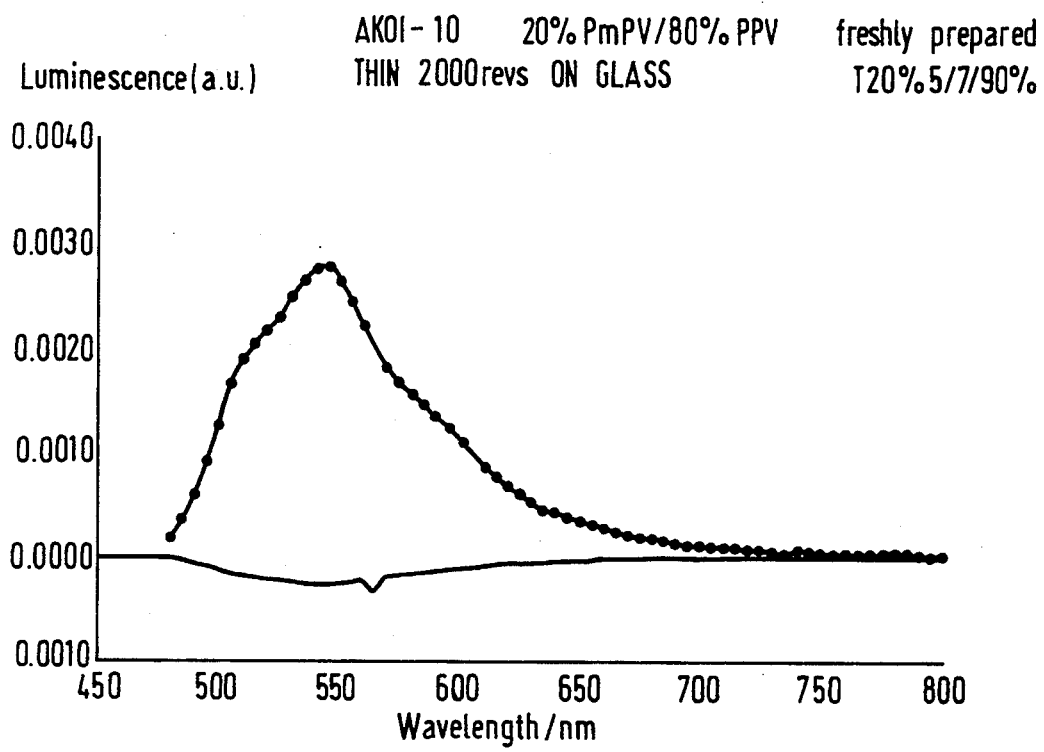
FIGS. 4a and 4b are graphs showing respectively the emission spectra for thin spin coated and thick solution cast films of a copolymer produced from a 1:4 molar ratio of dimethoxy PPV and PPV monomer units respectively, converted at 220° C. in vacuo for two hours.
Figure 4B:
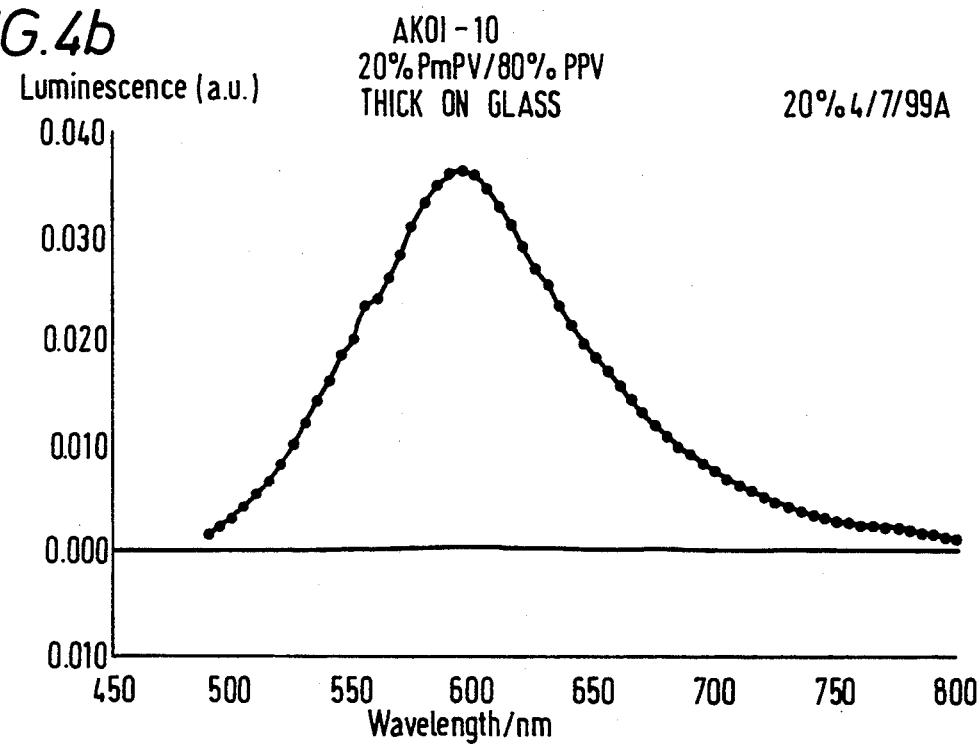
Figure 5A:
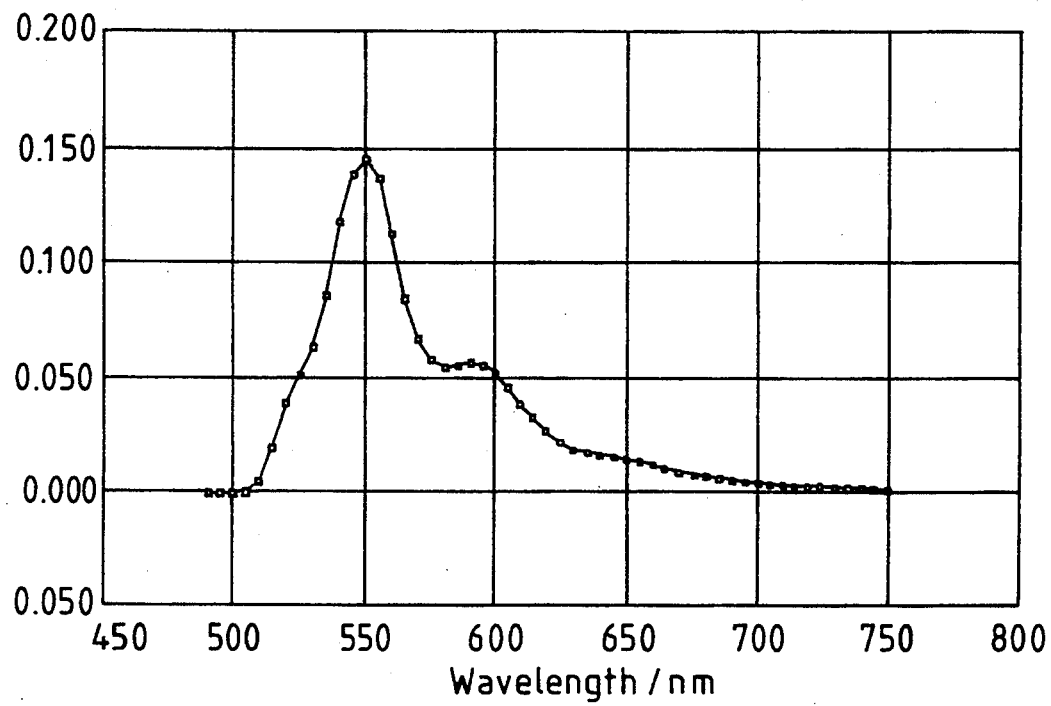
FIGS. 5a and 5b are graphs showing respectively the photoluminescence spectra for homopolymers of PPV and dimethoxy PPV.
Figure 5B:
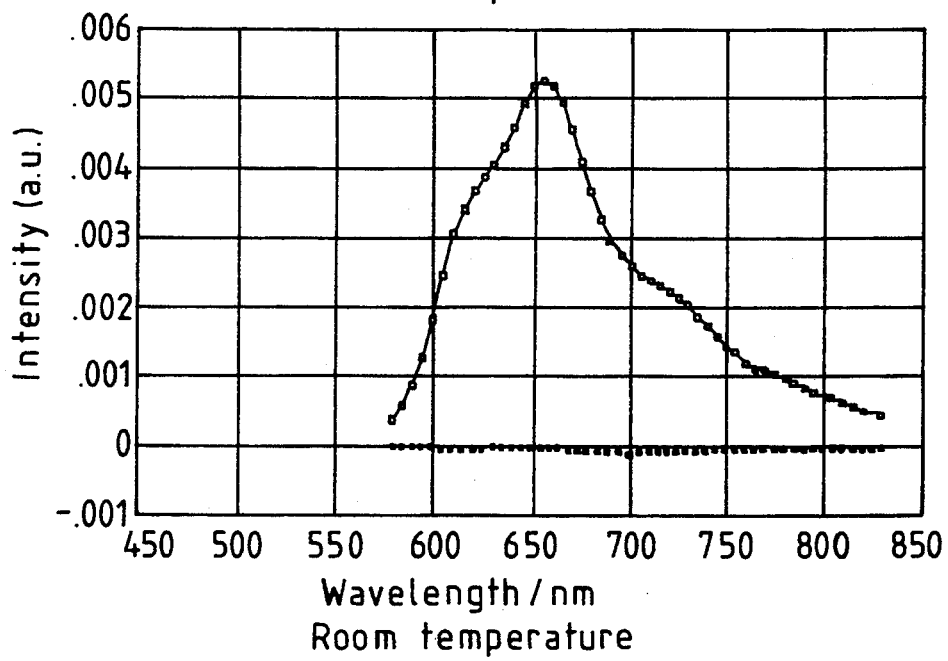
Figure 19:
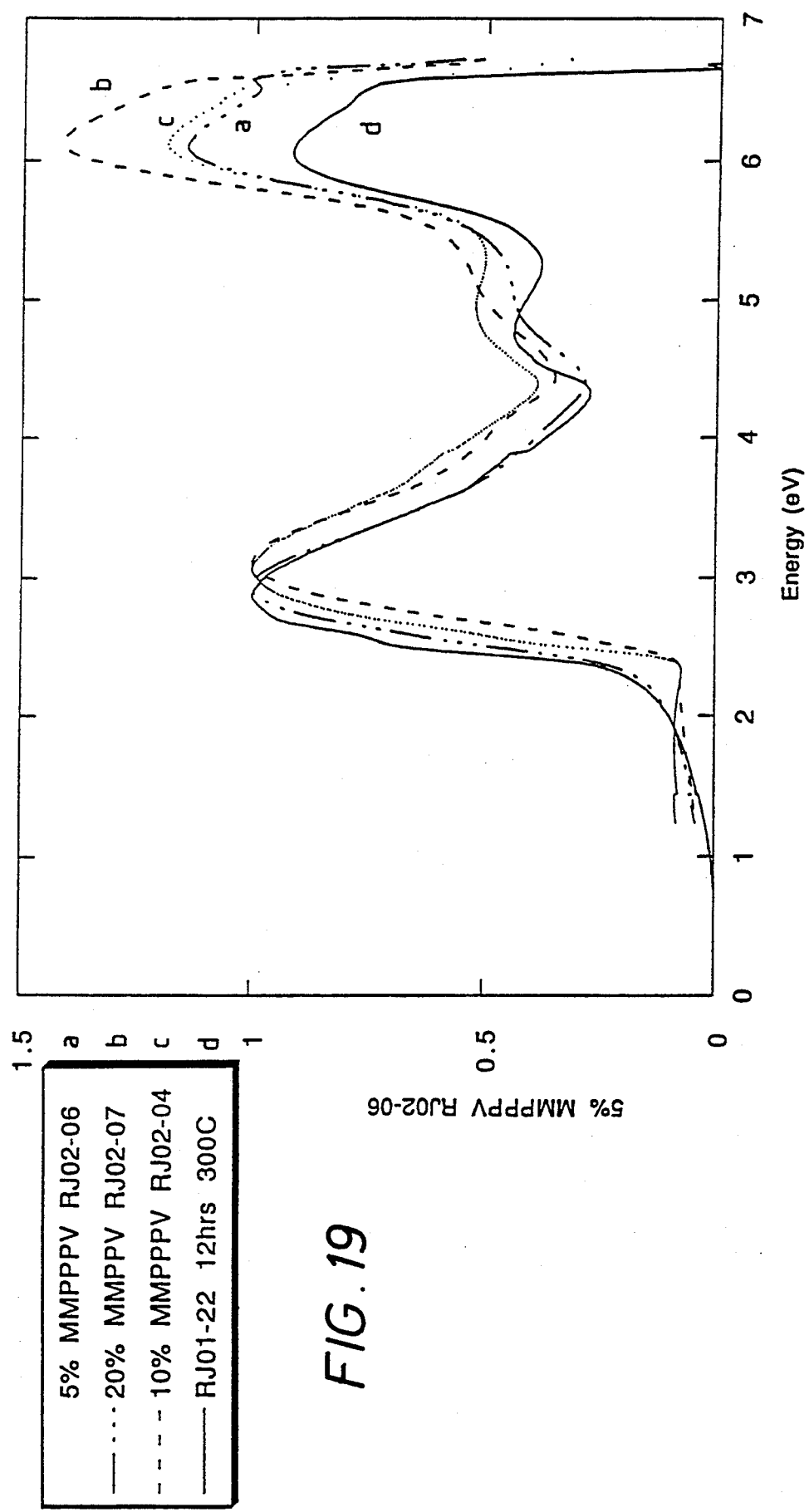
FIG. 19 is a graph showing the absorption spectra of spin-coated thin films of random copolymers of PPV and MMP-PPV produced from 80:20, 90:10, and 95:5 and 100:0 w/w ratios of PPV and MMP-PPV monomer units, respectively as converted at 220° C. in vacuo for 12 hours.
Figure 20:
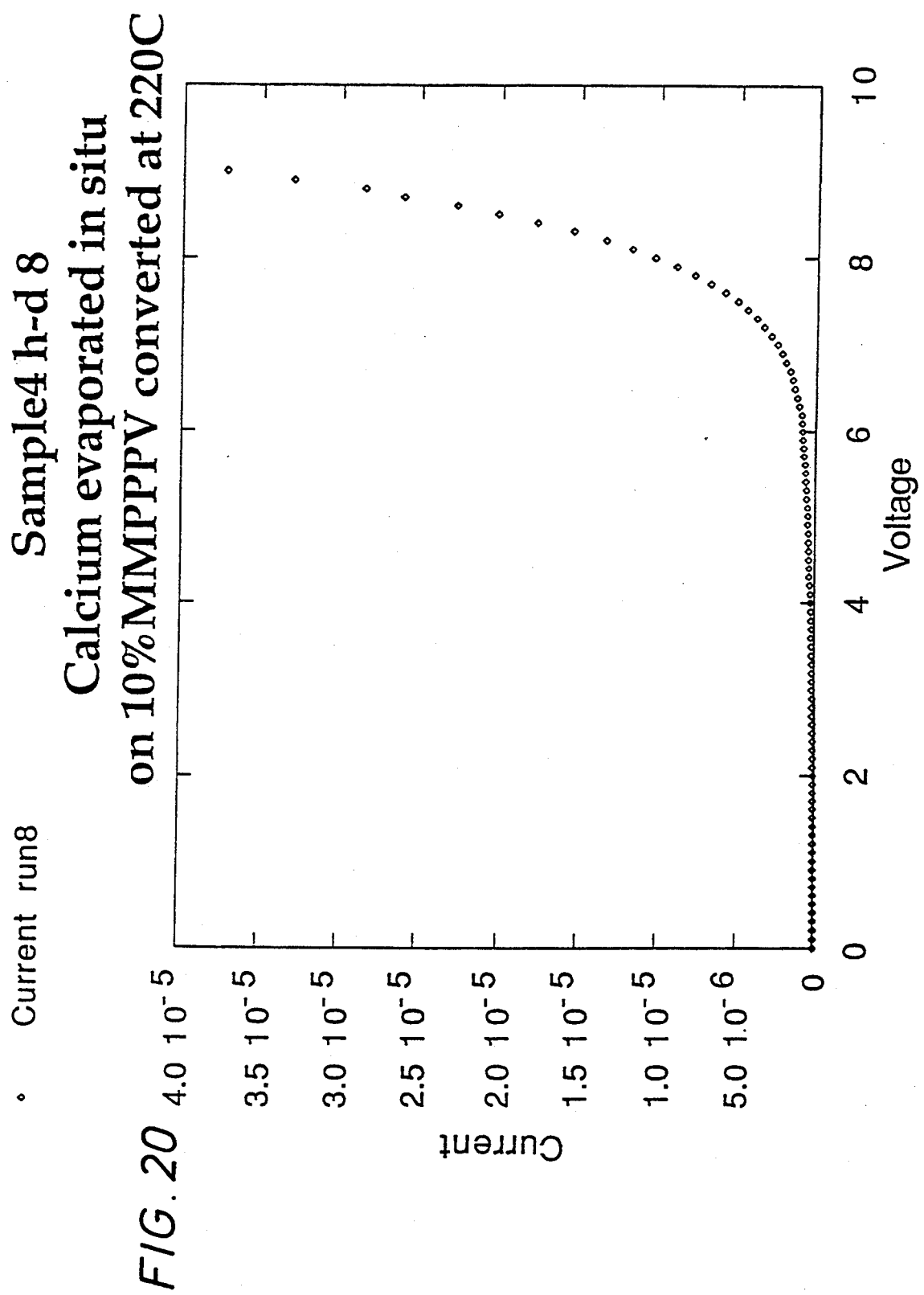
FIG. 20 is a graph showing the current/voltage characteristics of a thin film of a random copolymer of PPV and MMP-PPV produced from 90:10 w/w ratio of PPV and MMP-PPV monomer units as converted in vacuo at 220° C. for 12 hours on a substrate of ITO-coated glass and with calcium as a cathode.
Figure 21:
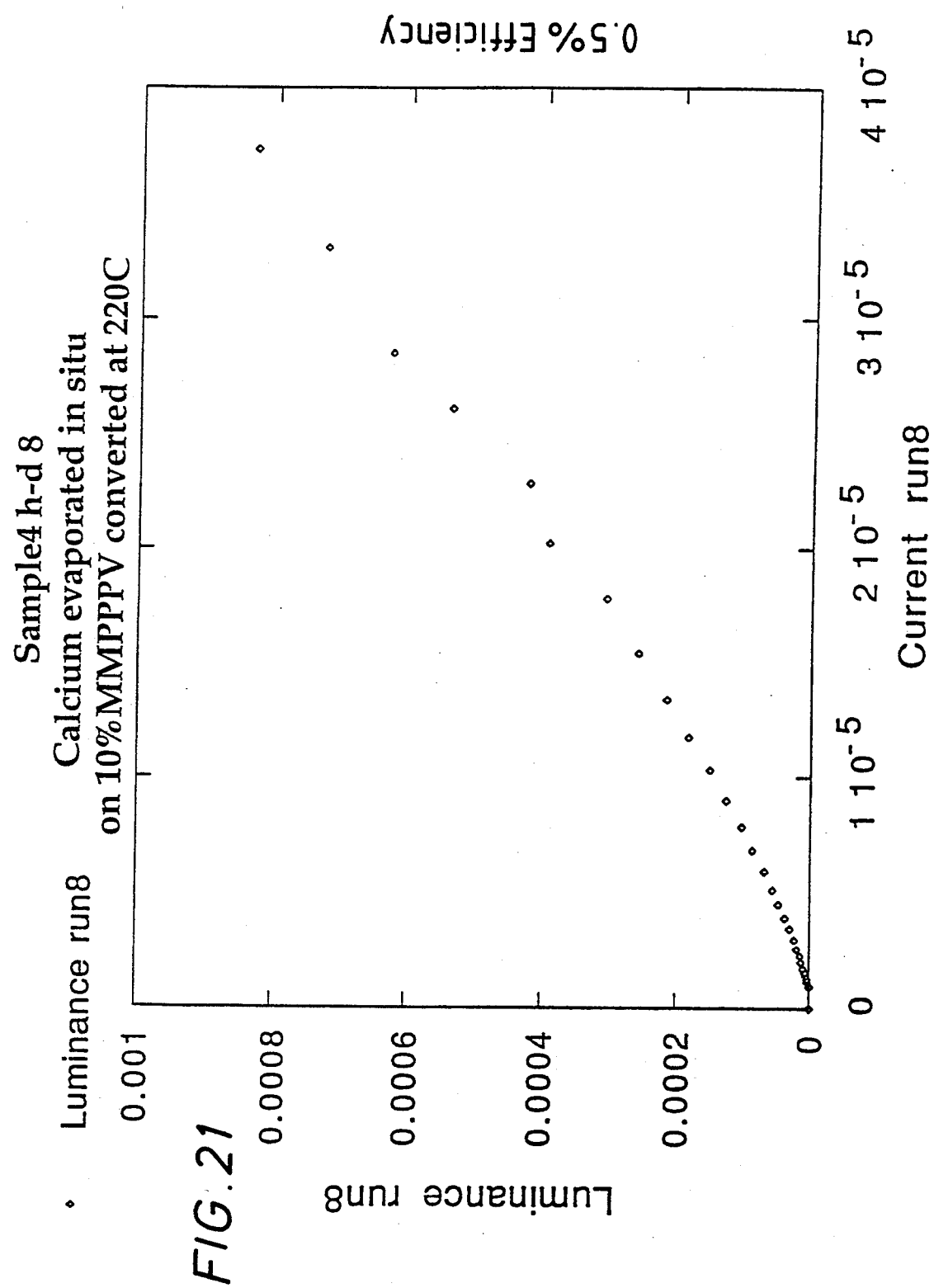
FIG. 21 is a graph showing the luminance/current characteristics of a thin film of a random copolymer of PPV and MMP-PPV produced from 90:10 w/w ratio of PPV and MMP-PPV monomer units as converted in vacuo at 220° C. for 12 hours on a substrate of ITO-coated glass and with calcium as a cathode.
Figure 23:
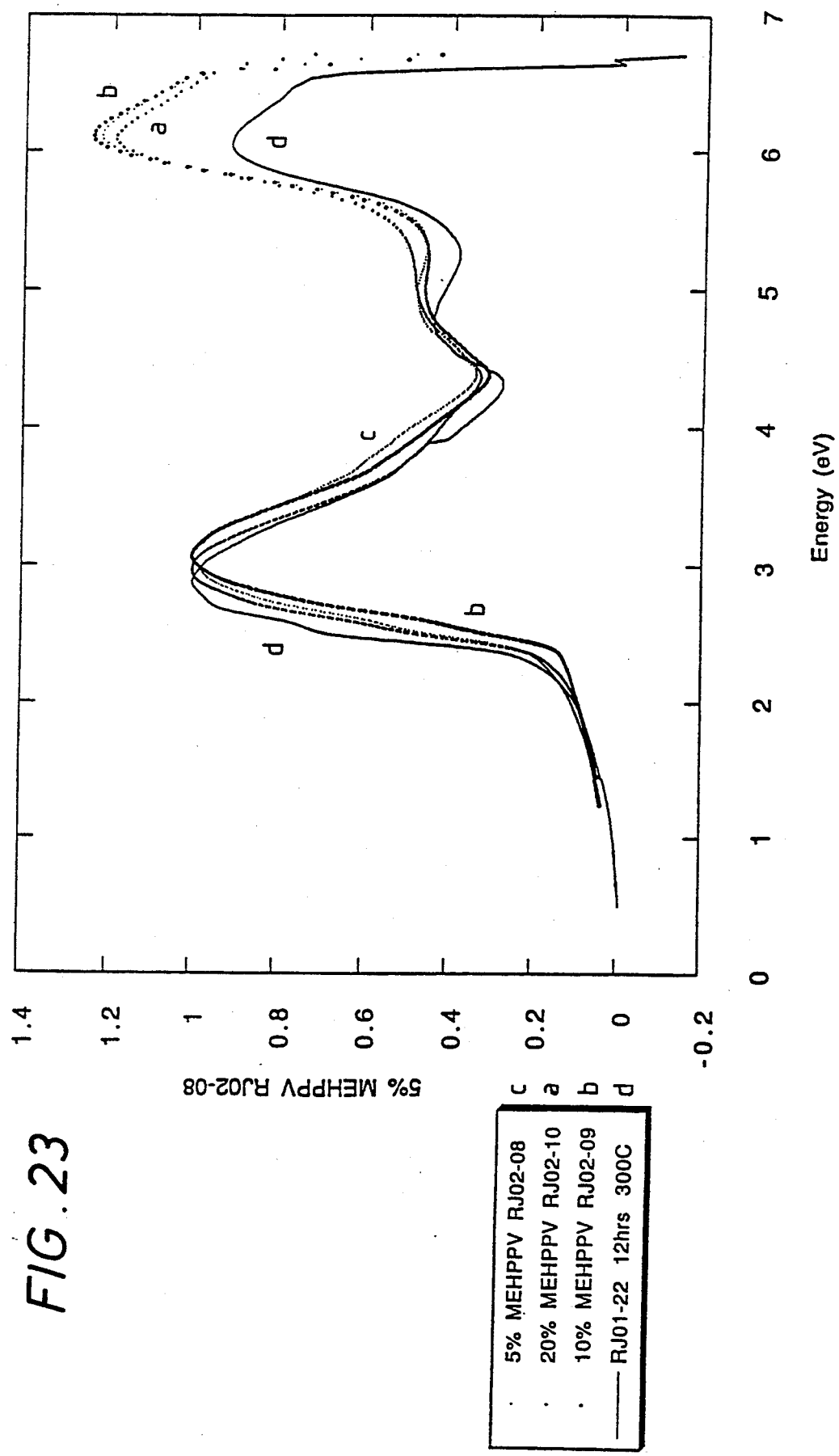
FIG. 23 is a graph showing the absorption spectra of spin-coated thin films of random copolymers of PPV and MEH-PPV produced from 80:20, 90:10, 95:5 and 100:0 w/w ratios of PPV and MEH-PPV monomer units, respectively as converted at 220° C. in vacuo for 12 hours.

In order to characterise more fully the nature of the resulting copolymers the absorption spectra were obtained from samples which had been spun onto glass under the same conditions as discussed below for the construction of devices (step (c)) and subsequently thermally converted side by side with the corresponding devices (step (d)). The results thus provide a direct insight into the effect upon the polymer electronic structure of the copolymer composition. FIG. 2a shows a set of spectra for the compositions of the copolymers (of general structure II with R=OCH$_3$) of para-phenylene vinylene, 2,5-dimethoxy-para-phenylene vinylone and unconverted precursor units that have been investigated in device structures and whose performance is exemplified below. The spectra have all been scaled to the same peak absorption to allow a ready comparison of the onsets for their $\pi$ to $\pi^*$ optical transitions and the energies of their absorption peaks. Also shown for comparison is the absorption spectrum of the PDMOPV homopolymer obtained as previously shown in "Polyarylene vinylene films prepared from precursor polymers soluble in organic solvents" S Tokito et al, Polymer 31, 1137 (1990). There is a clear trend in these spectra that the energy of the absorption peak shifts to higher energy as the relative content, in the precursor copolymer (structure I with R=OCH$_3$ and R$^1$, R$^2$=—(CH$_2$)$_4$—) of units of the precursor to 2,5-dimethoxy-para-phenylene vinylene is increased. This behaviour is contrary to expectation for a fully conjugated copolymer since as discussed above and shown in FIGS. 2a and 2b, PDMOPV has a lower energy gap than PPV. In FIG. 2a, curve (a) is 100% PPV, (b) is 95% PPV/5% PDMOPV, (c) is 90% PPV/10% PDMOPV, (d) is 85% PPV/15% PDMOPV, (e) is 80% PPV/20% PDMOPV and (f) is 70% PPV/30% PDMOPV. Similarly this has been observed with 95% PPV/5% MMP-PPV, 90% PPV/10% MMP-PPV and 80% PPV/20% MMP-PPV (FIG. 19) and with 95% PPV/5% MEH-PPV, 90% PPV/10% MEH-PPV and 80% PPV/20% MEH-PPV (FIG. 23). The data is however consistent with incomplete conversion of the precursor units during the thermal treatment, resulting in remnant non-conjugated sequences that interrupt the—electron delocalisation (structure II with R=OCH$_3$), limiting the effective conjugation length and thus increasing the to * transition energy. These remnant sequences are mostly associated with the precursor to 2,5-dimethoxy-para-phenylene vinylene however, there can also be methoxy leaving groups associated with the precursor to PPV, i.e. the methoxy leaving group precursor polymer to PPV, which will not be fully eliminated by thermal treatment (structure II with R=OMe). The Lack of conversion of the methoxy precursors to 2,5-dimethoxy-para-phenylene vinylene and to para-phenylene vinylene under the thermal conversion procedure utilised here is ascribable to the difficulty of elimination of the methoxy leaving group, previously shown in "Polyarylenevinylene films prepared from precursor polymers soluble in organic solvents" S. Tokito, T. Momii, H. Murata, T. Tsutsui and S. Saito, Polymer 31, 1137 (1990) to require acid catalysis for its full removal. It should be emphasised that while the conversion of the precursors to PPV does in fact liberate acid as one of its by-products, in thin film copolymer samples converted by heating in vacuo the acid is too rapidly removed to be effective in driving the conversion of the precursor to 2,5-dimethoxy-para-phenylene vinylene to completion. In thick film samples prepared by static solution casting, however, the extent of conversion of the methoxy precursors is significantly enhanced. This is clearly evidenced in their colour (they are unfortunately too thick for optical absorption measurements) which, unlike the uniformly yellow thin film samples becomes increasingly red as the content of the precursor to 2,5-dimethoxy-para-phenylene vinylene in the copolymers increases. It is also evidenced by the decrease of the strength, during conversion, of the characteristic C-O stretch vibration in the infrared spectra that is associated with the methoxy modifier group on the benzylic carbon of the methoxy precursors to 2,5-dimethoxy-para-phenylene vinylene and para-phenylene vinylene. This behaviour can be understood as being due to the lower rate of loss of acid from the bulk of thick films, allowing greater interaction with the units of the methoxy precursors and consequently a greater extent of their conversion. Further evidence supporting these differences between the thin, spin-coated films and thicker solution cast films comes from their photoluminescence spectra. Discussion here is limited to the representative cases of the copolymers obtained following thermal conversion of thin spin-coated and thick solution cast films of the copolymer precursors prepared from (1) 10% of units of the precursor to 2,5-dimethoxy-para-phenylene vinylene/90% of units of the precursor to para-phenylene vinylene and (2) 20% of units of the precursor to 2,5-dimethoxy-para-phenylene vinylene/80% of units of the precursor to para-phenylene vinylene. In FIG. 3(a) and (b) are shown respectively the emission spectra for thin spin-coated and thick solution cast films for case (1). In FIG. 4(a) and (b) are shown the corresponding spectra for case (2). For comparison FIGS. 5(a) and (b) show the photoluminescence spectra for the PPV and PDMOPV homopolymers; the latter prepared via acid catalysed thermal conversion under HCl containing nitrogen gas flow so as to ensure substantial, if not wholly complete, conversion of the precursor units. It is immediately clear from the spectra in FIGS. 3 and 4 that in vacuo thermally converted spin-coated thin films have significantly different emission spectra to the thicker films obtained under identical conversion conditions and from the same precursor solutions but following static solution casting. Furthermore, whilst the spectra of the thin spin-coated samples have spectra which lie at higher energy than in PPV (FIG. 5(a)), the thicker static solution cast samples show spectra that are red shifted relative to PPV and hence that are shifting towards the emission spectrum seen in PDMOPV (FIG. 5(b)).

It is thus clear that the electronic structures of the copolymers that are incorporated into device structures may be controlled by the selection of the constituent components present in the copolymer precursor and by the conversion conditions used in device fabrication. Changing some of the units of the precursor to para-phenylene vinylene to units of the precursor to 2,5-dimethoxy-para-phenylene vinylene can have two different effects depending on whether conversion is purely thermal or also involves acid catalysis. For purely thermal conversion there is an incomplete elimination such that the resultant conjugated segments are separated by remnant non-conjugated precursor units, causing the energy gap to increase relative to that of homopolymer PPV and the photoluminescence emission to be blue shifted, occuring at higher energy than in PPV. For acid catalysed thermal conversion the elimination is substantially complete with the result that the energy gap decreases and photoluminescence emission shifts to the red.

Figure 6:
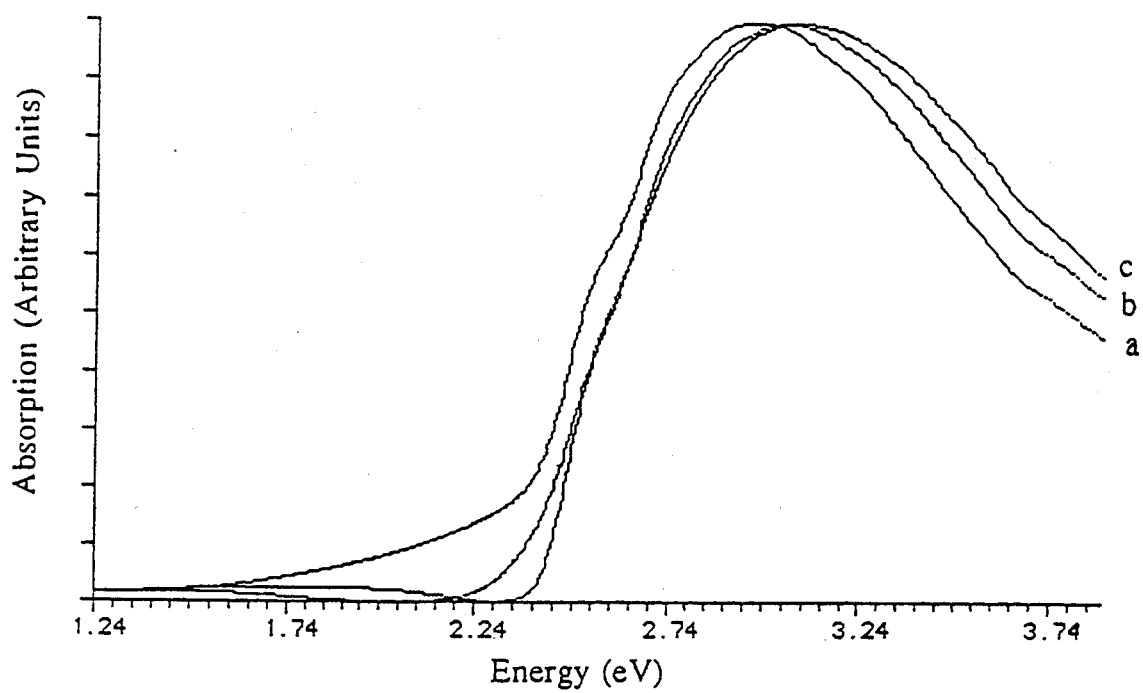
FIG. 6 is a graph showing respectively the absorption spectra of a homopolymer of PPV, and random copolymers of PPV and PTV produced respectively from 19;1 and 9:1 molar ratios of PPV and, PTV monomer units, converted at 220° C. in vacuo for two hours.
Figure 7A:
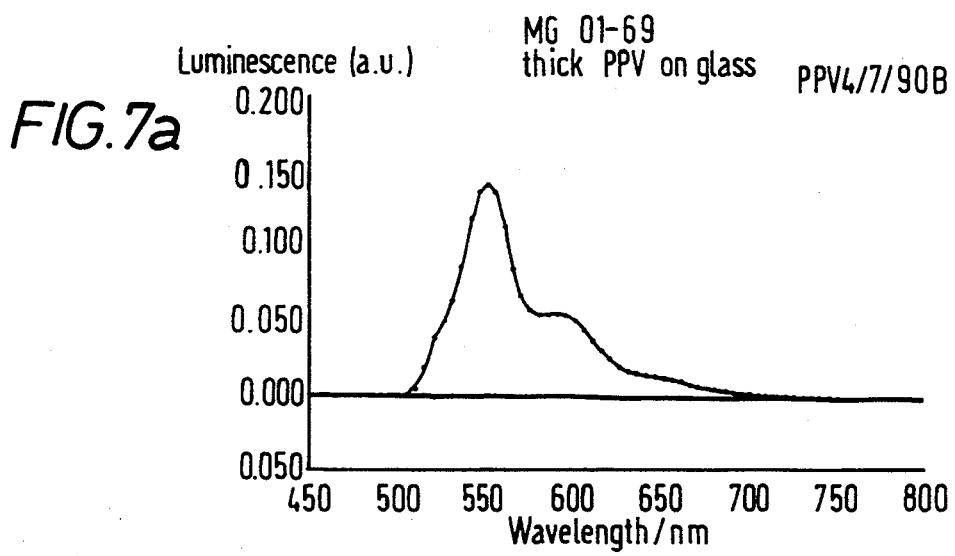
FIGS. 7a, b and c are graphs showing respectively the photoluminescence emission spectra for thick free cast films of a homopolymer of PPV; a copolymer produced from a 19:1 molar ratio of PPV and PTV monomer units respectively; and a copolymer produced from a 9:1 molar ratio of PPV and PTV monomer units respectively.
Figure 7B:
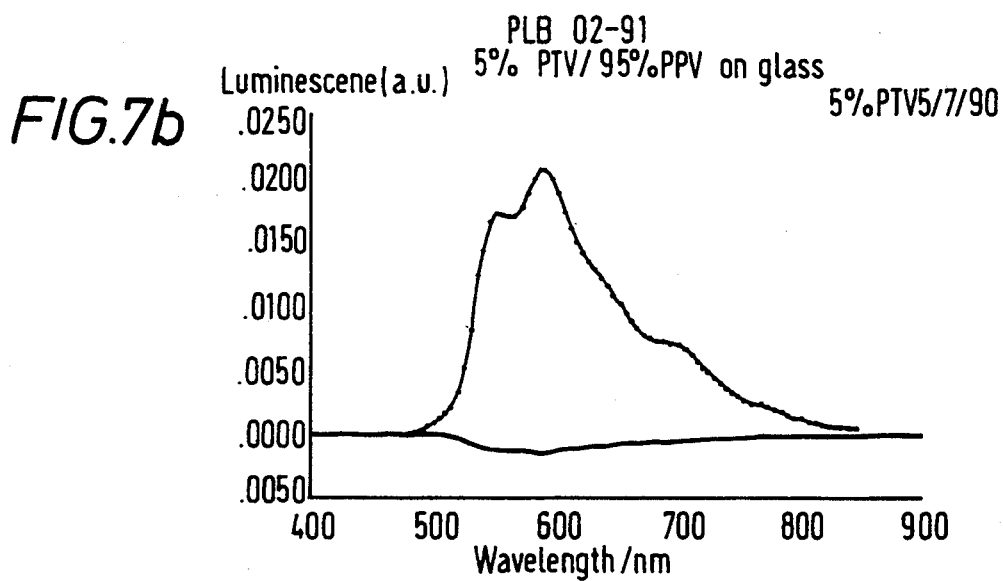
Figure 7C:
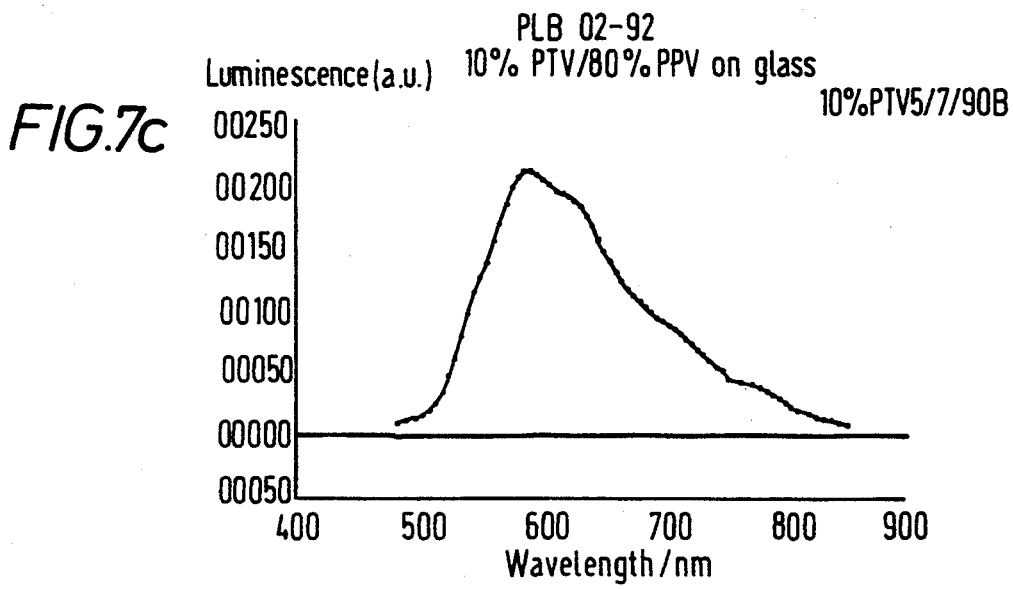

A similar situation arises in the case of the copolymers of the precursor to para-phenylene vinylene and the precursor to 2,5-thienylene vinylene (structure II with R=H and R'—CH$_3$) with the absorption spectra of thin spin-coated films of in vacuo thermally converted copolymers showing a shift in the position of the absorption peak to higher energy than seen in PPV (see FIG. 6) whilst the photoluminescence emission spectra for thick solution cast films converted under identical conditions show a red shift relative to that in PPV (see FIG. 7 (a), (b) and (c)). In FIG. 6, curve (a) is 100% PPV, (b) is 95% PPV/5% PTV and (c) is 90% PPV/10% PTV. Thus, the conversion of methoxy modifier group precursor units of 2,5-thienylene vinylene is enhanced in thick films by acid catalysed elimination driven by the acid by-product of the para-phenylene vinylene sulphonium salt-precursor conversion. It was previously reported in "Optical Excitations in Poly(2,5-thienylene vinylene)" A. J Brassett, N. F. Colaneri, D. D. C. Bradley, R. A. Lawrence, R. H, Friend, H. Murata, S. Tokito, T. Tsutsui and S. Saito, Phys. Rev. B 41, 10586 (1990) that the photoluminescence emission from the PTV homopolymer obtained by acid catalysed thermal conversion of the methoxy leaving group precursor polymer is extremely weak (with quantum yield less than or of order $10^{-5}$) and, when it can be observed, appears at energies above the onset for $\pi$ to $\pi^*$ optical transitions.

Figure 8:
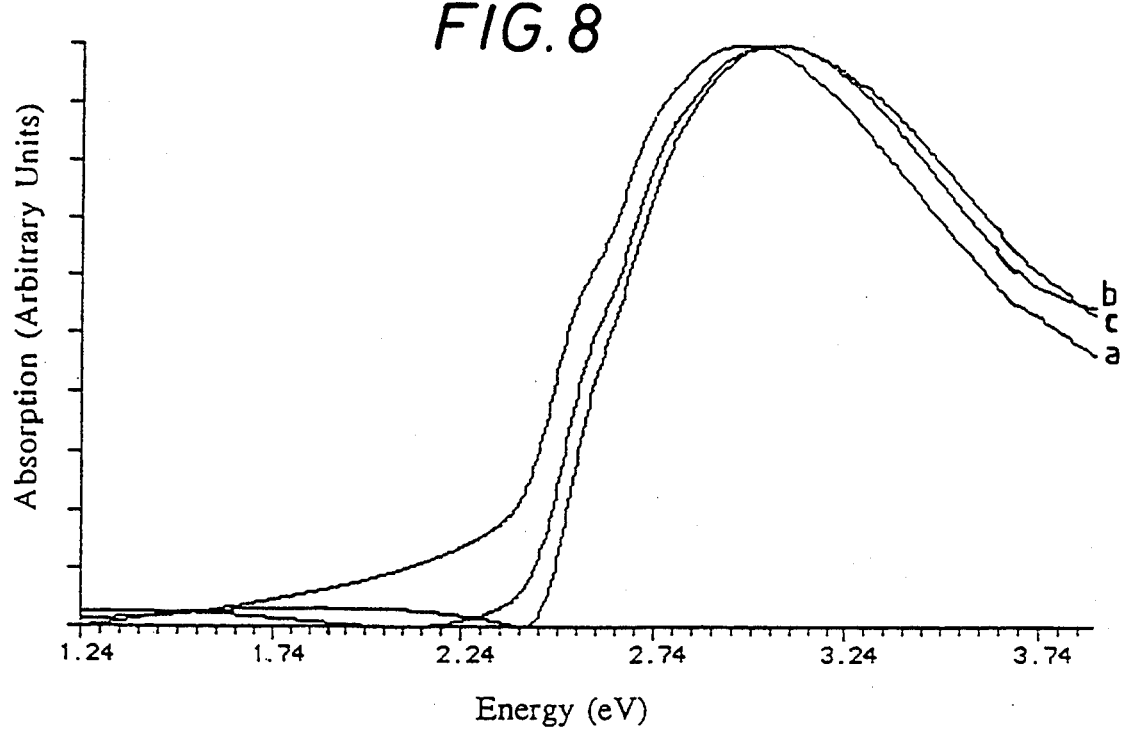
FIG. 8 is a graph showing the absorption spectra of spin-coated thin films of a homopolymer of PPV, and random copolymers of PPV and dimethyl PPV produced respectively from 19;1 and 9:1 molar ratios of PPV and PTV dimethyl monomer units as converted at 220° C. in vacuo for two hours.
Figure 9A:
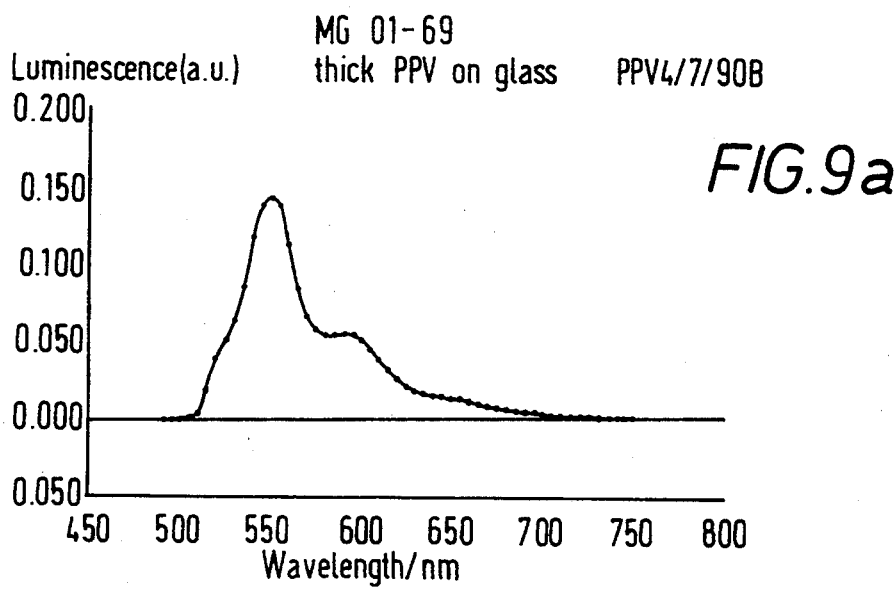
FIGS. 9a, b and c are graphs showing respectively the photoluminescence emission spectra of thick free cast films for the homopolymer of PPV; a copolymer produced from a 19:1 molar ratio of PPV and dimethyl PPV monomer units respectively; and a copolymer produced from a 9:1 molar ratio of PPV and dimethyl-PPV monomer units respectively.
Figure 9B:
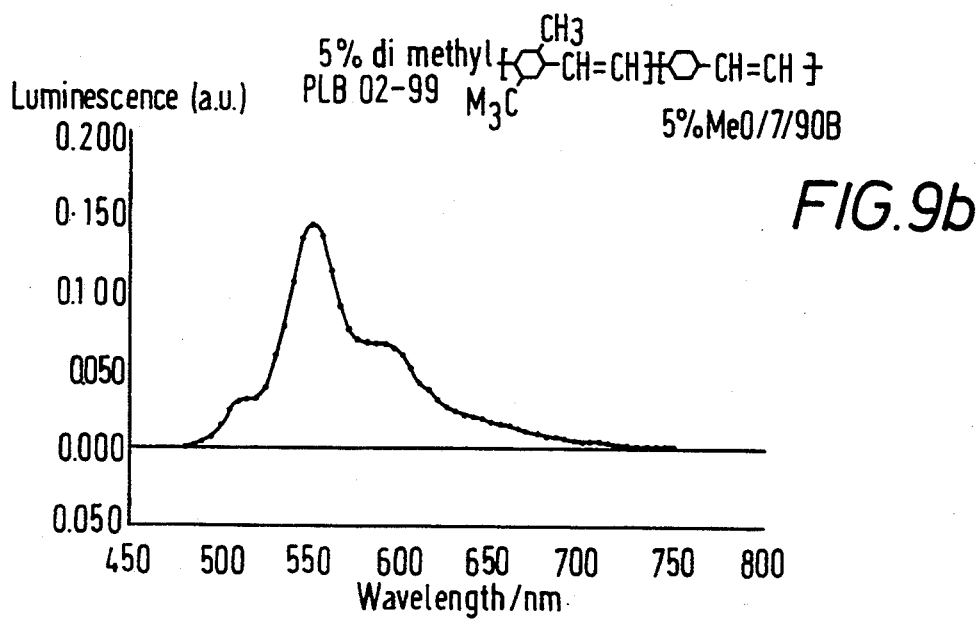
Figure 9C:
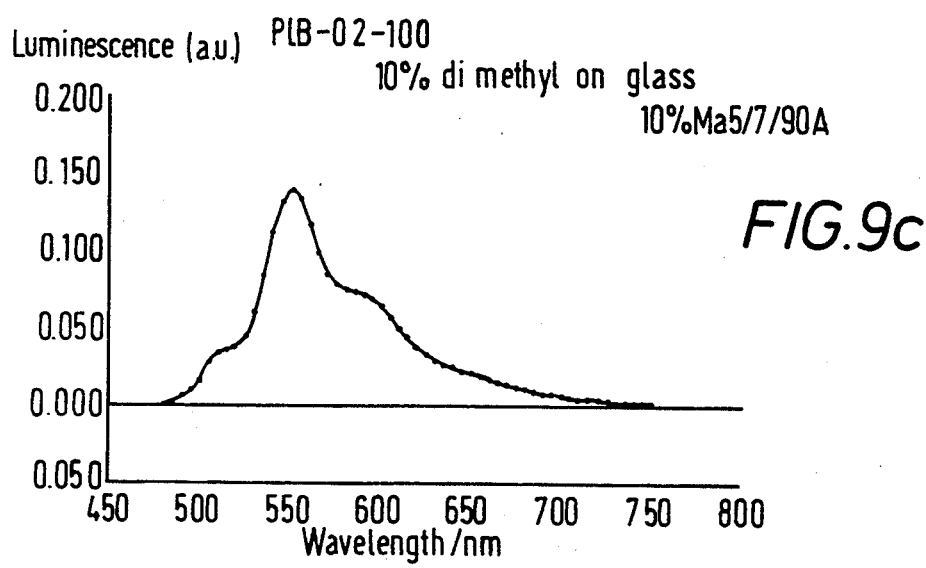

In the copolymers of the precursors to para-phenylene vinylene and 2,5-dimethyl-para-phenylene vinylene (structure (I) with R=OCH$_3$ and R$^1$, R$^2$=—(CH$_2$)$_4$—) the absorption spectra of in vacuo thermally converted thin spin-coated samples show a shift in the position of the absorption peak to higher energy than seen in PPV (see FIG. 8) whilst the photoluminescence emission spectra for thick solution cast films converted under identical conditions show little shift relative to that in PPV (see FIG. 9(a), (b) and (c)). In FIG. 8, curve (a) is 100% PPV, (b) is 95% PPV/5% DMPPV and (c) is 90% PPV/10% DMPPV. The explanation of the higher bandgap energy observed in the absorption spectra of the thin spin-coated samples is that the as-formed copolymer contains disruption in the conjugation due either to steric interactions of the methyl group with the vinylic proton twisting the sp$^2$-$\pi$-orbitals of the dimethyl-para-phenylene and the adjacent vinylene units out of planarity or that in the absence of acid catalysed conversion, the elimination of methoxy leaving groups from the methoxy precursors to 2,5-dimethyl-para-phenylene vinylene and para-phenylene vinylene is incomplete, thus resulting in a copolymer structure containing conjugated segments separated from each other by unconverted non-conjugated precursor units or a combination of both.

The inventors have trapped some of the acid released from a thin film during thermal conversion by capping a section of a film of the 10% dimethoxy-PPV/90% PPV precursor polymer which had been spin coated onto a glass silide (about 2.5 cm square) with a strip of evaporated aluminium (about 4 mm wide) before heat treatment. The precursor was then heated as described above to leave a film of thickness 100 nm and the aluminium was removed using dilute aqueous sodium hydroxide. There was a clear difference in colour between the area previously coated with aluminium (orange) and that where there had been no aluminium (yellow). The optical absorption spectra for the two areas are shown in FIG. 16 from which it can be seen that there is a shift in band gap towards the red of about 0.2 eV for the area previously coated with aluminium. The photoluminescent spectra for the two regions are shown in FIG. 17. This shows that we can control the extent of conjugation in different regions of, the same polymer film so as to produce different emission colours from these different regions.

Fabrication of Electroluminescent (EL) structures

Structures for an EL device require two electrodes to either side of the emissive region. For the examples shown here, devices have been fabricated by deposition of a series of layers onto a transparent substrate (glass), but other structures can also be made, with the active (i.e. emissive) area being defined by patterning within the plane of the polymer film.

The choice of electrode materials is determined by the need to achieve efficient injection of charge carriers into the polymer film, and it is desirable to choose materials which preferably inject electrons and holes as the negative and positive electrodes respectively. In International Patent Application No. PCT/GB90/00584 (Publication No. PCT/WO9013148) is described the use of PPV as the emissive layer, and a choice of aluminium, amorphous silicon, silver/magnesium alloy as the negative electrode, and aluminium with a thin oxide coating, gold and indium oxide as the positive electrode. Many of these combinations were found to be satisfactory. In the present disclosure, where many different compositions of copolymers have been investigated, the choice of contact layers has been generally for convenience that of aluminium for the negative electrode and aluminium with an oxide coating as the positive electrode. Calcium has also been used as the negative electrode with indium/tin oxide as the positive electrode. It is to be expected that results obtained with this combination give a good indication of the behaviour to be expected with other choices for electrode materials:

The procedure used for all devices Used in this work is as follows:

(a) Clean glass substrates (microscope slides) in propan-2-ol reflux.

(b) Deposit bottom contact of aluminium by evaporation of aluminium in a standard vacuum evaporator (base pressure $2 \times 10^{-6}$ mbar). Four strips 1 mm wide were usually deposited, and the aluminium film thickness was chosen to give a conducting but semi-transparent film (9-12nm). The aluminium was then exposed to air at room temperature, to allow formation of a surface oxide coating.

(c) Deposition of the precursor polymer from solution in methanol by spin-coating, using a Dyna-Pert PRS14E spin-coater. This was performed inside a laminar-flow cabinet, with a spin speed of 2000 rev/min, and produced films of polymer in the thickness range 50-150 nm.

(d) Thermal treatment of the precursor, to convert to the conjugated polymer. This was carried out in an evacuated oven (base pressure $10^{-5}$ mbar) inside an argon-atmosphere glove box. The heat treatment used was 30 min to heat to 220° C., between 2 and 5 hours at 220° C., and 3 hours to cool to room temperature.

(e) Evaporation of aluminium top contact, carried out as in (b) above, but with the 1 mm wide strips rotated by 90°, to give a total of 16 independently addressable devices, each 1 mm². The aluminium thickness here was typically 50 nm, to ensure a good coverage, and to provide some encapsulation to keep oxygen away from the active parts of the device.

Measurements of Devices

Positive bias was applied to the bottom contact (aluminium with surface oxide coating) using a programmable voltage source (Keithley model 230). The current through the device was measured with a Keithley model 195 DVM connected between the top contact and ground. The light output was measured with a large area silicon photovoltaic cell (1 cm² active area, Radio Spares catalogue number RS 303-674).

Figure 10A:
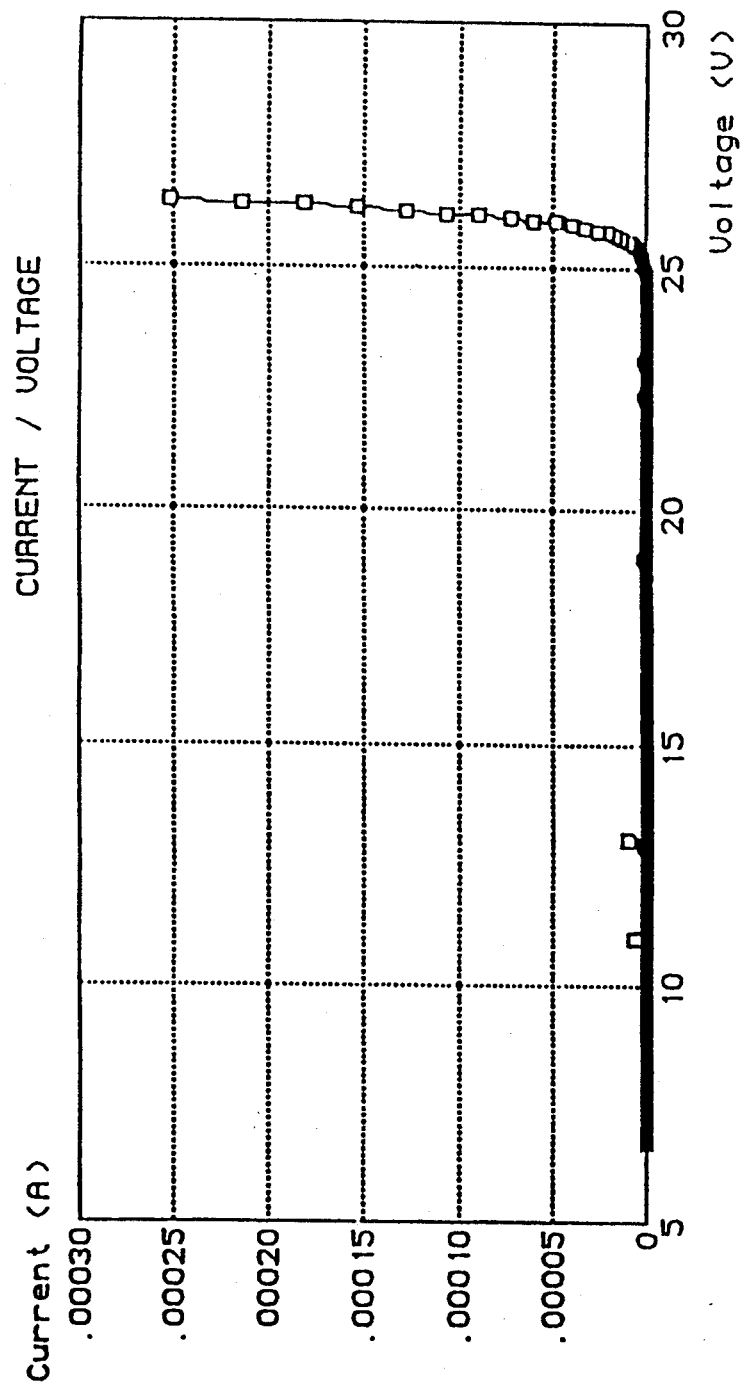
Figure 10B:
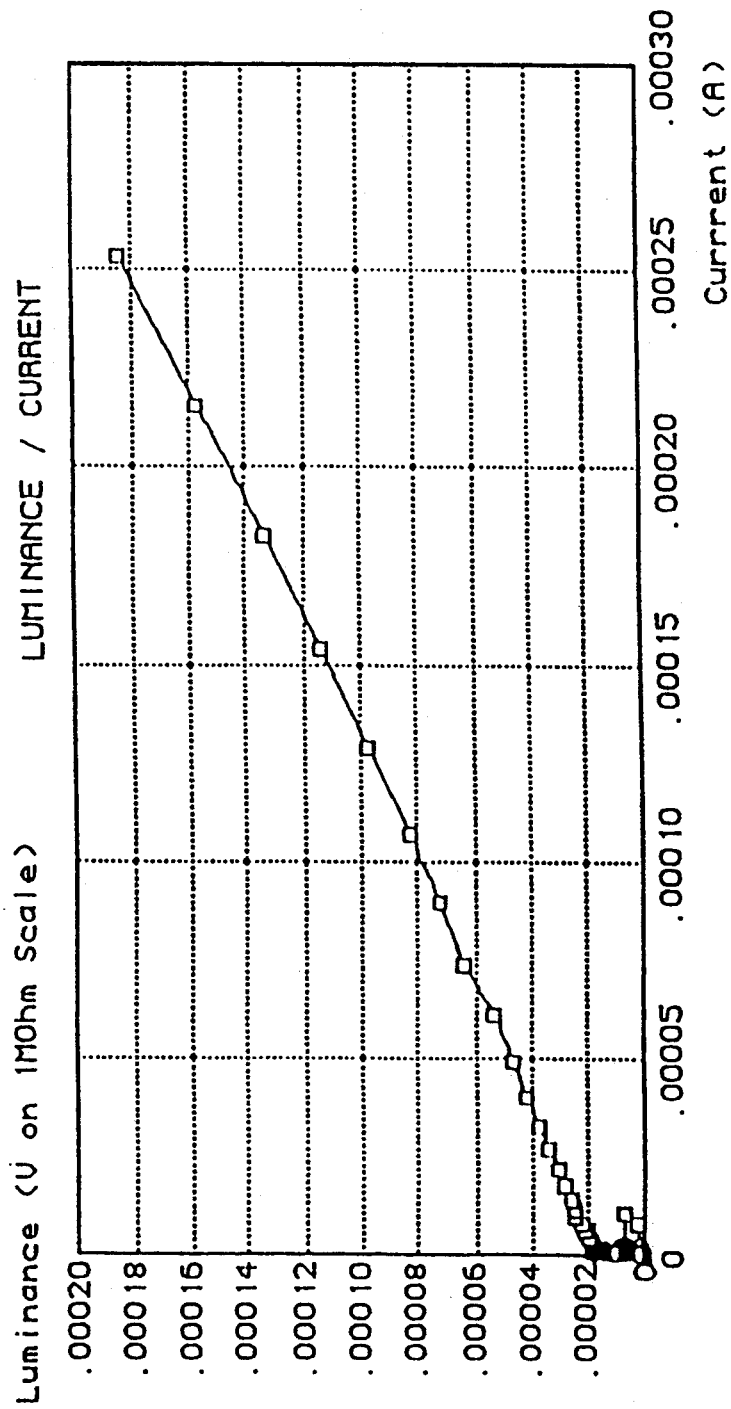
Figure 12A:
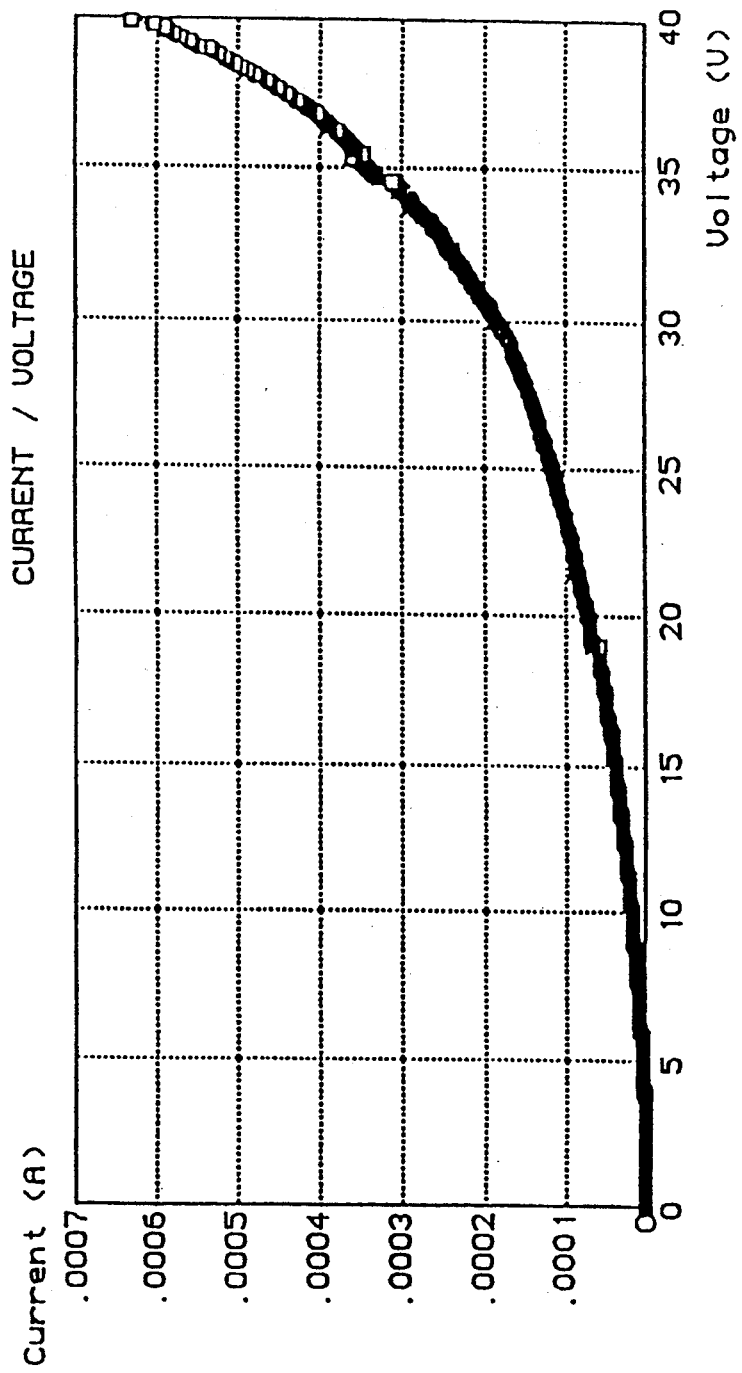
Figure 12B:
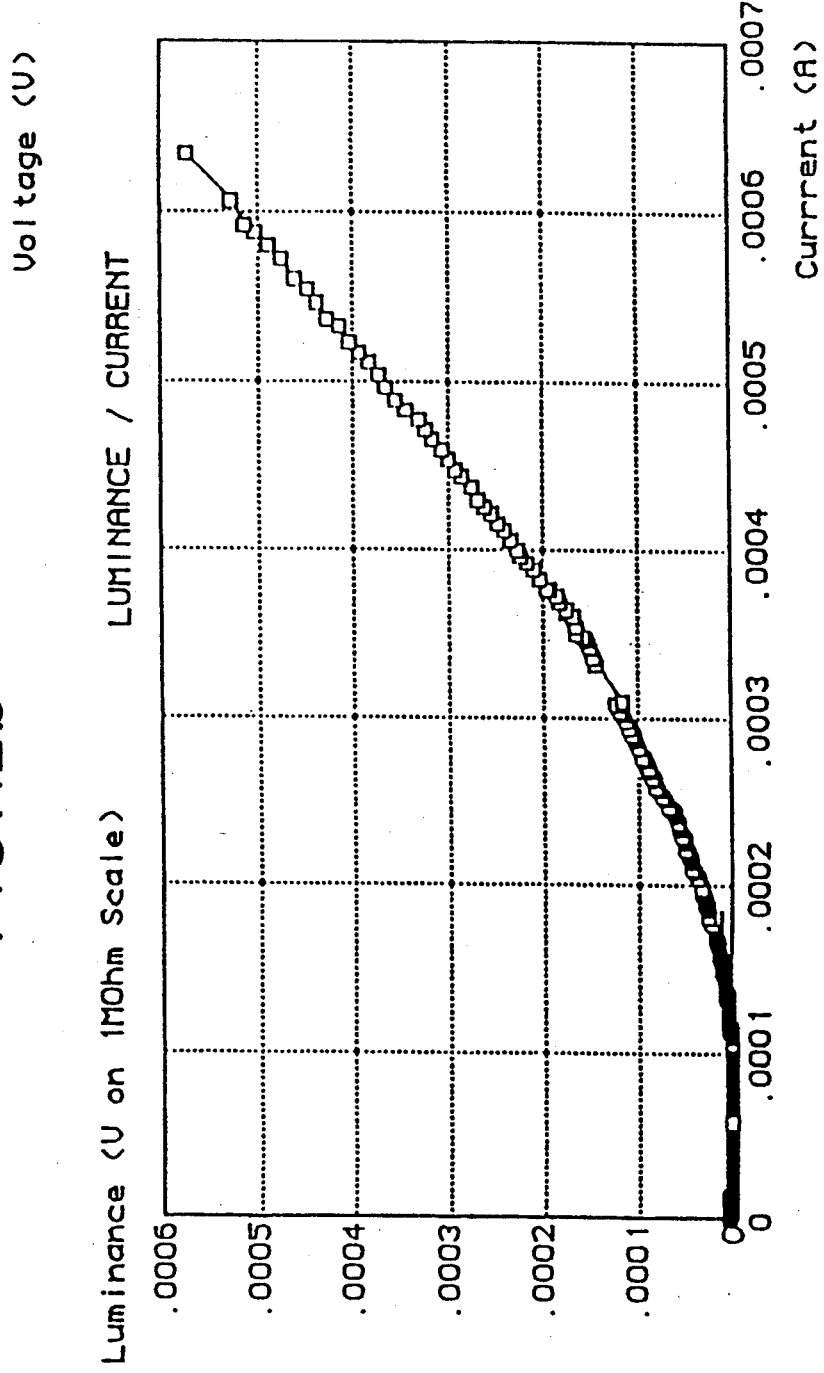
Figure 13:
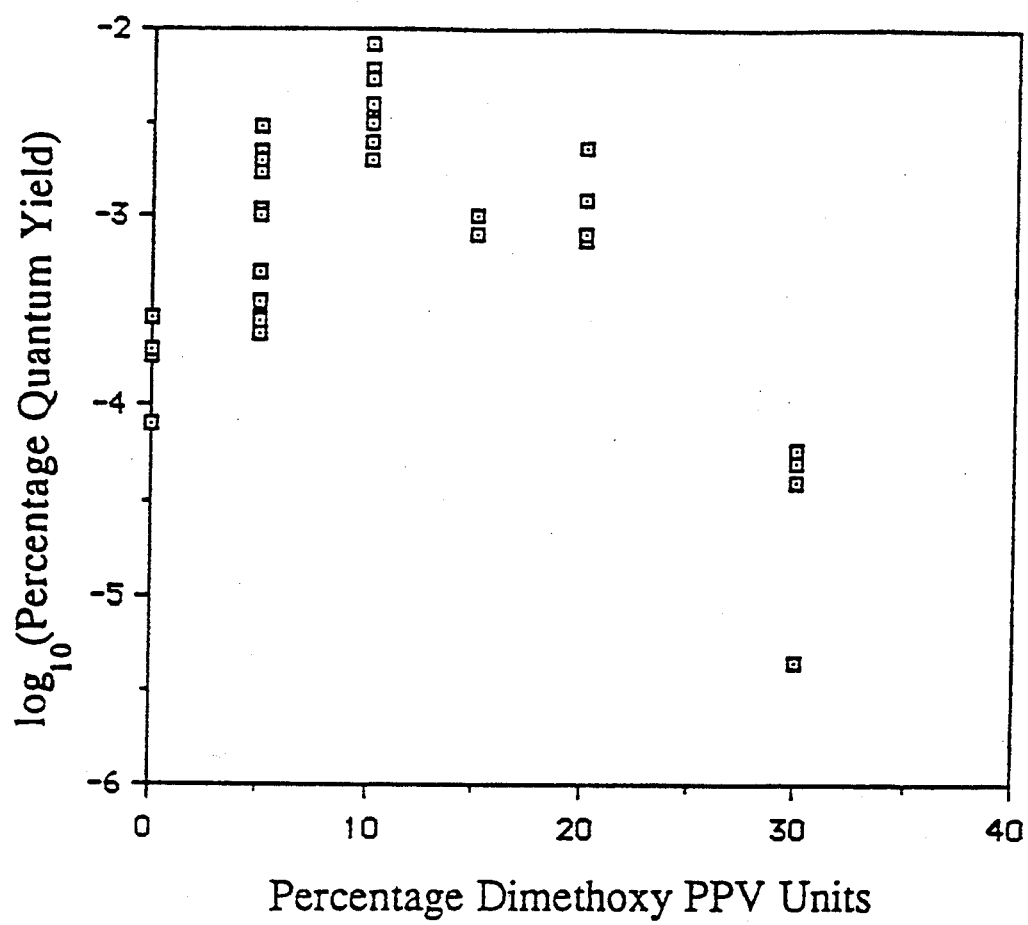
FIG. 13 illustrates the electroluminescent quantum yield of random copolymers formed from PPV and dimethoxy-PPV monomer units as measured in thin film structures with hole injecting electrodes of oxidised aluminium, a spin-coated film converted at 220° C. in vacuo for two hours, and with electron injecting electrodes of aluminium.
Figure 14:
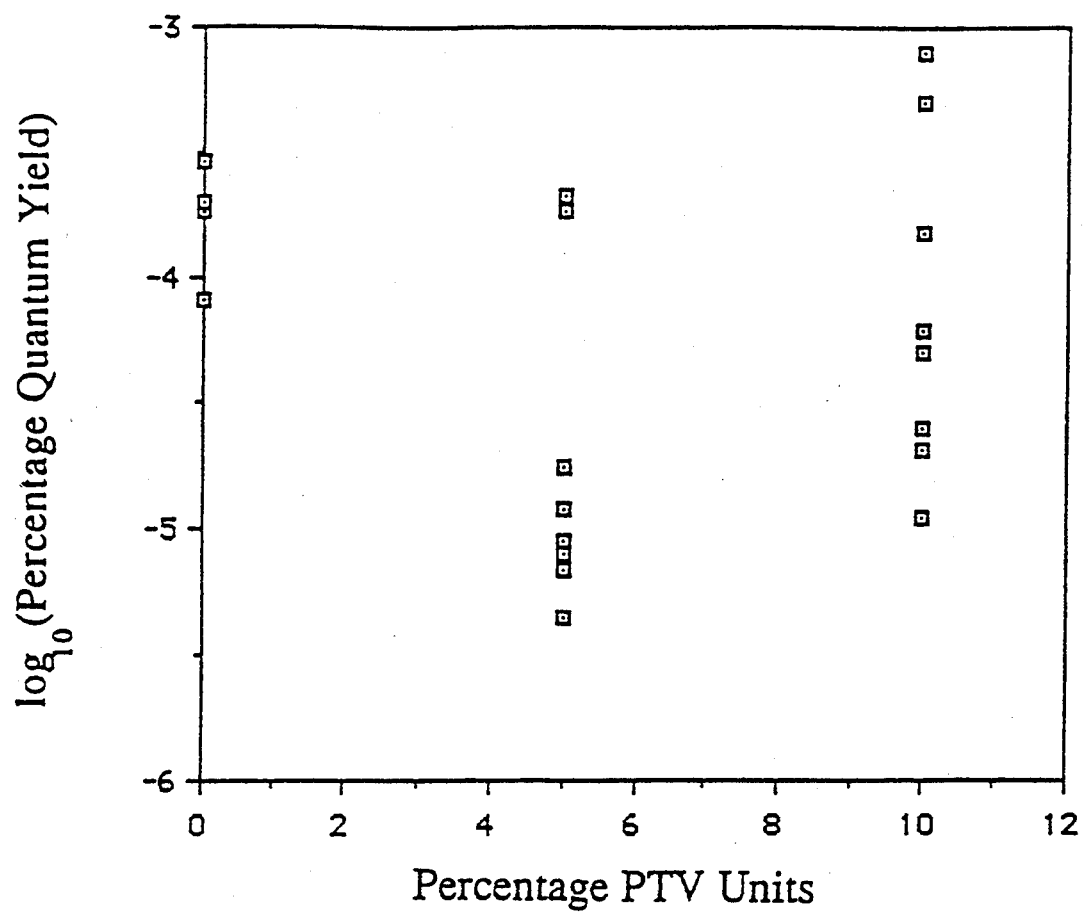
FIG. 14 illustrates the electroluminescent quantum yield of random copolymers formed from PPV and PTV monomer units as measured in thin film structures with hole injecting electrodes of oxidised aluminium, a spin-coated film converted at 220° C. in vacuo for two hours, and with electron injecting electrodes of aluminium.
Figure 15:
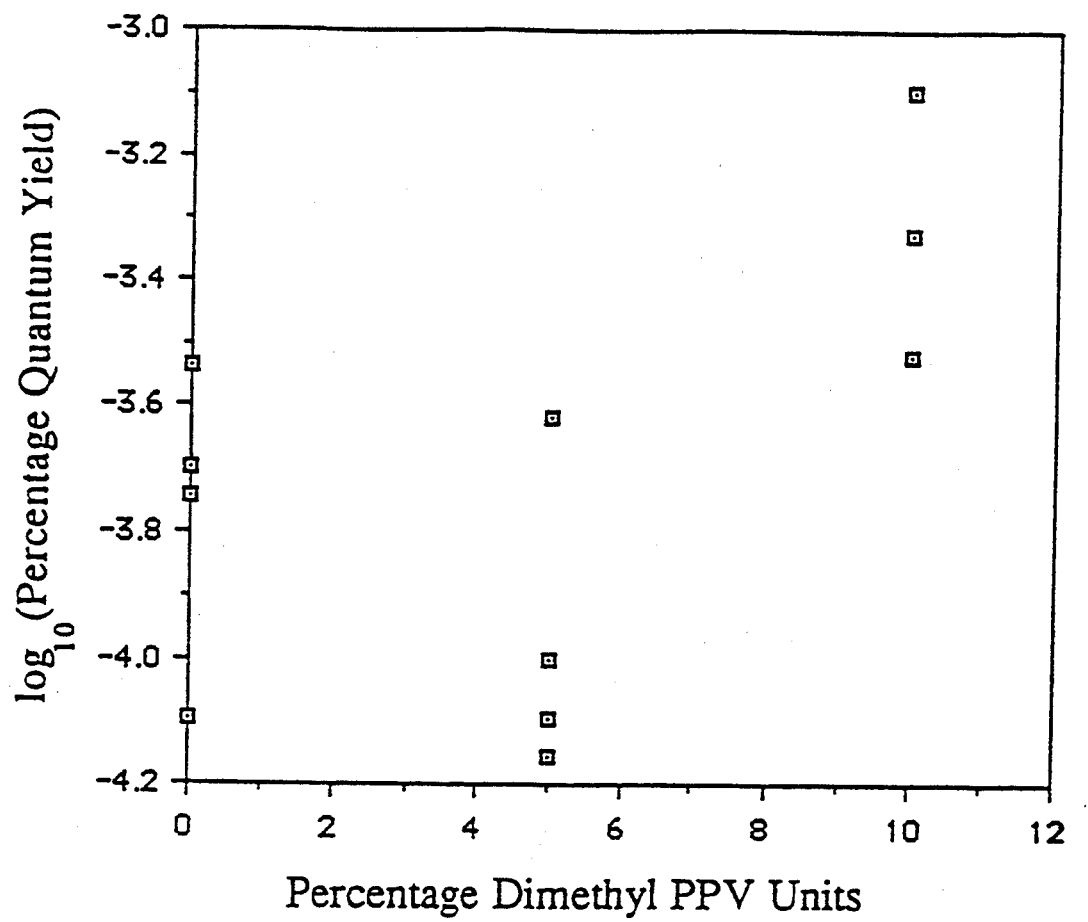
FIG. 15 illustrates the electroluminescent quantum yield of random copolymers formed from PPV and dimethyl-PPV monomer units as measured in thin film structures with hole injecting electrodes of oxidised aluminium, a spin-coated film converted at 220° C. in vacuo for two hours, and with electron injecting electrodes of aluminium.

Typical results of the PPV homopolymer, a copolymer obtained by in vacuo thermal conversion of spin-coating thin films of spin coated films of a precursor copolymer synthesised from 90% para-phenylene vinylene/10% 2,5-dimethoxy-para-phenylene vinylene precursor units, a copolymer obtained by in vacuo thermal conversion of spin-coated thin films of a precursor copolymer synthesised from 90% para-phenylene vinylene/10% 2,5-thienylene vinylene precursor units and a copolymer obtained by in vacuo thermal conversion of spin-coated thin films of a precursor copolymer synthesised from 90% para-phenylene vinylene/10% 2-methoxy-5-(2'-methylpentyloxy)-para-phenylene vinylene precursor Units are shown in FIGS. 10, 11, 12, 20 and 21 which present the current versus voltage and light output versus current characteristics. In FIG. 10 the bottom contact thickness is 110A, the top contact thickness is 1300A and the thickness of the electroluminescent layer is 900A. In FIG. 11 the corresponding thickness values are 120A, 1000A and 1450A and in FIG. 13 they are 90A, 1370A and 1070A. Similar current versus voltage characteristics were found for all devices, with a threshold voltage for current injection of around 25 to 40V. There was also found a broadly linear relation between current and light output (which allows the efficiency of the device to be characterised simply, by the gradient of this plot).

It is found that the light output varies strongly with the choice of copolymer, and that some of the copolymers show very strongly enhanced efficiencies as measured against the efficiency of the PPV homopolymer. The variation of the quantum efficiency is shown as actually measured (current in photodetector/current through EL device) in FIGS. 13, 14, 15 and 31 for the copolymers obtained from the in vacuo thermal conversion of spin-coated thin films of precursor copolymers formed between the precursors to PPV and PDMOPV, the precursors to PPV and PTV, the precursors to PPV and PDMPV, and the precursors to PPV and MMP-PPV respectively. The plots show some data for a large number of devices, and there is some scatter evident between devices of the same nominal composition. This may be due to inhomogeneities in the devices, such as non-uniform thickness, entrapped dust particles etc. and it is considered that the better values of efficiency at each composition give a true indication of the intrinsic behaviour of the EL structure. The PPV/PDMOPV copolymers show a very big improvement in efficiency for PDMOPV in the range 5-15%, with best results at 10%, for which the improvement over that obtained for PPV is by a factor of about 50. The PPV/PTV copolymers do not show such behaviour. This may be compared with the very low quantum yield for photoluminescence (less than or of order $10^{-5}$) that is found in the homopolymer, as in "Optical Excitations in Poly(2,5-thienylene vinylene)" A. J. Brassett, N. F. Colaneri, D. D. C. Bradley, R. A. Lawrence, R. H. Friend, H. Murata, S. Tokito, T. Tsutsui and S. Saito, Phys. Rev. B 41, 10586 (1990). For the PPV/PDMPV copolymers an improvement over the PPV homopolymer is seen at 10% PDMPV, but the changes are less marked than with the PPV/PDMOPV copolymers.

The maximum measured efficiencies for the devices shown here, obtained for the 90/10% PPV/PDMOPV copolymer, approach $10^{-2}$%. To obtain the real efficiency of the EL layer in the device it is necessary to correct for the efficiency of the photodetector (50%), the collection efficiency for the EL (24%) and the optical transmittance of the Al semitransparent layer (30%). With these factors included, it is estimated that the real efficiency of the EL layer in such a device is as high as 0.3%. This value compares very favourably with the performance of EL devices fabricated with other materials.

As PL and EL are due to the same excited state in the polymer, as evidenced by the similarity in emission recorded for a single polymer film, a correspondence between efficiency for EL and for PL is broadly to be expected. However, there are some differences as discussed below.

The efficiency for luminescence is in part an intrinsic property of the material (that is to say that it has the same value for all samples), and possibly also dependent on the actual form of the sample and the nature of the interfaces to it. Thus, it might be expected for the thin films used for the EL structures that migration of the excited states to the interface between the polymer film and the electrode material might result in non-radiative decay of the excited state, and thus allow the efficiency for luminescence to fall below its "intrinsic" value. The effect, then of restricting the motion of the excited states in the copolymers may be to improve quantum yield both by improving the intrinsic properties of the polymer, and also by reducing the motion of excited states to the interface region. Thus., the improvements in quantum yield that have been measured in EL for some of the copolymers are by a very large factor (×50), considerably larger than the factor by which the yield for PL is improved.

There has been described a design technique and a method of manufacture for achieving especially efficient emission in conjugated copolymer electroluminescent structures through the use of the local modulation of semiconductor energy gap, between the highest occupied and lowest unoccupied energy levels, achieved in copolymers of two or more different monomer units. The modulation of energy gap is achieved by the use, in the copolymer structure, of chemically-different monomer units which in their individual homopolymer forms have different energy gaps. The effect of the energy gap modulation is to produce local regions that are potential energy minima and that act to confine the exciton states created by injection of electrons and holes from the contact layers. This confinement is beneficial for efficient radiative recombination of excitons through its reduction of the opportunities for migration of the excitons to non-radiative recombination sites subsequent to their initial generation and thus leads to a higher electroluminescent yield.

The copolymers described herein are intractable, insoluble in common solvents and infusible at temperatures below the decomposition temperature, or they are soluble in a few organic solvents.

It is claimed:

1. A semiconductive conjugated film forming copolymer comprising: at least two chemically different monomer units each having different semiconductor bandgaps in their individual homopolymer forms, wherein the proportion of said at least two chemically different monomer units in the copolymer forms the copolymer with a semiconductor bandgap that is spatially modulated from the semiconductor bandgap of each homopolymer form so that the optical properties of the copolymer are modulated, said copolymer being capable of forming a film without substantially affecting the luminescent characteristics of the copolymer, said copolymer being stable at operational temperatures within the range of about 0° C. to 150° C.

2. A copolymer as claimed in claim 1, wherein the semiconductor bandgap of the copolymer has been spatially modulated so as to modulate the optical properties of the copolymer by increasing the quantum efficiency of the copolymer when excited to luminesce.

3. A copolymer as claimed in claim 1, wherein the semiconductor bandgap of the copolymer has been spatially modulated so as to modulate the optical properties of the copolymer by modulating the wavelength of radiation emitted during luminescence.

4. A copolymer as claimed in claim 1, wherein the semiconductor bandgap of the copolymer has been spatially modulated so that the optical properties of the copolymer are modulated by modulating the refractive index of the copolymer.

5. A copolymer as claimed in claim 1, wherein the chain of the copolymer is fully conjugated.

6. A copolymer as claimed in claim 1, wherein at least one of the monomer units is not fully conjugated in the chain of the copolymer.

7. A semiconductive copolymer as claimed in claim 1, wherein the proportion of said at least two chemically different monomer units are present in a molar ratio of about 4:1 to 19:1.

8. A conjugated semiconductive copolymer as claimed in claim 1 comprising an amount of poly(p-phenylene vinylene) in the range of about 90–95% and an amount of poly(2,5-dimethyl-phenylene vinylene) in the range of about 5–10%.

9. A conjugated semiconductive copolymer as claimed in claim 1, of poly(p-phenylene vinylene) and poly(p-phenylene 1-methoxy-1,2 ethanediyl) comprising at least 20% poly(p-phenylene vinylene).

10. A copolymer as claimed in claim 1, wherein at least one of the monomer units comprises an arylene vinylene unit substituted with a solubilizing group on the arylene ring so as to render the copolymer soluble in either aqueous or organic solvents.

11. A copolymer as claimed in claim 10, wherein the solubilizing group comprises an alkoxy group of at least four carbon atoms.

12. A copolymer as claimed in claim 11, wherein the alkoxy group is a 2-methylpentyloxy group or a 2-ethylhexyloxy group.

13. A conjugated semiconductive copolymer as claimed in claim 1, comprising an amount of poly(p-phenylene vinylene) in the range of about 90–95%, and an amount of poly(2-methoxy-5-(2'-methylpentyloxy)-p-phenylene vinylene in the range of about 5–10%.

14. A conjugated semiconductive copolymer as claimed in claim 1, comprising an amount of poly(p-phenylene vinylene) in the range of about 90–95%, and an amount of poly(2-methoxy-5-(2'-ethylhexyloxy)-p-phenylene vinylene in the range of about 5–10%.

15. A conjugated poly(arylene vinylene) film forming copolymer, comprising a poly(arylene vinylene) copolymer having a proportion of the vinylic groups of the copolymer saturated by inclusion of a modifier group substantially stable to elimination during formation of the film, wherein the proportion of saturated vinylic groups is effective to spatially modulate a semiconductor bandgap of the copolymer so as to modulate the optical properties of the copolymer, said copolymer being capable of forming a film without substantially affecting the luminescent characteristic of the copolymer said copolymer being stable at a temperature of about 0°–150° C.

16. A copolymer as claimed in claim 15, wherein the semiconductor bandgap of the copolymer has been spatially modulated so as to modulate the optical properties of the copolymer by increasing the quantum efficiency of the copolymer when excited to luminesce.

17. A copolymer as claimed in claim 15, wherein the semiconductor bandgap of the copolymer has been spatially modulated so as to modulate the optical properties of the copolymer by modulating the wavelength of radiation emitted during luminescence.

18. A copolymer as claimed in claim 15, wherein the semiconductor bandgap of the copolymer has been spatially modulated so as to modulate the optical properties of the copolymer by modulating the refractive index of the copolymer.

19. A copolymer as claimed in 15, wherein at least one of the arylene vinylene units is substituted with a solubilizing group on the arylene ring so as to render the copolymer soluble in organic or aqueous solvents.

20. A copolymer as claimed in claim 19, wherein the solubilizing group comprises an alkoxy group of at least four carbon atoms.

21. A copolymer as claimed in claim 20, wherein the alkoxy group is a 2-methylpentyloxy group or a 2-ethylhexyloxy group.

22. A conjugated poly(arylene vinylene) copolymer according to claim 15, which copolymer is formed by heating substantially in the absence of oxygen a poly(arylene-1,2-ethanediyl) precursor copolymer having a proportion of the ethane groups substituted with a modifier group substituent or a leaving group substituent, wherein the precursor copolymer is heated until substantially all of the leaving group substituents are eliminated without substantial elimination of the modifier group substituents to form the conjugated poly(arylene vinylene) copolymer.

23. A copolymer as claimed in claim 22, wherein the heating is carried out in a temperature range of about 70°–300° C.

24. A copolymer as claimed in claim 22, wherein the heating is carried out under acidic catalysis.

25. A copolymer as claimed in claim 22, in which the poly(arylene-1,2-ethanediyl) precursor copolymer is formed by the method comprising: reacting a first monomer component with a second monomer component in the presence of base and a solvent comprising the modifier group, wherein the first monomer component comprises a first arylene moiety substituted with —CH$_2$L$^1$ and —CH$_2$L$^2$ and the second monomer component comprises a second arylene moiety substituted with —CH$_2$L$^3$ and —CH$_2$L$^4$, in which L$^1$, L$^2$, L$^3$, and L$^4$ each represents a leaving group substituents which may be the same or different from one another.

26. A copolymer as claimed in claim 25, wherein the solvent includes water.

27. A copolymer as claimed in claim 25, wherein the solvent comprises at least 30% modifier group by weight.

28. A copolymer as claimed in claim 25, wherein the precursor copolymer is formed at a temperature in the range of about −5° C. to 10° C.

29. A copolymer as claimed in claim 25, wherein the precursor copolymer is formed by reacting a first monomer component with a second monomer component in the presence of a base and a solvent comprising the modifier group, wherein the first and second monomers are reacted for a time that does not exceed 4 hours.

30. A copolymer as claimed in claim 25, wherein the precursor copolymer is purified before the heating.

31. A copolymer as claimed in claim 25, wherein each leaving group substituent comprises a sulphonium salt.

32. A copolymer as claimed in claim 25, wherein the modifier group comprises an alkoxy group.

33. A copolymer as claimed in claim 32, wherein the alkoxy group is a methoxy group.

34. A copolymer as claimed in claim 25, wherein the first monomer component comprises para-phenylene and the second monomer component is selected from the group consisting of: 2,5 dimethoxy-para-phenylene, 2,5-thienylene, 2,5 dimethyl-para-phenylene, 2-methoxy-5-(2'-methylpentyloxy)-paraphenylene, and 2-methoxy-5-(2'-ethylhexyloxy)-para-phenylene.

35. A copolymer as claimed in claim 34, wherein the first monomer component comprises at least 70 mole % of the total amount of monomer.

36. A copolymer according to claim 15, wherein the modifier group is an alkoxy group.

37. A copolymer according to claim 36, wherein the alkoxy group is a methoxy group.

38. A copolymer according to claim 15, wherein the arylene moieties of the copolymer chain have as a first component para-phenylene and a second component selected from the group consisting of: 2,5 dimethoxy-para-phenylene; 2,5-thienylene; 2,5 dimethyl-para-phenylene; 2-methoxy-5-(2'-methylpentyloxy)-para-phenylene; and 2-methoxy-5-(2'-ethylhexyloxy)-para-phenylene.

39. A copolymer according to claim 38, wherein para-phenylene comprises at least 70 mole % of the total amount of arylene present.

40. A copolymer according to claim 38, wherein paraphenylene constitutes an amount in the range 85–95% and wherein the second component is 2,5 dimethoxy-paraphenylene.

41. A copolymer according to claim 22, wherein the poly(arylene-1,2-diethanediyl) precursor copolymer comprises:
a poly(arylene-1,2-ethanediyl) copolymer having a proportion of ethane groups substituted with a modifier group or a leaving group;
wherein the leaving group can be eliminated to form the poly (arylene vinylene) copolymer.

42. A precursor copolymer according to claim 41, wherein the leaving group comprises a sulfonium salt.

43. A conjugated poly(arylene vinylene) copolymer according to claim 15, which copolymer is formed by the method comprising: heating substantially in the absence of oxygen a poly(arylene-1,2-ethanediyl) precursor polymer effective to form a partially saturated poly(arylene vinylene) copolymer, wherein the precursor polymer has a portion of the ethane groups with a modifier group and heating is effective to eliminate a proportion of the modifier groups to form the partially saturated copolymer, wherein the proportion of the vinylic groups saturated by the modifier group substituent is effective to spatially modulate the semiconductor bandgap of the copolymer.

44. A copolymer as claimed in claim 43, wherein the poly(arylene-1,2-ethanediyl) precursor polymer comprises a homopolymer.

45. A copolymer as claimed in claim 44, wherein the homopolymer is selected from the group consisting of a poly(paraphenylene-1,2-ethanediyl) polymer, a poly(2,5 dimethoxy-para-phenylene-1,2-ethanediyl) polymer, a poly(thienylene-1,2-ethanediyl) polymer, a poly(2,5 dimethyl-para-phenylene-1,2-ethanediyl) polymer, a poly(2-methoxy-5-(2'-methylpentyloxy)-para-phenylene-1,2-ethanediyl) polymer, and a poly(2-methoxy-5-(2'-ethylhexyloxy)-para-phenylene-1,2-ethanediyl) polymer.

46. A copolymer as claimed in claim 43, wherein the heating is performed substantially in the absence of acid.

47. A copolymer as claimed in claim 43, wherein the temperature of heating is in the range of 200° to 300° C.

48. A copolymer as claimed in claim 43, wherein the heating time is up to 12 hours.

49. A copolymer as claimed in claim 34, wherein the para-phenylene constitutes an amount in the range of 85–95% and wherein the second monomer component is 2,5 dimethoxy-para-phenylene.

* * * * *

UNITED STATES PATENT AND TRADEMARK OFFICE
CERTIFICATE OF CORRECTION

PATENT NO. : 5,401,827
DATED : March 28, 1995
INVENTOR(S) : Andrew Holmes; Donal D. Bradley; Richard H. Friend; Arno Kraft; Paul Burn; Adam Brown It is certified that error appears in the above-identified patent and that said Letters Patent is hereby corrected as shown below:

Section (30), Priority, delete "9018698" and insert therefor --9018698.2--.

Column 2, line 55, after the word "type", insert --and--.

Column 3, line 3, delete "Semiconductor" and insert therefor --semiconductor--.

Column 4, line 36, delete "polycarylene" and insert therefor --poly(arylene--.

Column 7, line 56, delete "paraphenylene" and insert therefor --para-phenylene--.

Column 7, lines 57 and 58, delete "para phenylene" and insert therefor --para-phenylene--.

Column 14, lines 37 and 38, delete "para phenylene" and insert therefor --para-phenylene--.

Column 9, line 4, delete "copolpers" and insert therefor --copolymers--.

Column 10, line 35, delete "present" and insert therefor --presence--.

Column 11, line 52, should end after the word "alkali." "FIGS. 16 and 17" should start a new paragraph on line 53.

Column 13, line 26, delete "300°" and insert therefor --300°C.--.

Column 13, line 32, delete "FIGS. 39 shows" and insert therefor --FIGS. 39(a) to (c) show--.

Column 13, line 46, after the word "Line", insert --41--.

Column 13, line 47, after the word "Line", insert --41--.

UNITED STATES PATENT AND TRADEMARK OFFICE
CERTIFICATE OF CORRECTION

PATENT NO. : 5,401,827

DATED : March 28, 1995

INVENTOR(S) : Andrew Holmes; Donal D. Bradley; Richard H. Friend; Arno Kraft; Paul Burn; Adam Brown It is certified that error appears in the above-identified patent and that said Letters Patent is hereby corrected as shown below:

Column 13, line 49, after the word "Line", insert --41--.

Column 14, line 8, delete "Of" and insert therefor --of--.

Column 17, line 6, delete "Was" and insert therefor --was--.

Column 17, lines 21 and 22, delete "(0 11 g, 0 33 mmol)" and insert therefor --(0.11 g, 0.33 mmol)--.

Column 17, line 55, "1-methoxy" does not start a new paragraph.

Column 18, line 19, delete "(s, i H)" and insert therefor --(s, 1H)--.

Column 18, line 20, delete "MHZ" and insert therefor --MHz--.

Column 18, line 23, delete "126 8, 127 0," and insert therefor --126.8, 127.0,--.

Column 18, line 44, delete "(s, 3 4.56" and insert therefor --(s, 3H), 4.56--.

Column 19, line 47, delete "1.516" and insert therefor --1516--.

Column 19, line 64, delete "(m, I H)," and insert therefor --(m, 1H),--.

Column 20, line 16, delete "sigma chemical" and insert therefor --Sigma Chemical--.

Column 20, line 40, delete "26b," and insert therefor --27b,--.

Column 21, lines 61 and 62, delete "Spin-coating" and insert therefor --spin-coating--.

UNITED STATES PATENT AND TRADEMARK OFFICE
CERTIFICATE OF CORRECTION

PATENT NO. : 5,401,827
DATED : March 28, 1995
INVENTOR(S) : Andrew Holmes; Donal D. Bradley; Richard H. Friend; Arno Kraft; Paul Burn; Adam Brown It is certified that error appears in the above-identified patent and that said Letters Patent is hereby corrected as shown below:

Column 22, line 34, after the word "that", delete -.-.

Column 22, line 42, after the word "stable", delete -:-.

Column 22, line 43, after the word "considerable", delete -:-.

Column 23, line 53, delete "vinylone" and insert therefor --vinylene--.

Column 23, line 63, delete "S" and insert therefor --S.--.

Column 24, line 26, delete "Lack" and insert therefor --lack--.

Column 25, line 63, delete "A. J" and insert therefor --A. J.--.

Column 26, line 45, delete "band gap" and insert therefor --bandgap--.

Column 27, line 15, delete "Used" and insert therefor --used--.

Column 27, line 41, delete "90°" and insert therefor --90°C.--.

Column 32, line 1, delete "paraphenylene" and insert therefor --para-phenylene--.

Column 32, line 2, delete the space before the word "and".

Column 32, line 21, delete "paraphenylene" and insert therefor --para-phenylene--.

Column 32, line 23, delete "paraphenylene" and insert therefor --para-phenylene--.

Column 32, line 50, delete "paraphenylene" and insert therefor --para-phenylene--.

UNITED STATES PATENT AND TRADEMARK OFFICE
CERTIFICATE OF CORRECTION

PATENT NO. : 5,401,827
DATED : March 28, 1995
INVENTOR(S) : Andrew Holmes, et al.

It is certified that error appears in the above-indentified patent and that said Letters Patent is hereby corrected as shown below:

Column 13, line 47, after the word "Line" insert --41--.

Signed and Sealed this

Twenty-eighth Day of November 1995

Attest:

BRUCE LEHMAN

Attesting Officer

Commissioner of Patents and Trademarks